US012742157B2

(12) United States Patent
Aguirre et al.

(10) Patent No.: US 12,742,157 B2
(45) Date of Patent: Sep. 22, 2026

(54) PLURIPOTENT STEM CELL-DERIVED HEART ORGANOID

(71) Applicant: Board of Trustees of Michigan State University, East Lansing, MI (US)

(72) Inventors: Aitor Aguirre, Okemos, MI (US); Yonatan Raz Israeli, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 686 days.

(21) Appl. No.: 18/010,946

(22) PCT Filed: Jun. 17, 2021

(86) PCT No.: PCT/US2021/037808
§ 371 (c)(1),
(2) Date: Dec. 16, 2022

(87) PCT Pub. No.: WO2021/257812
PCT Pub. Date: Dec. 23, 2021

(65) Prior Publication Data

US 2023/0212526 A1 Jul. 6, 2023

Related U.S. Application Data

(60) Provisional application No. 63/155,596, filed on Mar. 2, 2021, provisional application No. 63/041,545, filed on Jun. 19, 2020.

(51) Int. Cl.
*C12N 5/071* (2010.01)
*C12N 5/077* (2010.01)

(52) U.S. Cl.
CPC ......... *C12N 5/0697* (2013.01); *C12N 5/0657* (2013.01); *C12N 2501/415* (2013.01); *C12N 2506/45* (2013.01); *C12N 2513/00* (2013.01)

(58) Field of Classification Search
CPC . C12N 5/0697; C12N 5/0657; C12N 2513/00
See application file for complete search history.

(56) References Cited

U.S. PATENT DOCUMENTS

2011/0033430 A1 2/2011 Chien et al.
2014/0221463 A1 8/2014 Aguirre et al.
2017/0037375 A1 2/2017 Palecek et al.
2018/0030410 A1 2/2018 Loh et al.
2019/0100725 A1 4/2019 Ma et al.
2025/0321226 A1 10/2025 Mendjan et al.

FOREIGN PATENT DOCUMENTS

CN 108148802 A 6/2018
WO WO-2019172756 A1 9/2019
WO WO-2019174879 A1 * 9/2019 .......... C12N 5/0656

OTHER PUBLICATIONS

Cheng, Oncotarget. May 4, 2015;6(16): 14428-14439.*
MacDonald (2009, Developmental Cell, 17:9-26).*
Katoh, Cancer Biology and Therapy, 2006, 5:1059-1064.*
Gordon, 2006, Journal of Biological Chemistry, 281:22429-22433.*
Willert, CSH Perspectives in Biology, 2012, 4:1-13.*
Richards et al. "Development of Biomimetic Models of Human Cardiac Tissue," Clemson University. Aug. 1, 2018 (Aug. 1, 2018). [Sep. 16, 2021] Retrieved from internet: <URL: https://tigerprints.clemson.edu/cgi/viewcontent.cgi?article=3195&context=all_dissertations>.
Israeli et al. "Generation of Heart Organoids Modeling Early Human Cardiac Development Under Defined Conditions," bioRxiv. Jun. 26, 2020 (Jun. 26, 2020). [Sep. 16, 2021]. Retrieved from internet: < https://doi.org/10.1101/2020.06.25.171611>.
Hofbauer et al. "Cardioids reveal self-organizing principles of human cardiogenesis," Cell. Jun. 10, 2021 (Mar. 10, 2021), vol. 184, Issue 12, pp. 3299-3317. entire document.
International Search Report and Written Opinion of the ISA issued in PCT/US2021/037808, mailed Oct. 28, 2021, ISA/US.
Doyle, Michelle J. et al. "Human Induced Pluripotent Stem Cell-Derived Cardiomyocytes as a Model for Heart Development and Congenital Heart Disease," Stem Cell Rev and Rep (2015) 11:710-727; DOI 10.1007/s12015-015-9596-6.
Richards, Dylan J., et al. "Human cardiac organoids for the modelling of myocardial infarction and drug cardiotoxicity," Nature Biomedical Engineering, vol. 4, Apr. 2020, 446-462; www.nature.com/natbiomedeng.
Poster presented at ISSCR conference Jun. 23, 2020.
Varzideh, Fahimeh et al. (2019). Coculture with noncardiac cells promoted maturation of human stem cell-derived cardiomyocyte microtissues. Journal of cellular biochemistry, 120(10): 16681-16691.

(Continued)

*Primary Examiner* — Valarie E Bertoglio
(74) *Attorney, Agent, or Firm* — Harness, Dickey & Pierce, P.L.C.

(57) ABSTRACT

A method for generating a heart organoid is provided. The method includes forming a cellular aggregate of pluripotent stem cells, activating Wnt signaling in the cellular aggregate to cause the cellular aggregate to differentiate into a three-dimensional cardiac mesoderm, and inhibiting the Wnt signaling in the cardiac mesoderm to form the heart organoid. The heart organoid includes myocardial tissue, endocardial tissue defining at least one chamber, and epicardial tissue disposed on at least an outer surface of the myocardial tissue. The heart organoid beats. Heart organoids prepared in accordance with the method are also provided.

18 Claims, 40 Drawing Sheets

(56) References Cited

OTHER PUBLICATIONS

Yan, Yuanwei et al. (2019). Cell population balance of cardiovascular spheroids derived from human induced pluripotent stem cells. Scientific reports, vol. 9(1):1295.
Giacomelli, Elisa et al. (2017). Three-dimensional cardiac microtissues composed of cardiomyocytes and endothelial cells co-differentiated from human pluripotent stem cells. Development (Cambridge, England), 144,6: 1008-1017.
Gyuhyung Jin et al. (2020). Inductive factors for generation of pluripotent stem cell-derived cardiomyocytes. In: Engineering Strategies for Regenerative Medicine, Elsevier Science and Technology, 177-242.
Supplementary European Search Report from EP Application No. 218258663 dated Jul. 9, 2024.
Office Action from Chinese Application No. 202180043664.4 dated Jun. 25, 2025.

* cited by examiner

****
****
*
% TNNT2 positive area
100
80
60
40
20
0
4
6.6
8
CHIR99021 (μM)

% TNNT2 positive area
iPSC-L1
iPSC-AICS
iPSCORE16
ESC-H9

Beats per minute
50
40
30
20
10
0
iPSC-L1
iPSC-AICS
iPSCORE16
ESC-H9

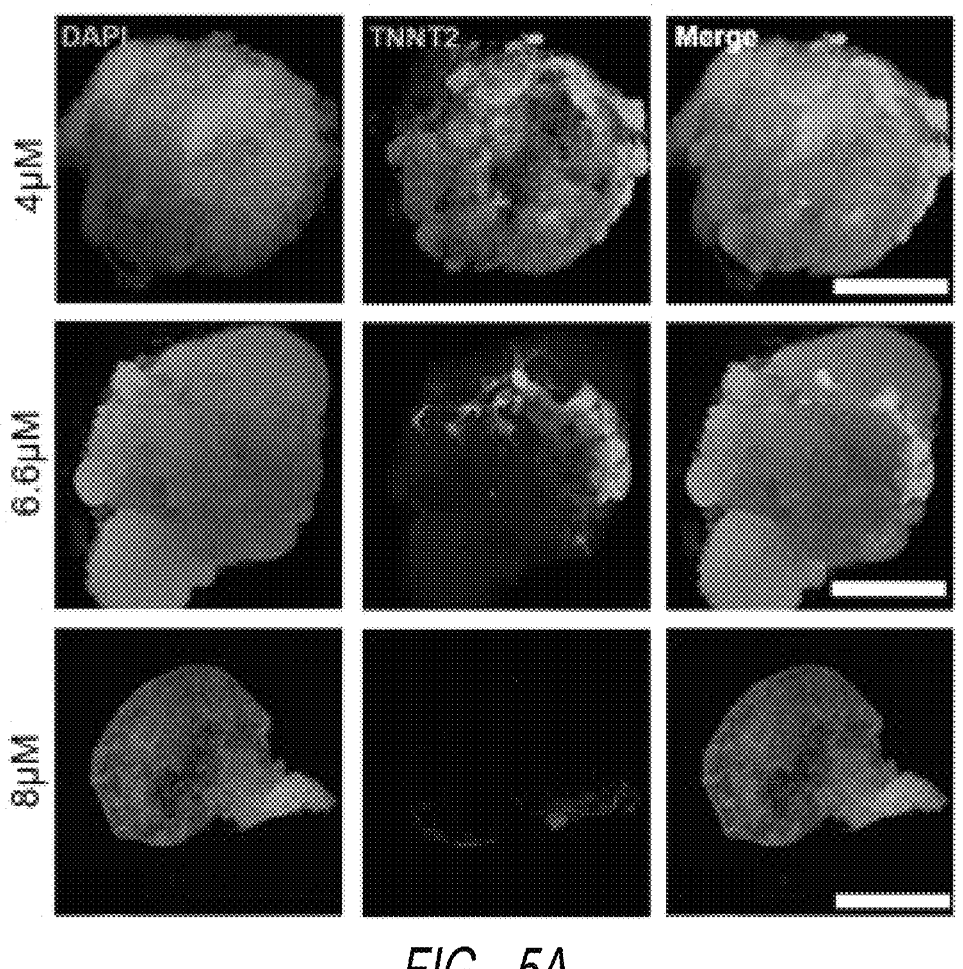
FIG - 5A
Beats per minute
60
40
20
0
****
ns
****
4
6.6
8
CHIR99021 (μM)
FIG - 5B
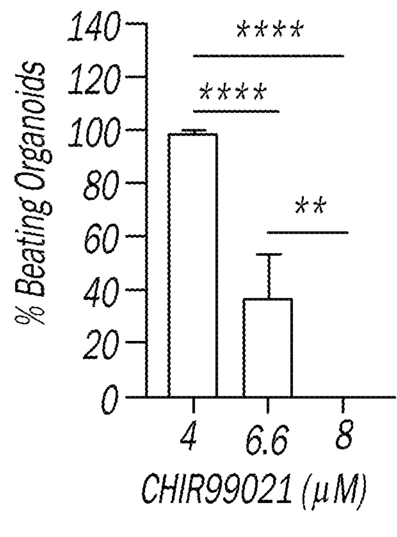
FIG - 5C

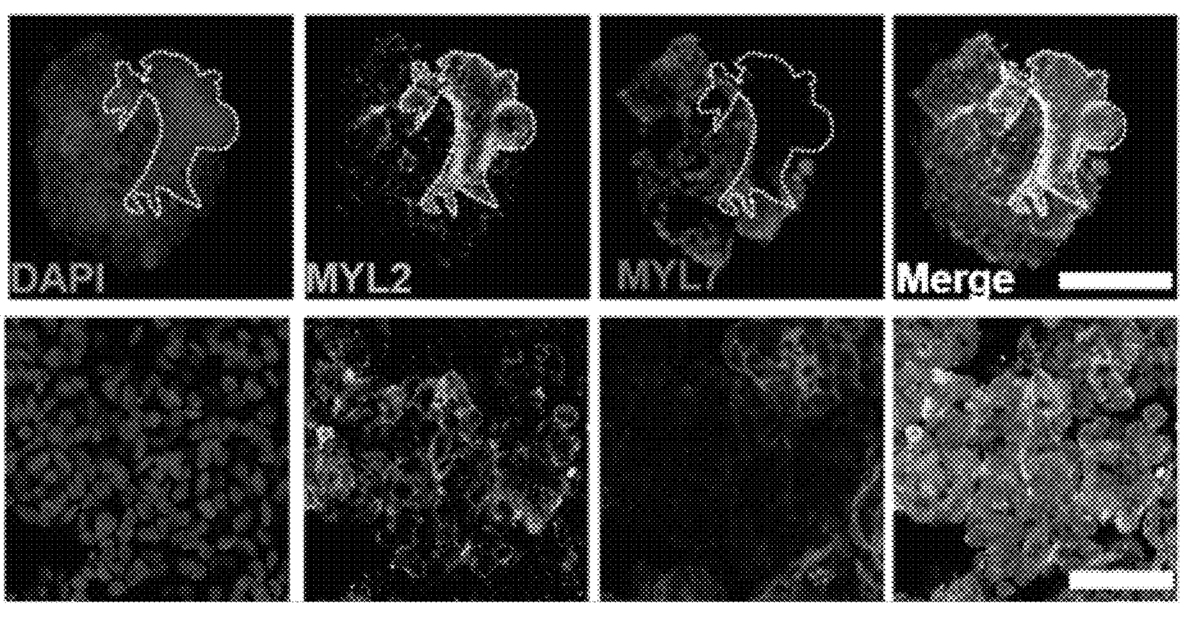
FIG - 10C
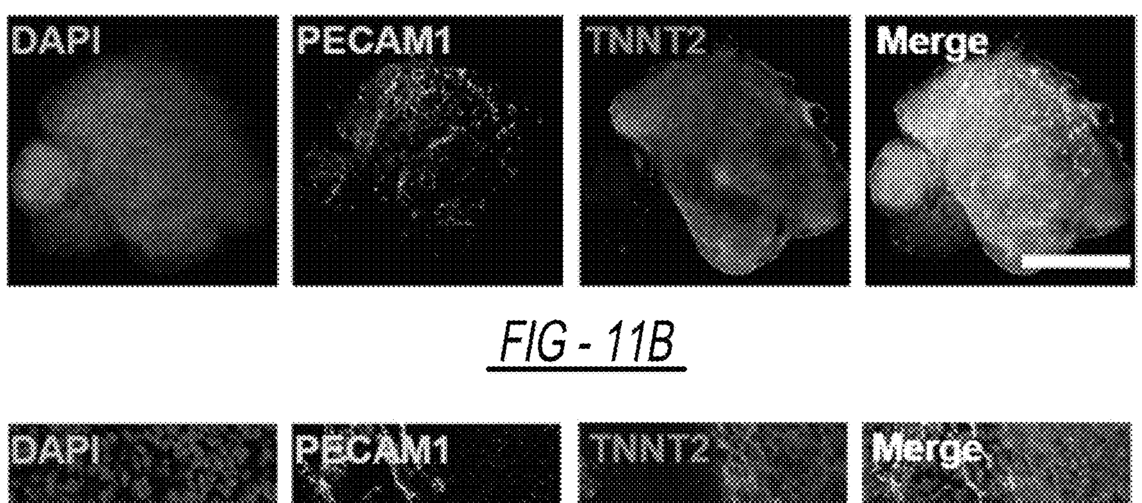
FIG - 11B
FIG - 11C p<0.05
80
40
20
0
Microchambers
Control
+BMP4+ActA p<0.05
100
50
0
% Microchambers interconnected
Control
+BMP4+ActA p<0.05
4
3
2
1
0
-1
%PECAM1+
Control
+BMP4+ActA

PLURIPOTENT STEM CELL-DERIVED HEART ORGANOID

CROSS-REFERENCE TO RELATED APPLICATIONS

This application is a U.S. National Phase Application under 35 U.S.C. 371 of International Application No. PCT/US2021/037808, filed Jun. 17, 2021, which claims the benefit of U.S. Provisional Patent Application Ser. No. 63/041,545, filed on Jun. 19, 2020 and 63/155,596, filed on Mar. 2, 2021. The entire contents of the above applications are incorporated by reference herein.

GOVERNMENT RIGHTS

This invention was made with government support under HL135464 awarded by the National Institutes of Health. The government has certain rights in the invention.

FIELD

The present disclosure relates to pluripotent stem cell-derived heart organoids.

BACKGROUND

This section provides background information related to the present disclosure which is not necessarily prior art.

Cardiovascular diseases (CVD) and congenital heart diseases (CHD) are, respectively, the leading cause of death in the developed world and the most common type of congenital defect in humans. Despite the importance of understanding human cardiovascular disorders for treatment and prevention, progress on the creation of human heart organoid models for CVD studies has been very limited and lags significantly behind progress that has been achieved for other organs (e.g., kidney, colon, intestine, brain). Human pluripotent stem cells (hPSCs) can be used to recapitulate important developmental steps in vitro to produce specific cardiac cell types with relative ease, high purity, and in large amounts. However, current cell models are still very different from the structural and cellular complexity of the tissues and organs they intend to represent (e.g., lack of a three-dimensional matrix, disorganized cells, and absence of multicell-type interactions), resulting in frequently studying isolated cell types and minimizing or ignoring other heart cells (e.g., epicardial cells, endocardial cells) or the contribution of cell-cell communication in relation to a disease phenotype. There is a strong demand to bridge this technological and knowledge gap, since producing more faithful in vitro models of the human heart will allow for better modeling of health and disease states for research and translational applications.

Significant attempts have been made over the last two decades to produce more complex, multicell-type three-dimensional heart tissue using tissue engineering approaches to cover the need for in vitro human heart models. While these approaches allow for high control of the end construct, they tend to be expensive, work-intensive, and not readily scalable. Furthermore, they do not faithfully represent the original cell composition (e.g., use of dermal fibroblasts or human umbilical cord endothelial cells (HUVECs)) and organization (e.g., cardiospheres) of the heart. These approaches yield functional tissues, but fall short in terms of physiological and structural relevance, as well as cell and extracellular matrix (ECM) complexity. Accordingly, organoids that more closely resemble the human heart are desired.

SUMMARY

This section provides a general summary of the disclosure, and is not a comprehensive disclosure of its full scope or all of its features.

In various aspects, the current technology provides a method for generating a heart organoid, the method including forming a cellular aggregate including pluripotent stem cells, activating Wnt signaling in the cellular aggregate to cause the cellular aggregate to differentiate into a three-dimensional cardiac mesoderm, and inhibiting the Wnt signaling in the three-dimensional cardiac mesoderm to form the heart organoid, wherein the heart organoid includes myocardial tissue, endocardial tissue defining at least one chamber, and epicardial tissue disposed on at least an outer surface of the myocardial tissue and wherein the heart organoid beats.

In one aspect, the activating the Wnt signaling includes contacting the cellular aggregate with a glycogen synthase kinase-3 (GSK-3) inhibitor.

In one aspect, the GSK-3 inhibitor is CHIR99021.

In one aspect, the method further includes, simultaneously with the activating the Wnt signaling, contacting the cellular aggregate with at least one growth agent.

In one aspect, the inhibiting the Wnt signaling includes contacting the three-dimensional cardiac mesoderm with a Porcupine (PORCN) inhibitor.

In one aspect, the PORCN inhibitor is Wnt-059.

In one aspect, the method further includes activating Wnt signaling in the heart organoid to increase the amount of proepicardial tissue in the heart organoid.

In one aspect, the heart organoid is generated in media including glucose at a concentration of greater than or equal to about 2 mM to less than or equal to about 7 mM and insulin at a concentration of greater than or equal to about 20 pM to less than or equal to about 250 pM.

In one aspect, the heart organoid is generated in media including glucose at a concentration of greater than or equal to about 8 mM to less than or equal to about 30 mM and insulin at a concentration of greater than or equal to about 250 pM to less than or equal to about 75 nM.

The current technology also provides a heart organoid prepared according to the above method.

In various aspects, the current technology further provides a method for generating a heart organoid, the method including forming a cellular aggregate including pluripotent stem cells; contacting the cellular aggregate with a first Wnt signaling pathway activator for greater than or equal to about 2 hours to less than or equal to about 48 hours to activate Wnt signaling in the cellular aggregate and to cause the cellular aggregate to differentiate into a three-dimensional cardiac mesoderm; contacting the three-dimensional cardiac mesoderm with a Wnt signaling pathway inhibitor for greater than or equal to about 24 hours to less than or equal to about 72 hours to inhibit the Wnt signaling in the cellular aggregate and to form the heart organoid, the heart organoid including a three-dimensional body having an interior portion and an outer surface, the interior portion including myocardial tissue, endocardial tissue defining at least one chamber, and epicardial tissue disposed on at least a portion of the outer surface, wherein the heart organoid beats; and contacting the heart organoid with a second Wnt signaling pathway activator for greater than or equal to about 15 minutes to less than or equal to about 24 hours to activate Wnt signaling in the heart organoid and to generate additional epicardial tissue and proepicardial cells in the heart organoid.

In one aspect, the contacting the cellular aggregate with the first Wnt signaling pathway activator includes contacting the cellular aggregate with a Wnt-activating composition including greater than or equal to about 1 μM to less than or equal to about 15 μM of CHIR99021.

In one aspect, the contacting the three-dimensional cardiac mesoderm with the Wnt signaling pathway inhibitor includes contacting the three-dimensional cardiac mesoderm with a Wnt-inhibiting composition including greater than or equal to about 1 μM to less than or equal to about 15 μM of Wnt-059.

In one aspect, the contacting the heart organoid with the second Wnt signaling pathway activator includes contacting the cellular aggregate with a Wnt-activating composition including greater than or equal to about 1 μM to less than or equal to about 15 μM of CHIR99021.

In one aspect, the forming the cellular aggregate includes transferring the pluripotent stem cells to a substrate and centrifuging the substrate at greater than or equal to about 50 g to less than or equal to about 500 g for greater than or equal to about 1 minute to less than or equal to about 10 minutes.

In one aspect, the forming the cellular aggregate is performed on day −2, the contacting the cellular aggregate with the first Wnt signaling pathway activator is performed on day 0, the contacting the three-dimensional cardiac mesoderm with the Wnt signaling pathway inhibitor is performed on day 2, and the contacting the heart organoid with the second Wnt signaling pathway activator is performed on day 7.

In one aspect, the method also includes, in addition to the contacting the cellular aggregate with the first Wnt signaling pathway activator, contacting the cellular aggregate with at least one growth factor on day 0.

The current technology also provides a heart organoid prepared according to the above method.

In various aspects, the current technology additionally provides a heart organoid including a three-dimensional body having an interior portion and an outer surface, the interior portion including myocardial tissue; endocardial cells defining at least one chamber within the myocardial tissue; and epicardial tissue disposed on at least a portion of the outer surface, wherein the heart organoid beats and the heart organoid is derived from cultured pluripotent stem cells.

In one aspect, the heart organoid further includes endothelial vasculature at least partially embedded within the heart organoid and cardiac fibroblasts disposed within the myocardial tissue.

In one aspect, the heart organoid further includes a heart-specific extracellular matrix.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 4A:
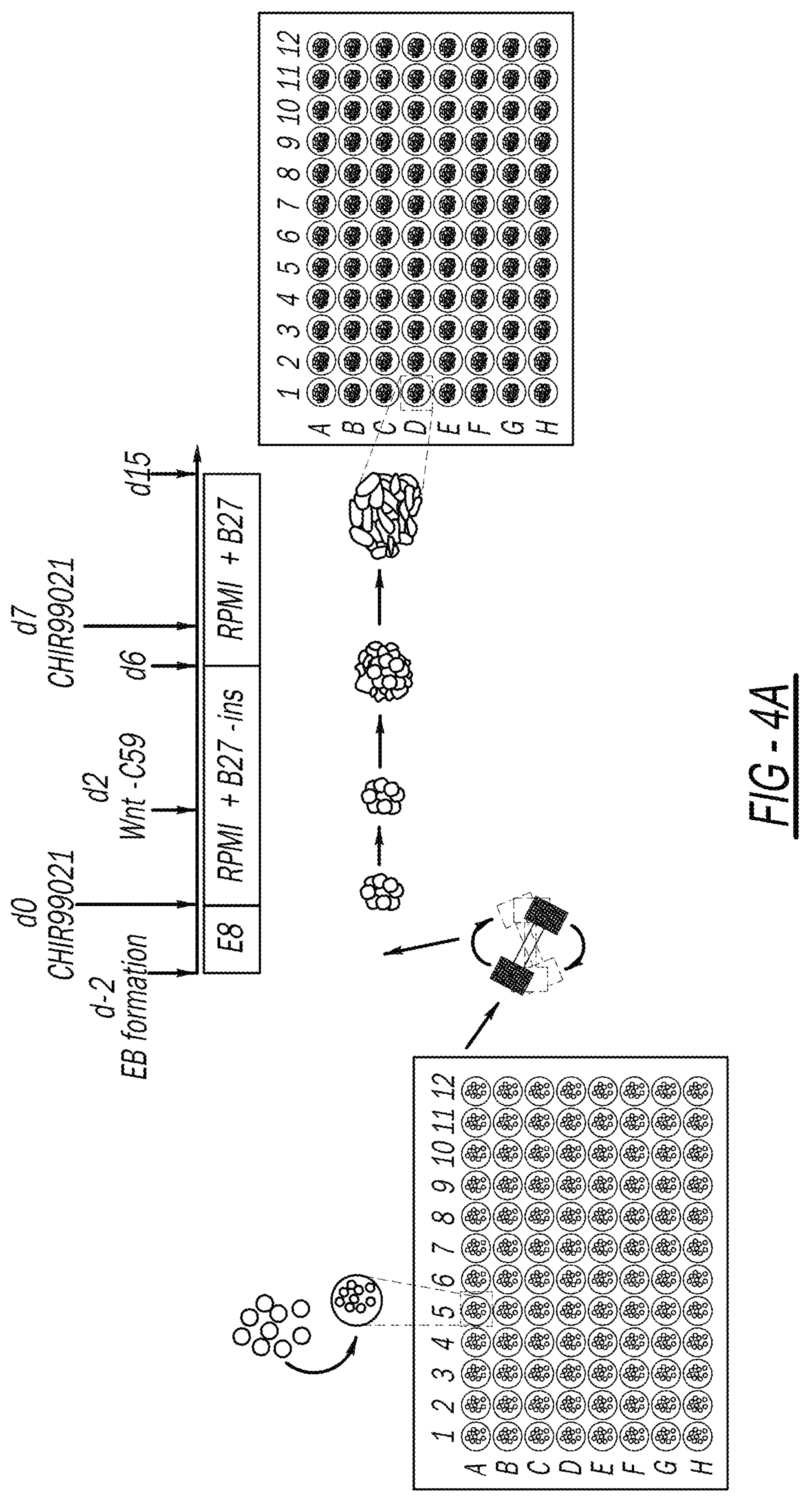
Figure 4B:
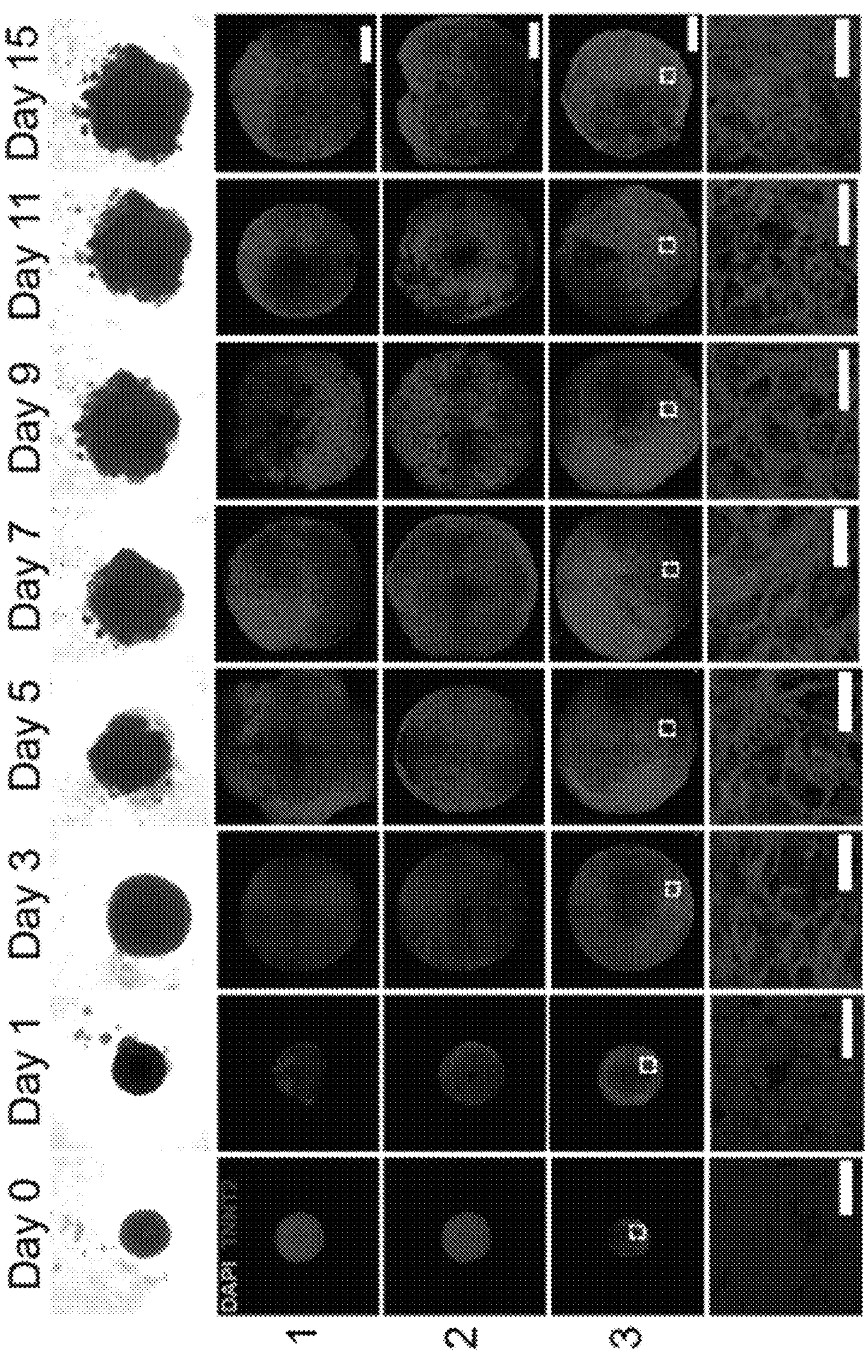
Figure 4C:
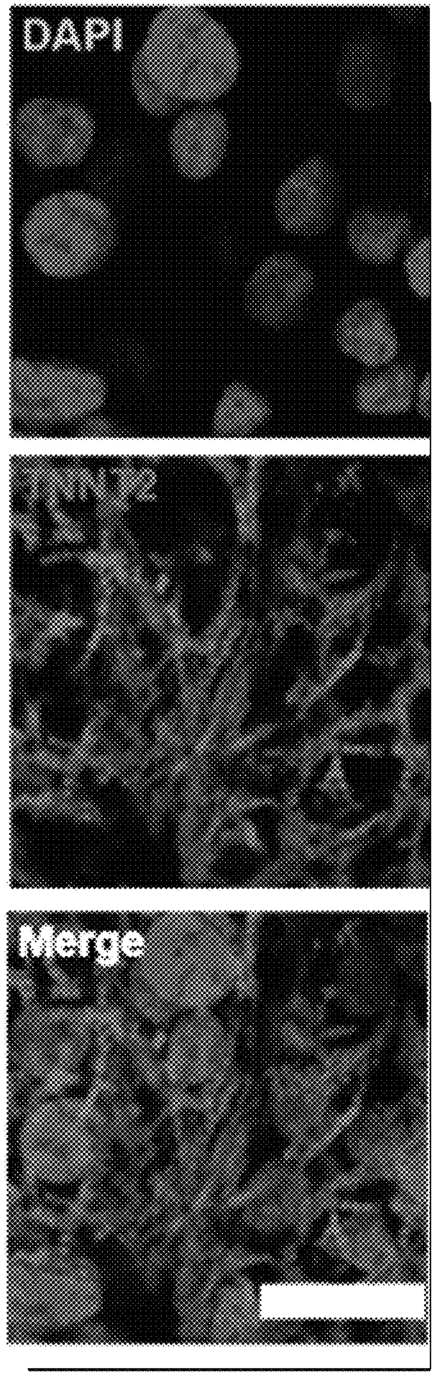
Figures 4D, 4E, 4F:
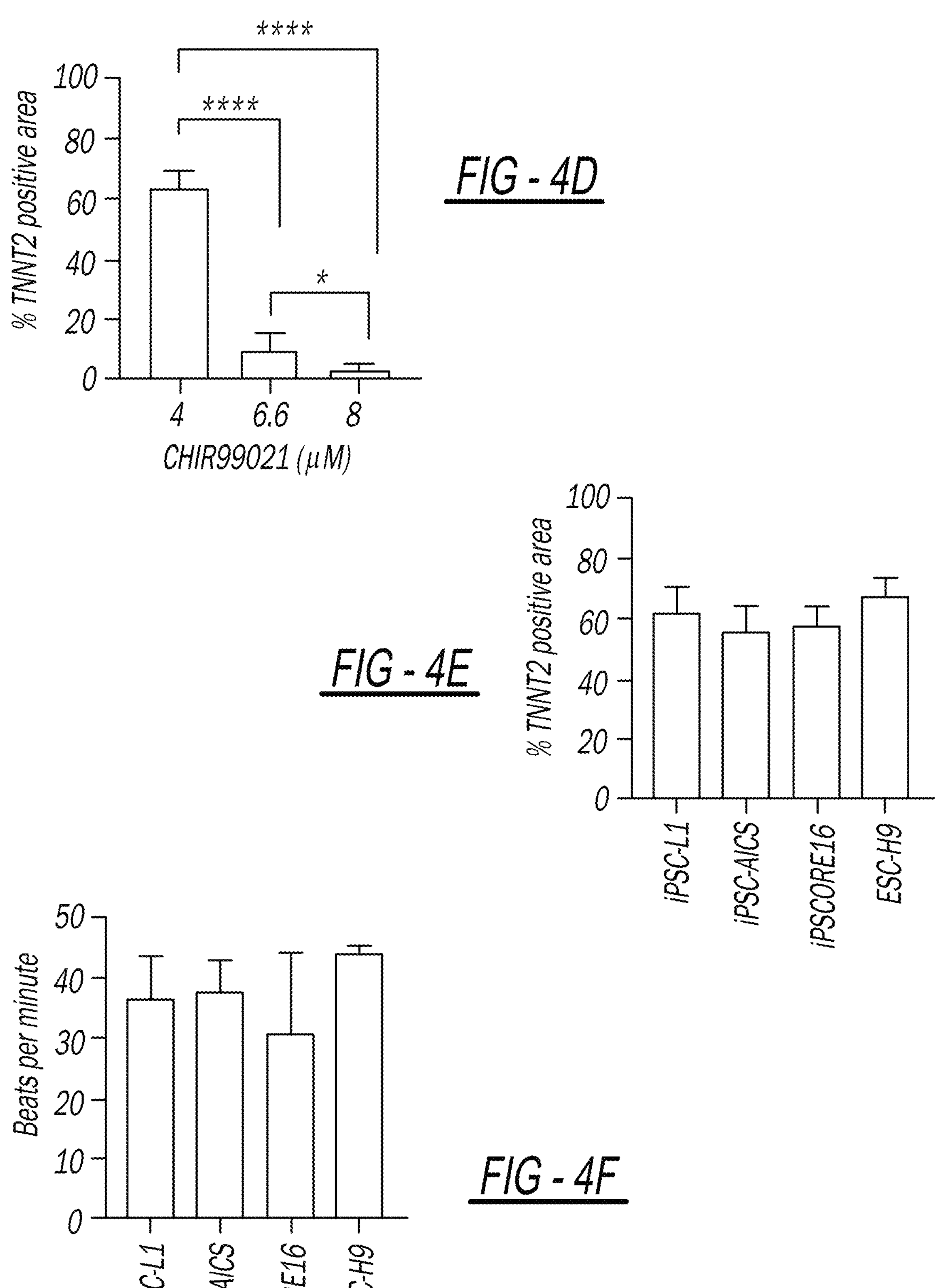

FIGS. 4A-4F provide data showing Wnt signaling-directed cardiomyocyte differentiation in human heart organoids (hHOs) in accordance with various aspects of the current technology. FIG. 4A is a schematic diagram depicting a protocol used to differentiate TNNT2+ cardiomyocytes in embryoid bodies. CHIR99021 concentration is variable at day 0. FIG. 4B shows brightfield images of a developing organoid over 15 days of differentiation (top) and confocal immunofluorescent images for DAPI (blue) and TNNT2 (red) of three representative organoids per day from day 0-15 (scale bar: 500 μm, inset: 50 μm). FIG. 4C shows confocal immunofluorescent images for DAPI (blue) and TNNT2 (red) in day-15 organoids differentiated using 4 μM CHIR showing sarcomere bands (scale bar: 25 μm). FIG. 4D shows an area analysis of cardiomyocyte regions within organoids taken at multiple z-planes as a percentage of TNNT2+ regions to DAPI+ regions of each organoid for the three CHIR99021 concentrations separately (n=10 for the 4 μM CHIR99021 treatment, n=6 for 6.6 μM and 8 μM). FIG. 4E is a graph showing the percentage of TNNT2+ area normalized to DAPI+ area in confocal images of hHOs, and FIG. 4F is a graph showing the beating frequency in three induced pluripotent stem cells (iPSC) lines and one embryonic stem cell (ESC) line. (Value=mean±s.d., one-way ANOVA multiple comparison test; *$p<0.05$, ****$p<0.0001$.)

FIGS. 5A-5C provide additional data showing Wnt signaling-directed cardiomyocyte differentiation in hHOs in accordance with various aspects of the current technology. FIG. 5A shows confocal immunofluorescent images for DAPI (blue) and TNNT2 (red) in organoids with CHIR99021 exposure concentrations of 4 μM (top), 6.6 μM (middle), and 8 μM (bottom) at day 15 (scale bars: 500 μm). FIG. 5B is a graph showing the frequency of beats per minute of the hHOs, and FIG. 5C is a graph showing the percentage of beating hHOs per treatment. (Value=mean±s.d., one-way ANOVA multiple comparison test; $p<0.01$, **$p<0.0001$.)

Figure 6A:
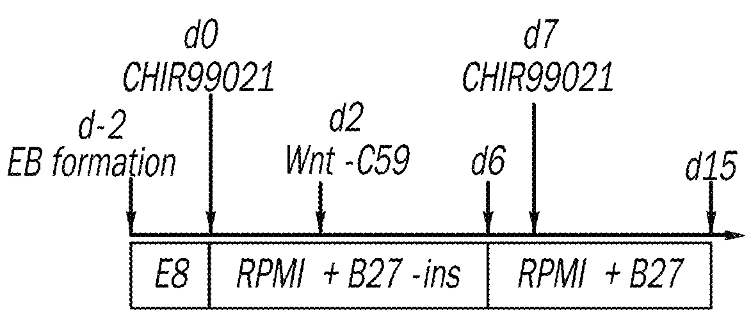
Figure 6B:
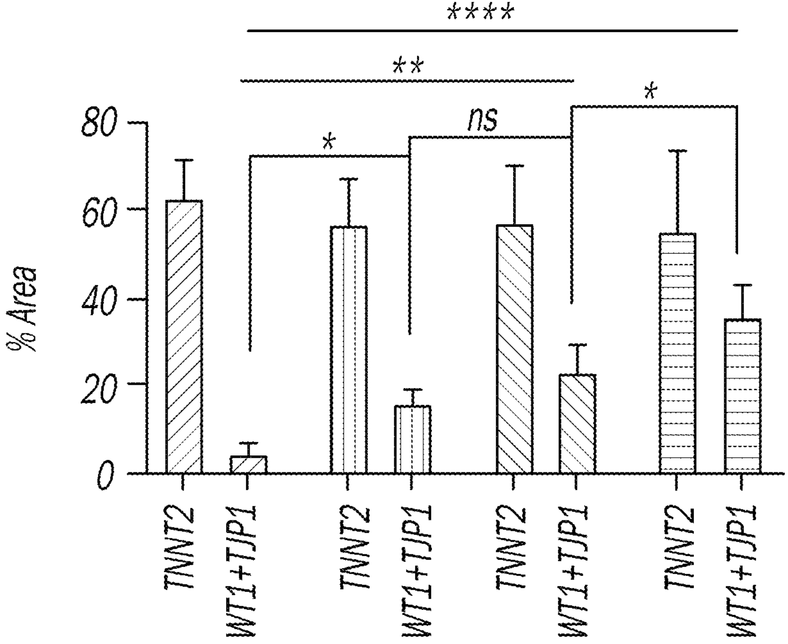
Figures 6C, 6D:
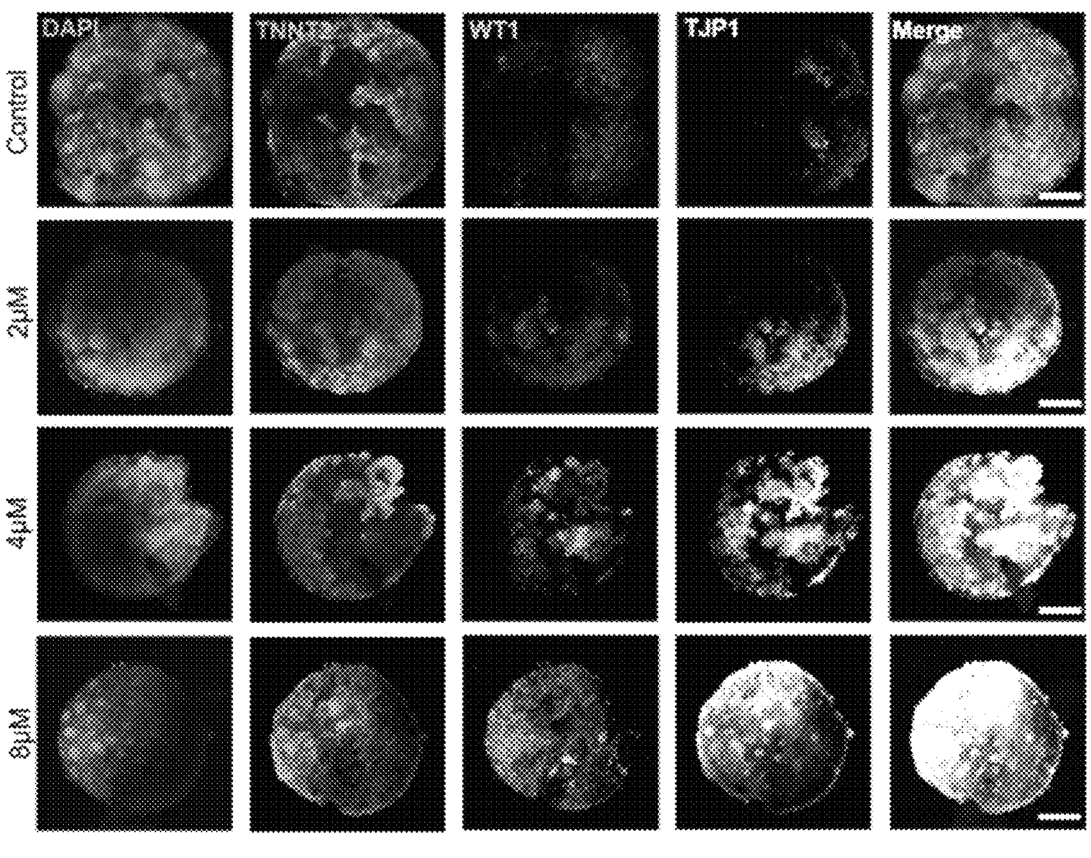

FIGS. 6A-6D provide data showing that a second CHIR exposure directs epicardial cell differentiation in hHOs in accordance with various aspects of the current technology. FIG. 6A is a schematic diagram depicting the modified protocol used to differentiate TNNT2+ cardiomyocytes and WT1+/TJP1+ epicardial cells in hHOs. FIG. 6B shows an area analysis of cardiomyocyte regions (TNNT2+) and epicardial regions (WT1+ and TJP1+) within organoids taken at multiple z-planes as a percentage of DAPI+ regions of each organoid (n=7 per condition). FIG. 6C shows confocal immunofluorescent images of hHOs at differentiation day 15 for DAPI (blue), WT1 (green), TNNT2 (red), and TJP1 (white) with variable concentrations of the second CHIR exposure at day 7 versus a control with no second CHIR exposure (scale bars: 500 μm), and FIG. 6D shows high-magnification images of hHOs with a 2 μM second CHIR exposure showing adjacent regions of TNNT2+ myocardial tissue and WT1+/TJP1+ epicardial tissue (scale bar:

50 μm). (Value=mean±s.d., two-way ANOVA multiple comparison test; *p<0.05, p<0.01, **p<0.0001.)

Figure 7A:
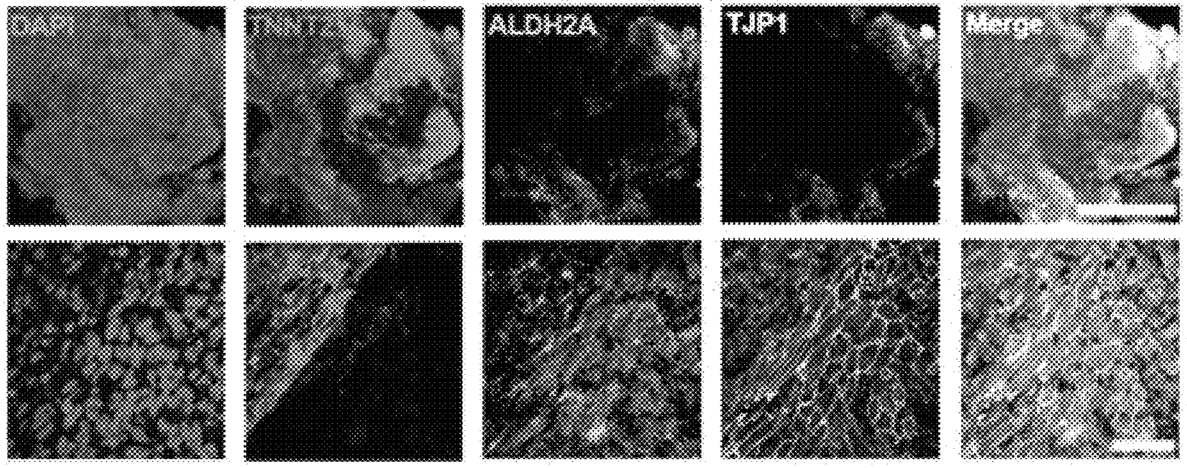
Figure 7B:
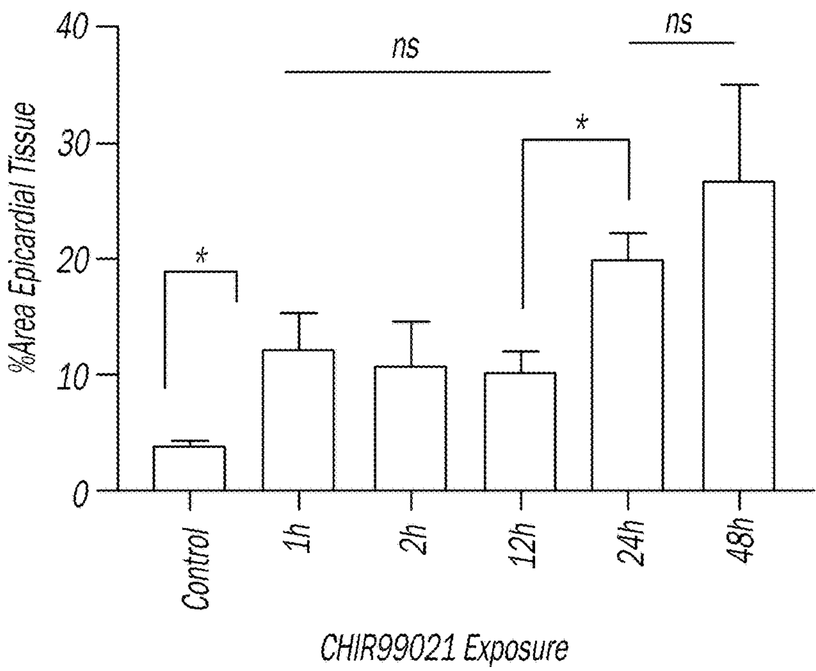
Figures 7C, 8B:
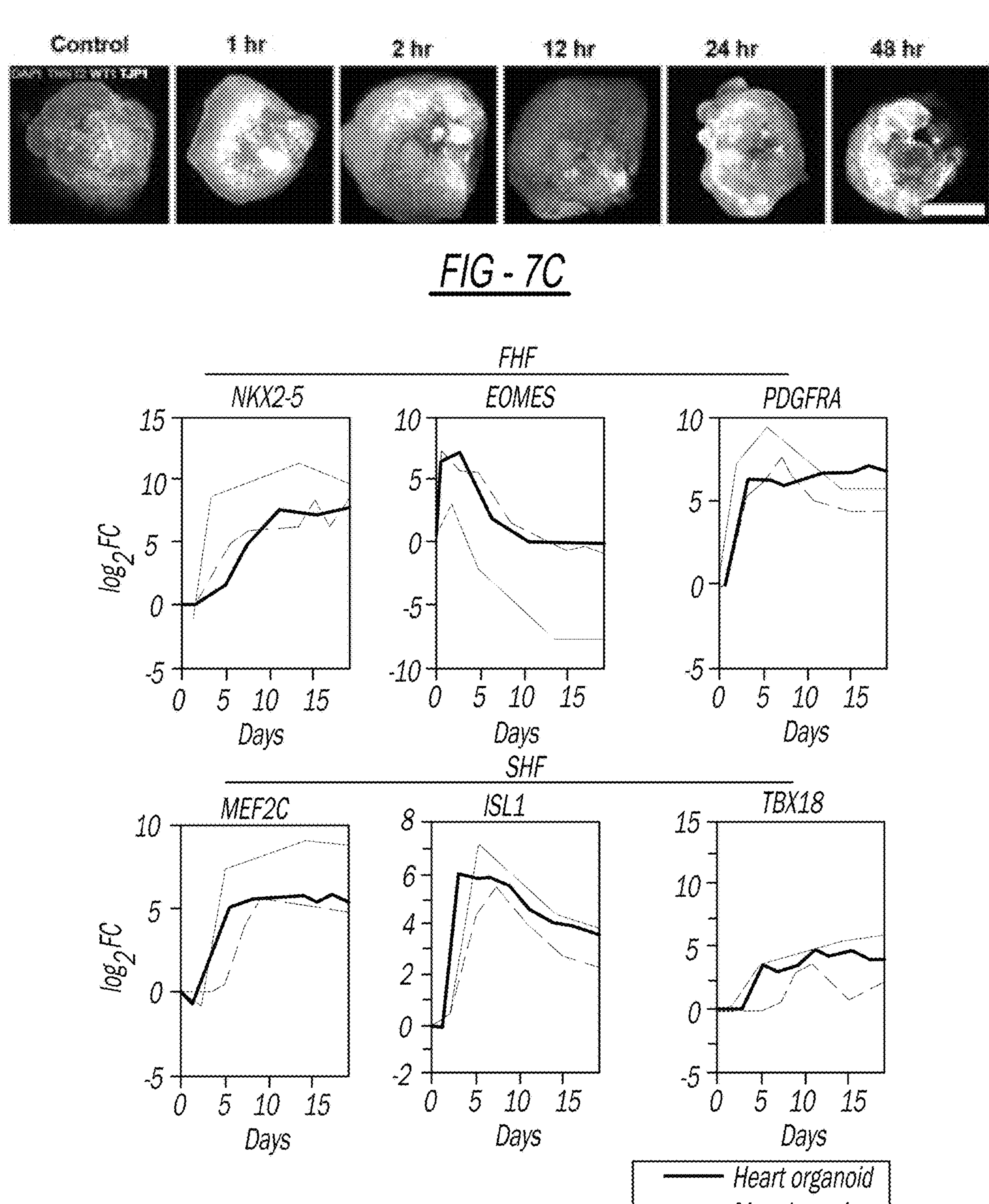

FIGS. 7A-7C provide additional data showing that a second CHIR exposure directs epicardial cell differentiation in hHOs in accordance with various aspects of the current technology. FIG. 7A shows confocal immunofluorescent images for DAPI (blue) and TNNT2 (red) in hHOs showing epicardial markers ALDH2A (green) and TJP1 (white) near edges of the organoid. FIG. 7B is an area analysis of cardiomyocyte regions (TNNT2+) and epicardial regions (WT1+ and TJP1+) within organoids taken at multiple z-planes as a percentage of DAPI+ regions of each organoid treated with CHIR99021 at day 7 for different time durations, and FIG. 7C shows representative confocal immunofluorescent images of organoids from these time durations (scale bar: 500 μm). (Value=mean±s.d., one-way ANOVA multiple comparison test; *p<0.05.)

Figure 8A:
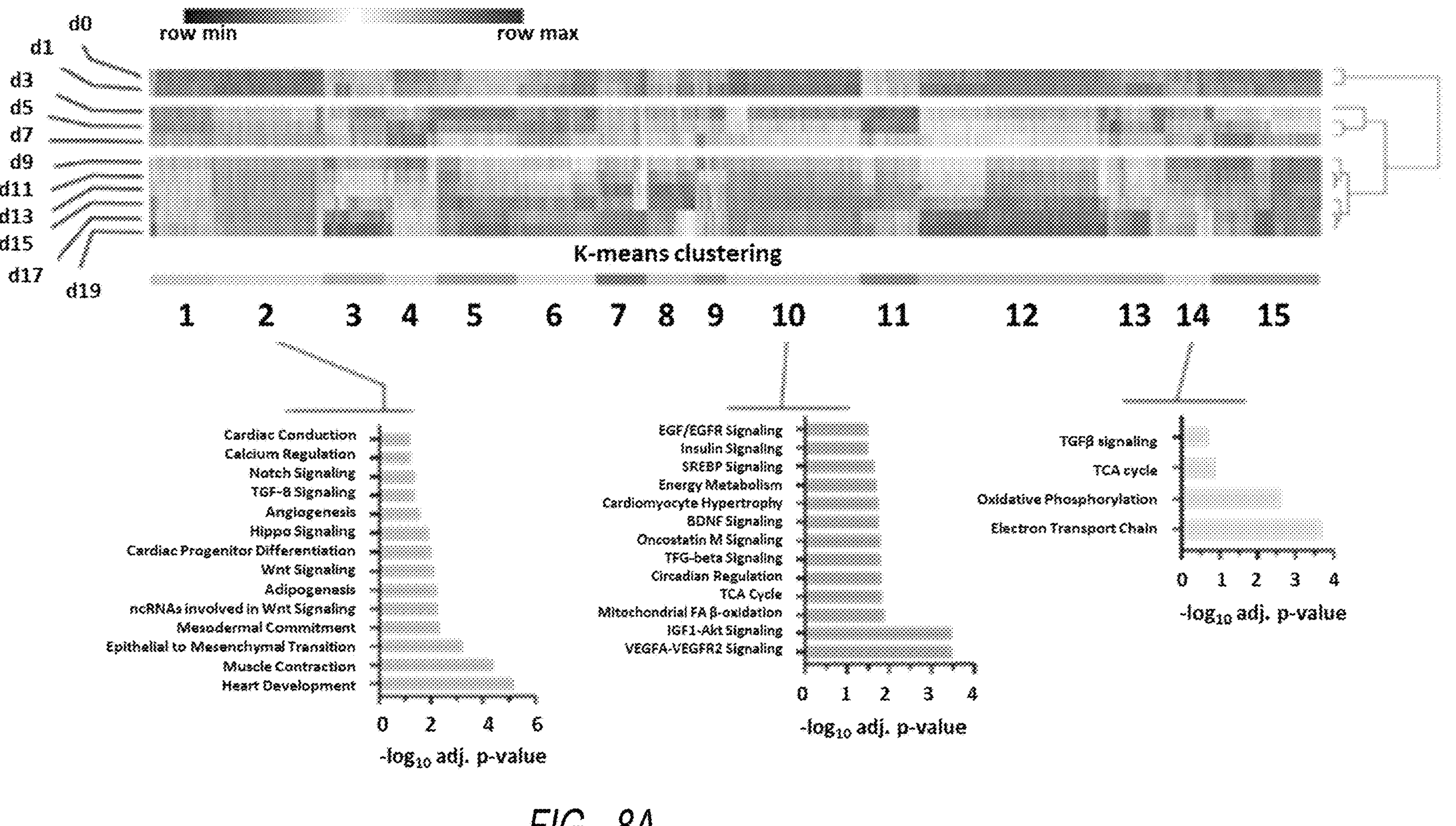
Figure 8C:
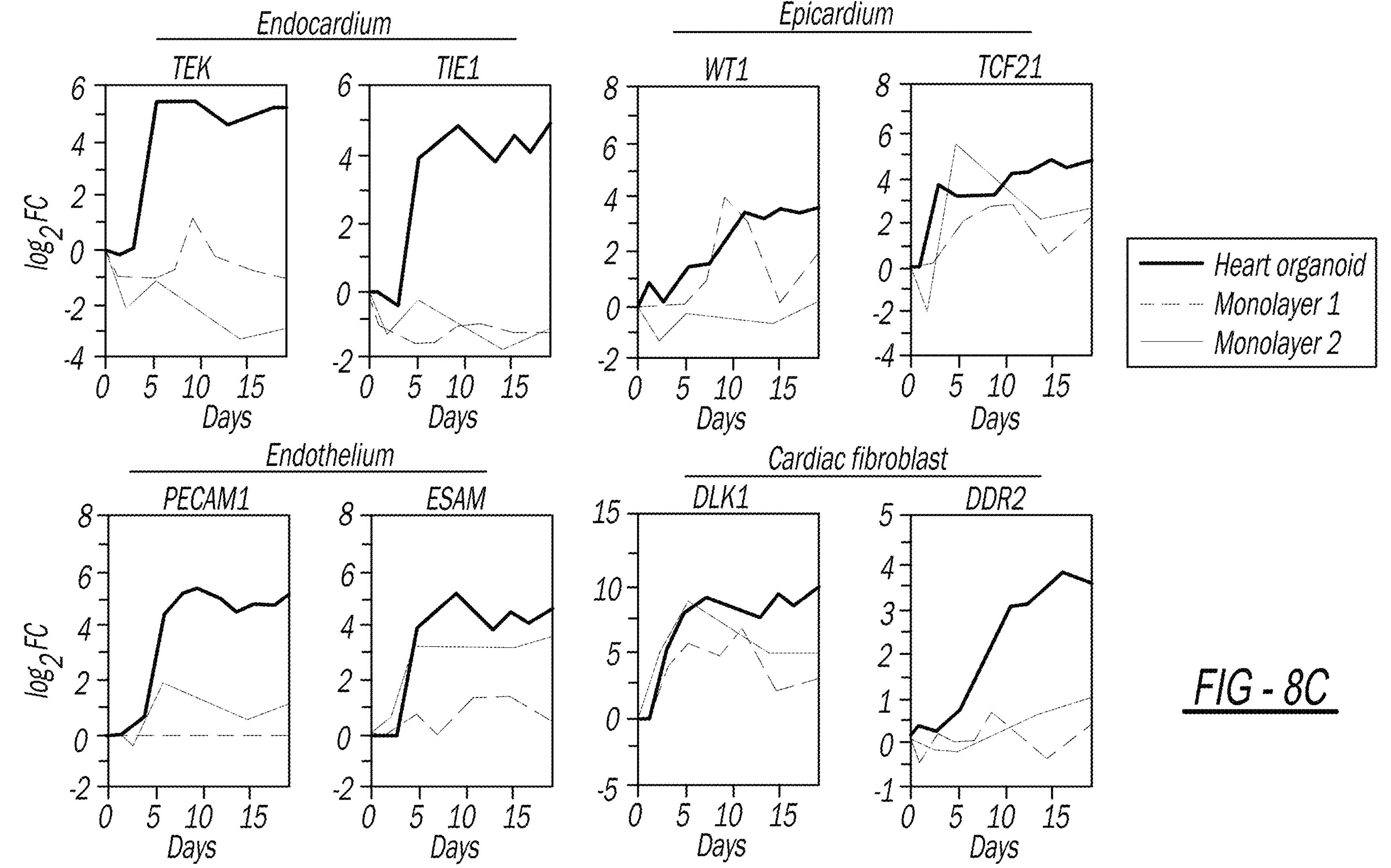
Figure 8D:
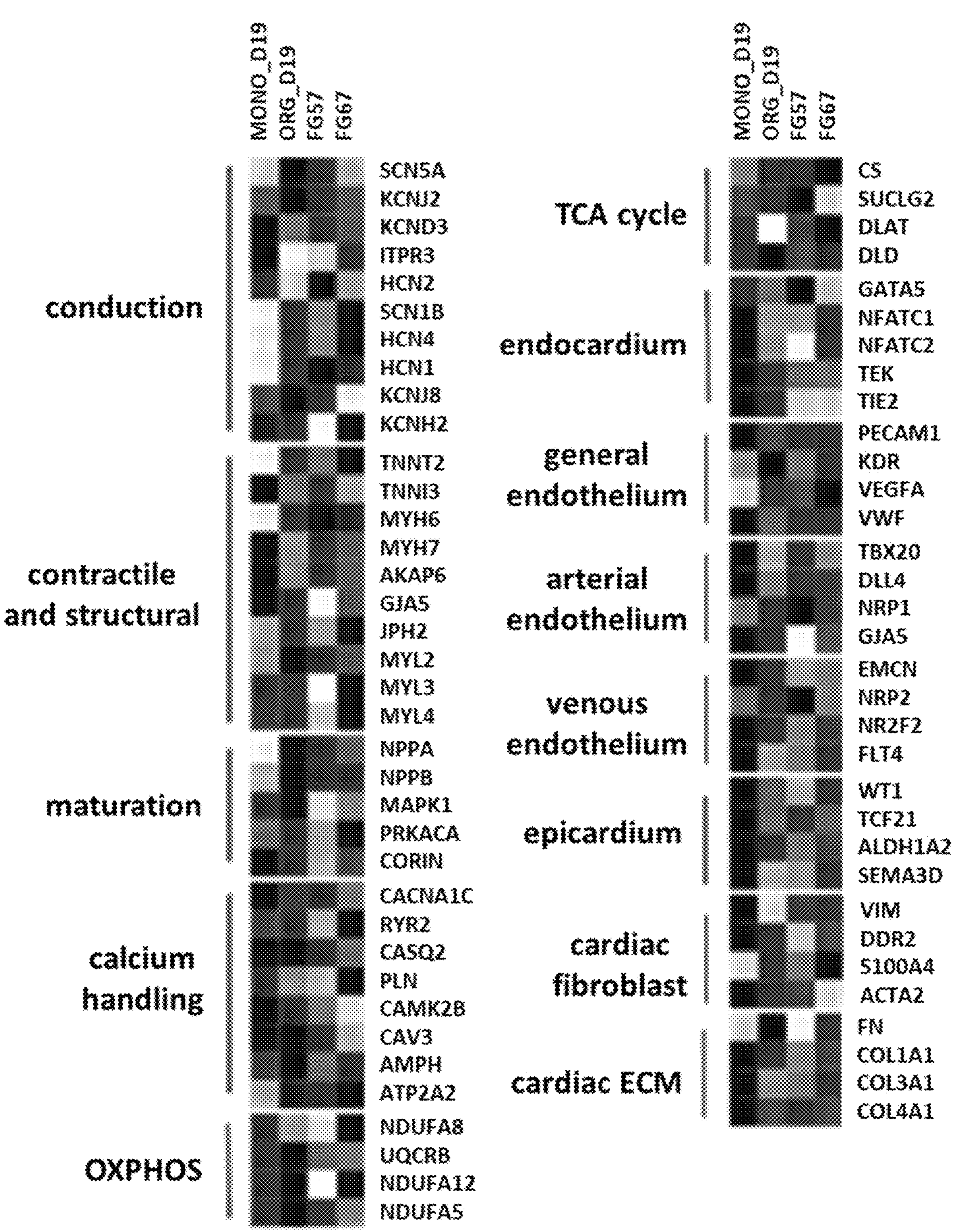
Figure 8E:
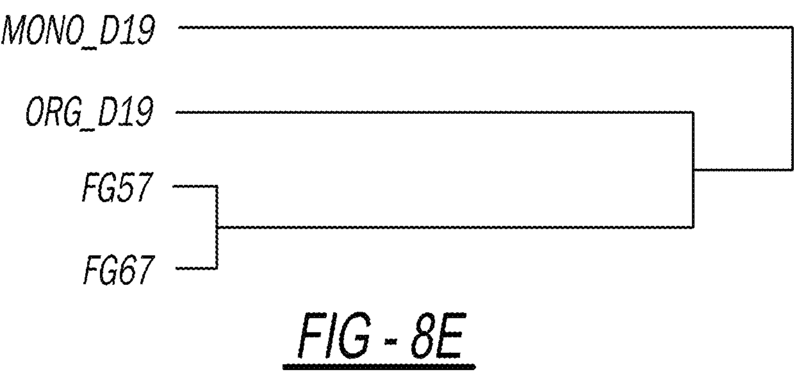

FIGS. 8A-8E show a transcriptomic analysis indicating that heart organoids prepared in accordance with various aspects of the current technology recapitulate multicell-type complexity, development, and maturation steps similar to embryonic fetal hearts. FIG. 8A shows a K-means cluster analysis of heart organoid transcriptomes by RNA sequencing (RNA-seq). Clusters strongly associated with fetal heart development (e.g., 2, 10, and 14) appear from day 9 onwards. Pathway enrichment analysis is also provided for representative cardiac-specific clusters (bottom). FIG. 8B shows a gene expression analysis (log2 fold-change versus D0) of first and second heart field markers (FHF and SHF, respectively) over the heart organoid differentiation process. FIG. 8C shows a gene expression analysis (log2 fold-change versus D0) for cardiac-specific cell-type populations in heart organoids, including epicardial cells, fibroblasts, endocardial cells, and endothelium. FIG. 8D shows a normalized comparison of key genes involved in cardiac function across heart organoids, monolayer differentiation methods, and fetal hearts at gestational day 57-67. FIG. 8E shows a hierarchical clustering analysis of heart organoids, monolayer differentiation, and fetal hearts.

Figure 9A:
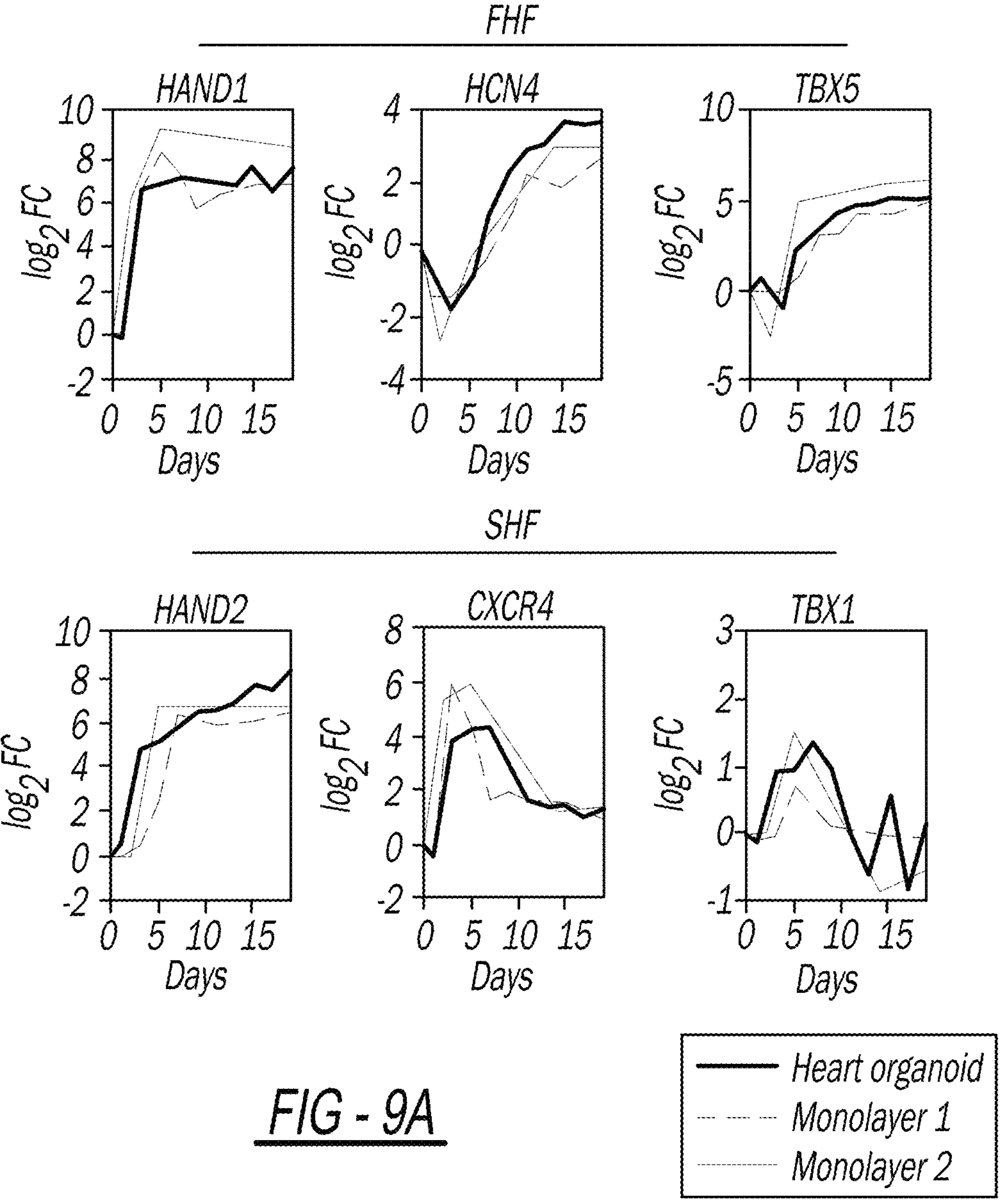
Figure 9B:
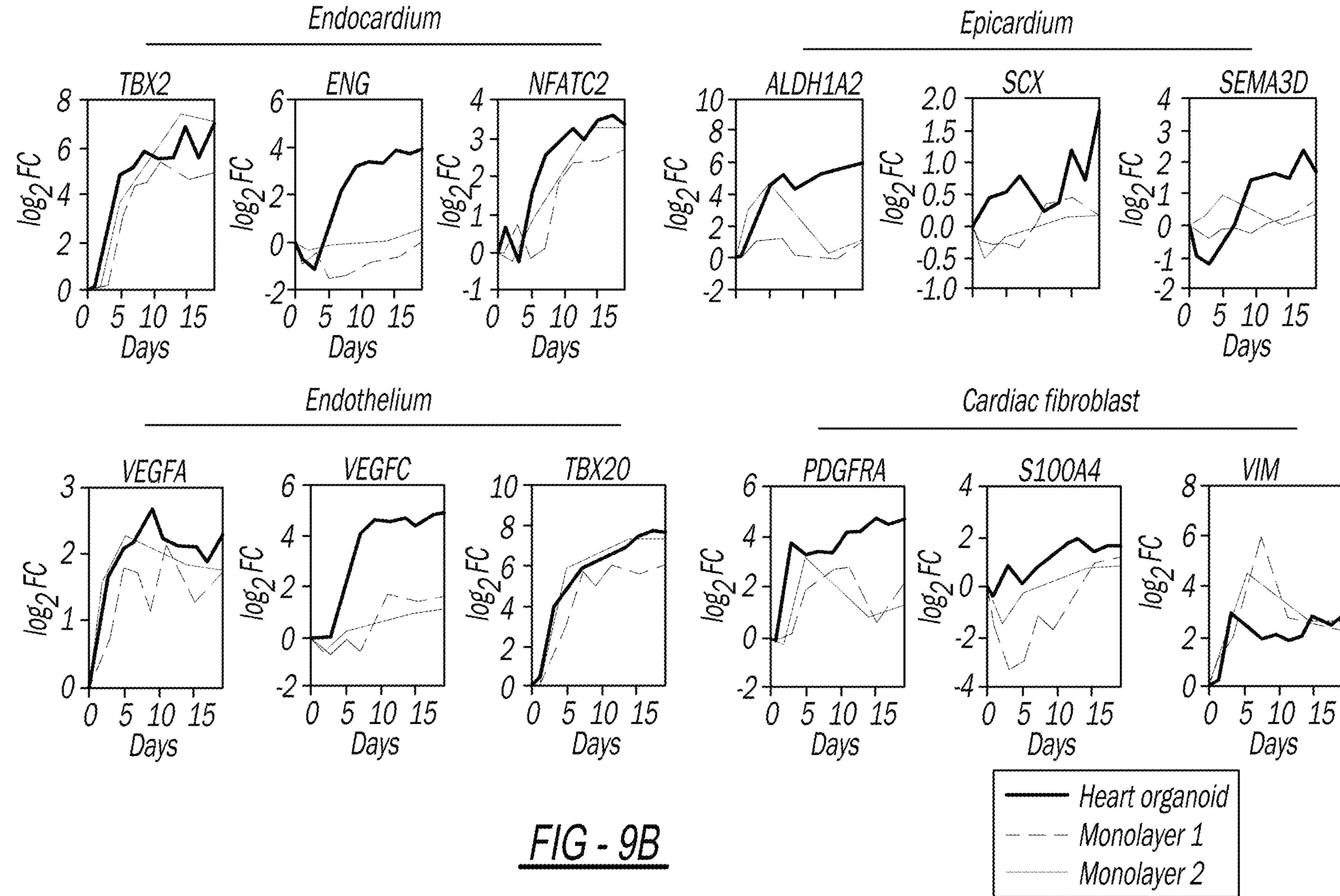
Figure 9C:
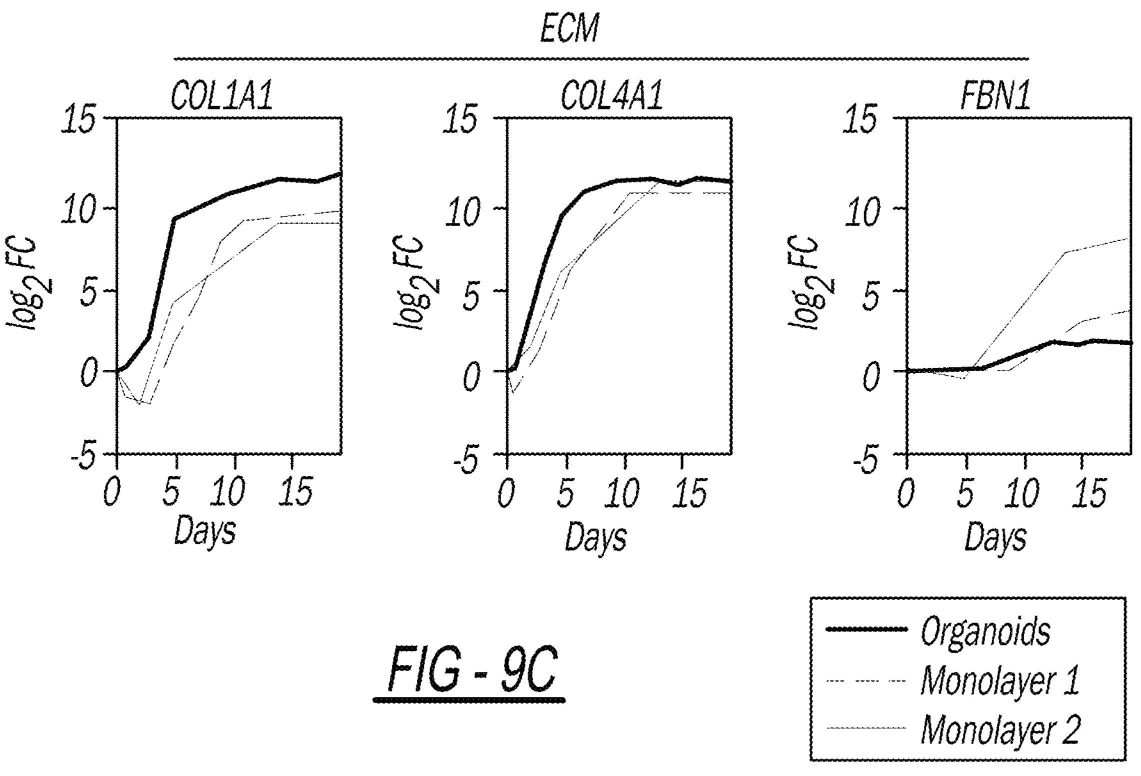
Figure 9E:
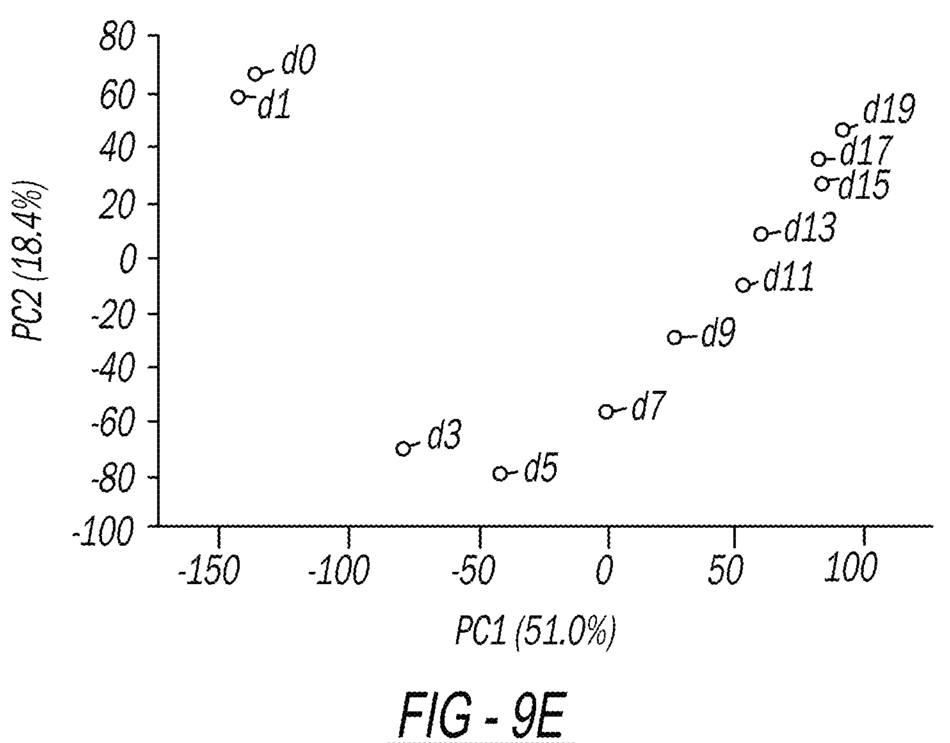
Figure 9D:
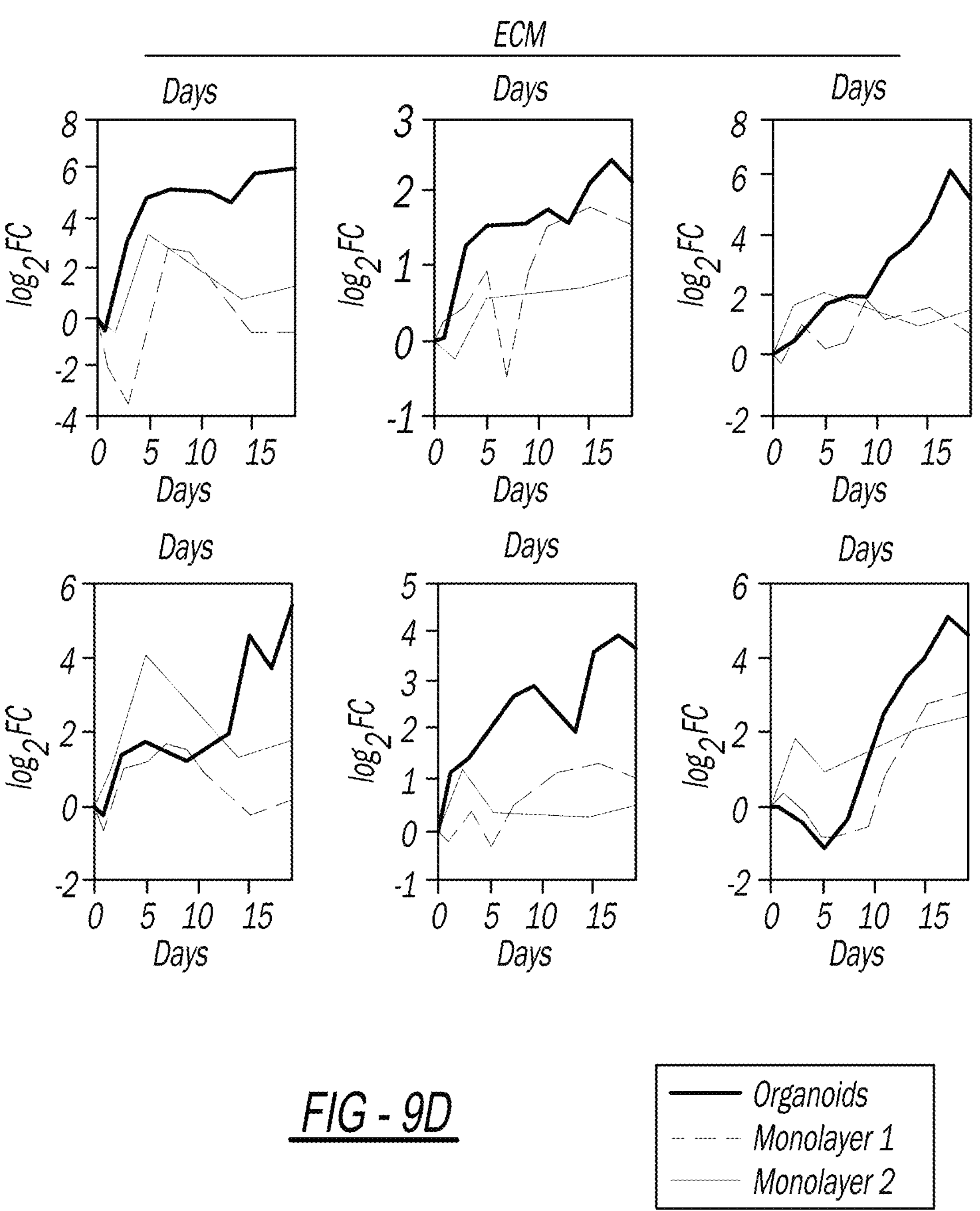

FIGS. 9A-9E show another transcriptomic analysis indicating that heart organoids prepared in accordance with various aspects of the current technology recapitulate multicell-type complexity, development, and maturation steps similar to embryonic fetal hearts. FIG. 9A shows a gene expression analysis indicating more FHF and SHF markers over the heart organoid differentiation process. FIG. 9B shows a gene expression analysis ($\log_2$ fold-change versus D0) for cardiac-specific cell-type populations in heart organoids, including (from top left to bottom right) endocardial cells, epicardial cells, endothelium, and cardiac fibroblasts. FIG. 9C shows a gene expression analysis ($\log_2$ fold-change versus D0) for cardiomyocyte markers. FIG. 9D shows a gene expression analysis ($\log_2$ fold-change versus D0) for ECM protein-coding genes that are present in cardiac tissue. FIG. 9E shows a principal component analysis of heart organoid differentiation over time.

Figure 10A:
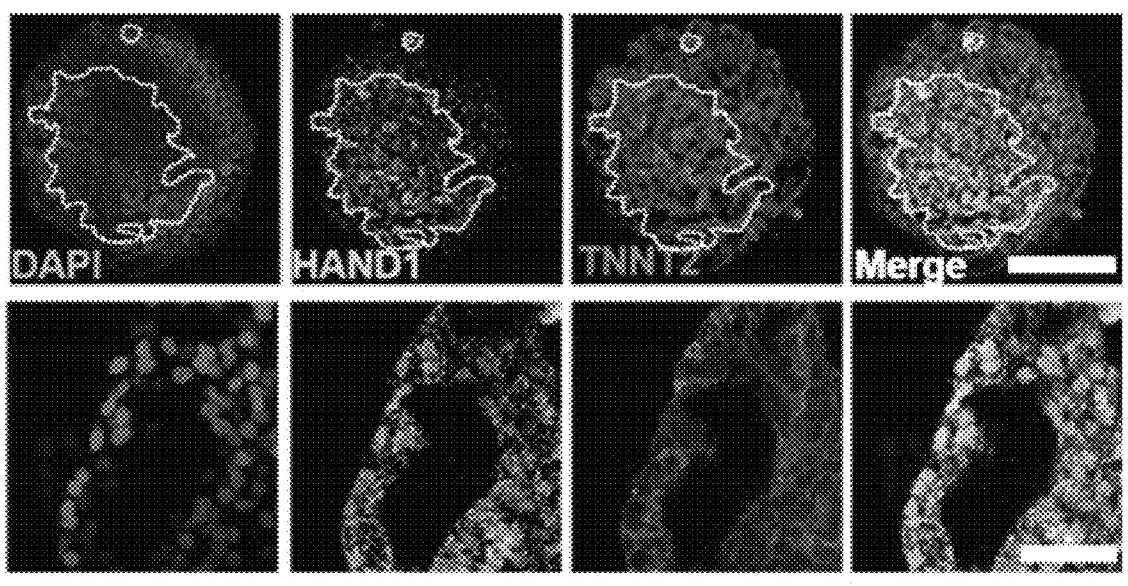
Figure 10B:
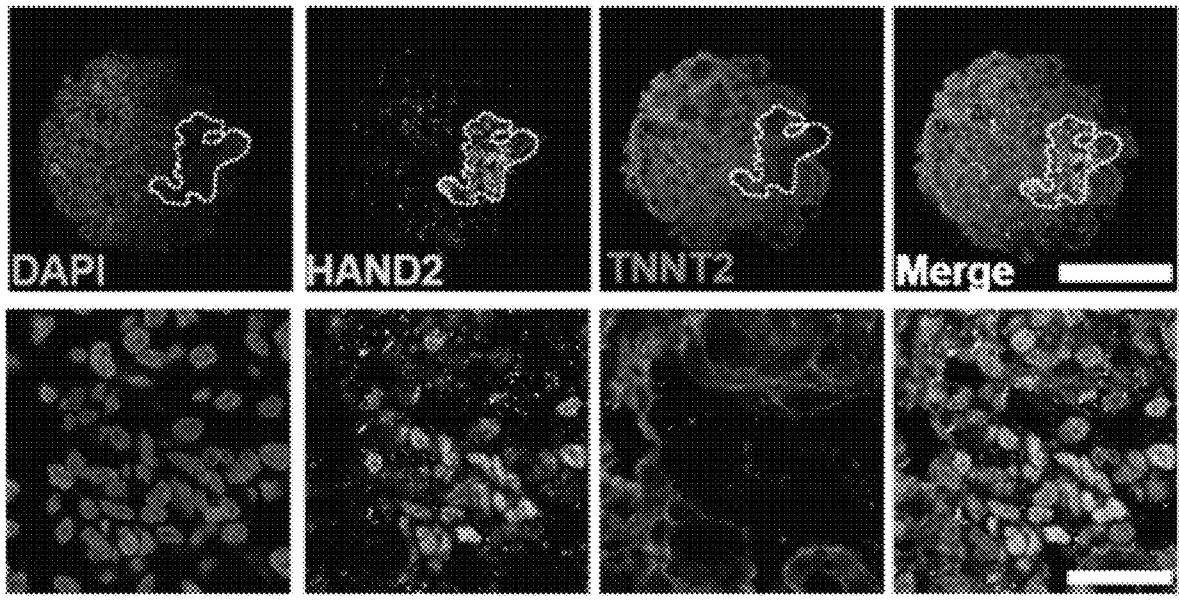

FIGS. 10A-10C are images showing heart field development and cardiomyocyte specification in hHOs prepared in accordance with various aspects of the current technology. Confocal immunofluorescent images of hHOs on day 8 of differentiation show robust HAND1 (FIG. 10A) and HAND2 (FIG. 10B) transcription factor expression (green), TNNT2 (red), and DAPI (blue) (scale bar: 500 μm, inset: 50 μm). FIG. 10C shows confocal immunofluorescent images of hHOs on day 15 containing well-differentiated ventricular (MYL2, green) and atrial regions (MYL7, red) and DAPI (blue) (scale bar: 500 μm, inset: 50 μm).

Figure 11A:
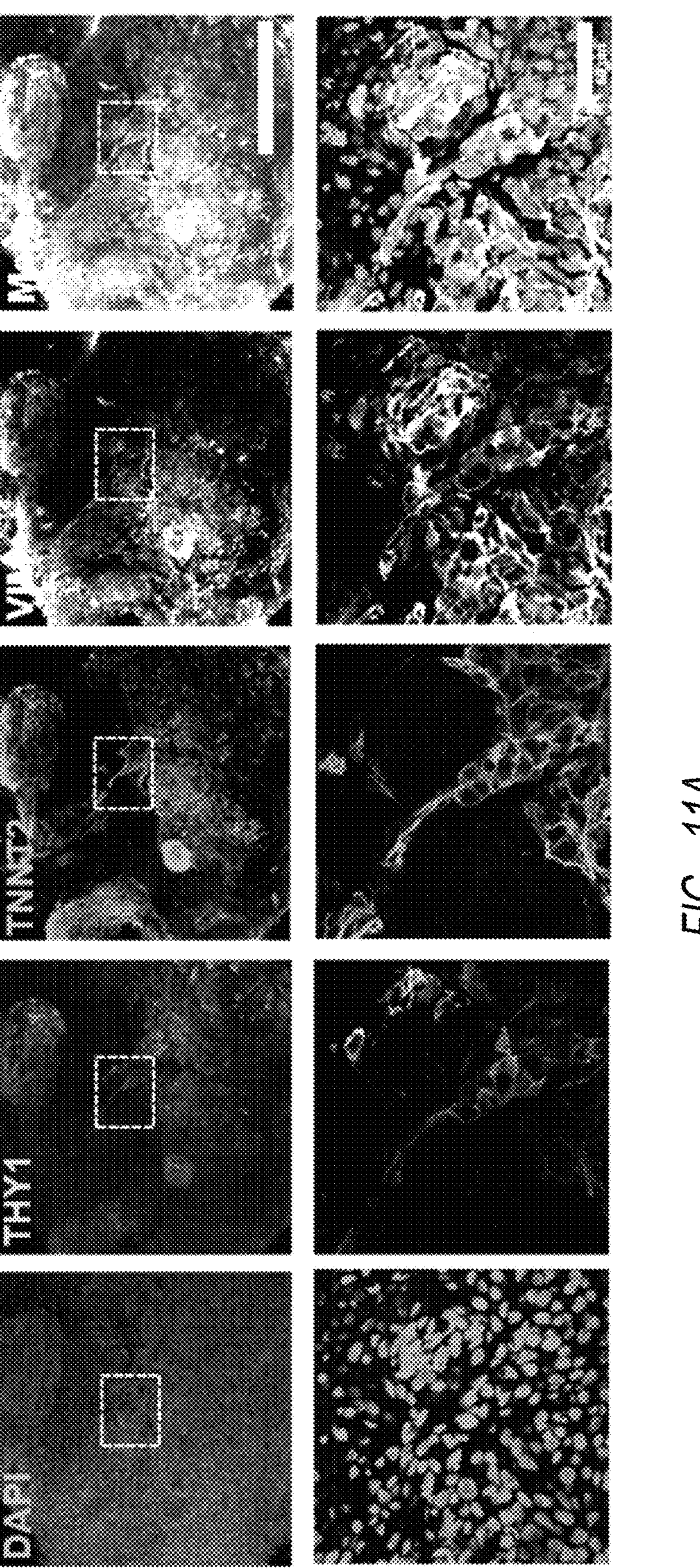
Figure 11D:
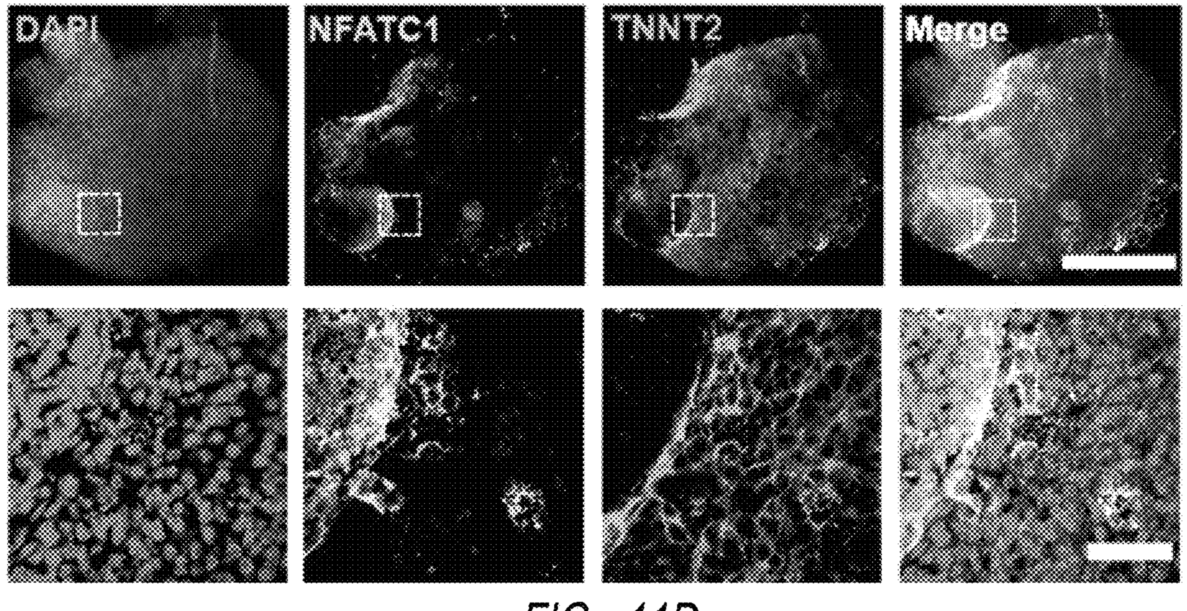
Figure 11E:
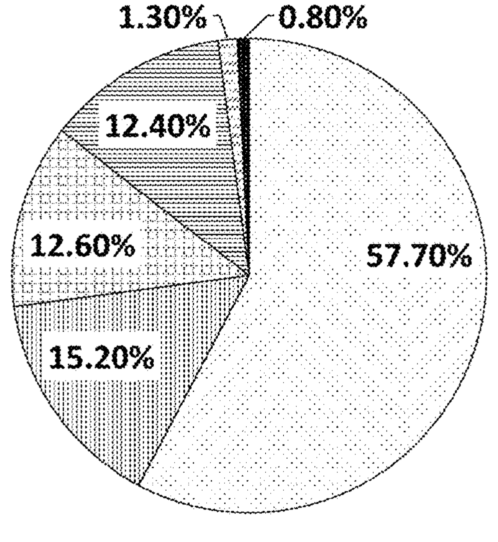

FIGS. 11A-11E provide data regarding cardiac cell lineage compositions of hHOs prepared in accordance with various aspects of the current technology. Immunofluorescence images are shown of various cell lineages composing the hHOs in FIGS. 11A-11D. FIG. 11A shows cardiac fibroblast markers THY1 (green) and VIMENTIN (white) present throughout the hHOs, TNNT2+ (red), and DAPI (blue) (scale bar: 500 μm, inset: 50 μm). FIG. 11B shows endothelial marker PECAM1 (green) indicating a defined network of vessels throughout the organoid and adjacent to TNNT2+(red) tissue and DAPI (blue) (scale bar: 500 μm). FIG. 11C shows a 60× magnification of PECAM1+ endothelial tissue in close proximity to TNNT2+ myocardial tissue (scale bar: 50 μm). FIG. 11D shows endocardial marker NFATC1 (green) highly expressed within microchambers of TNNT2+(red) tissue (scale bar: 500 μm, inset: 50 μm). FIG. 11E is a pie chart of the average cell composition in hHOs calculated as a percentage of the whole organoid area using ImageJ.

Figure 12A:
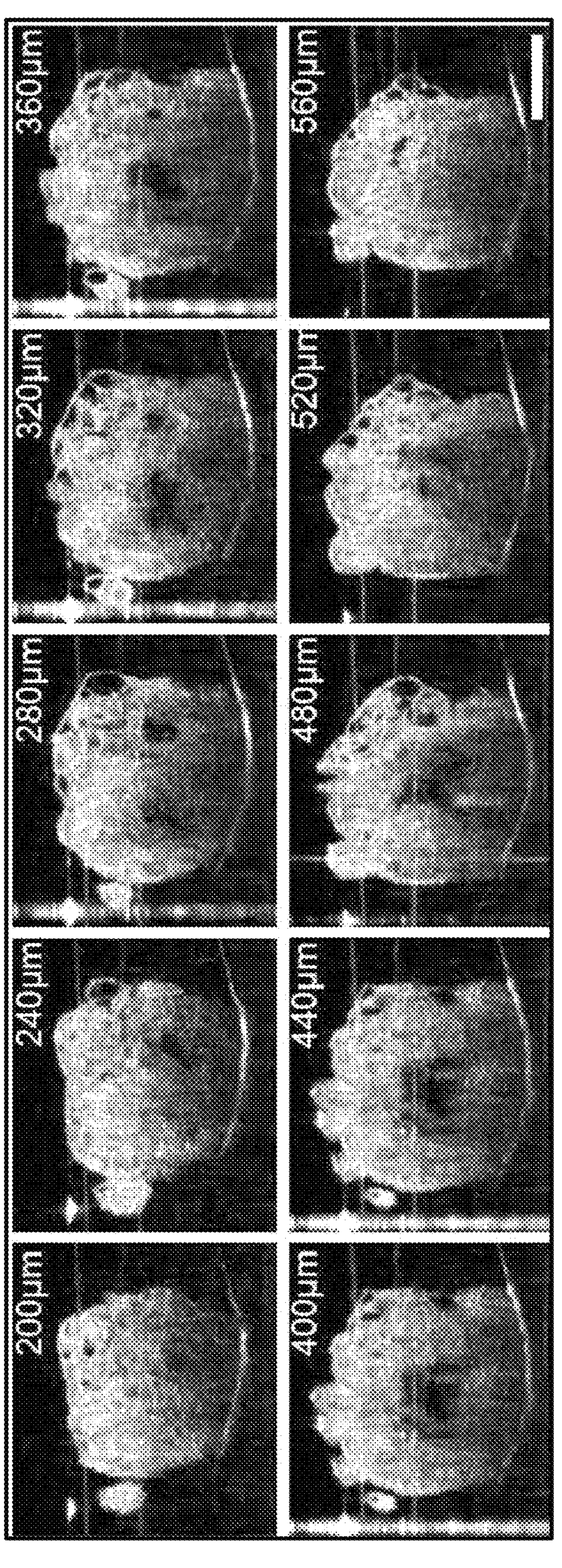
Figure 12B:
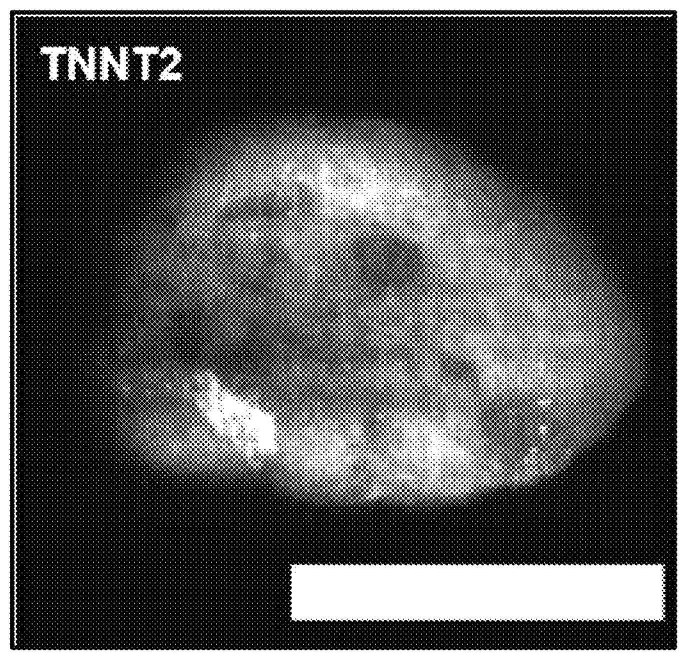
Figure 12C:
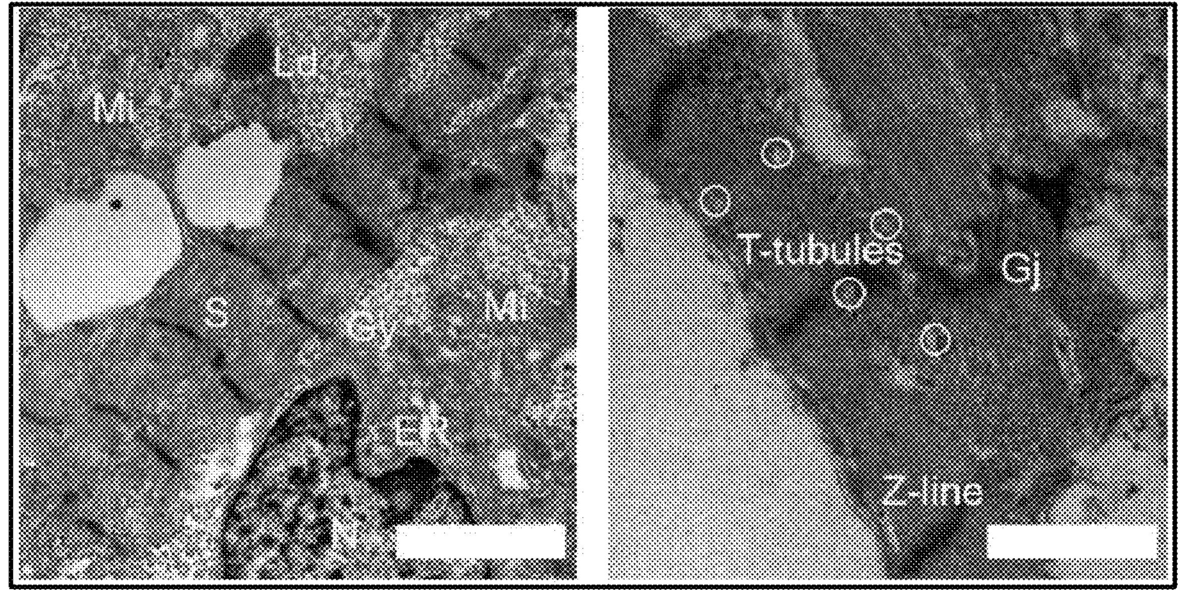
Figure 12D:
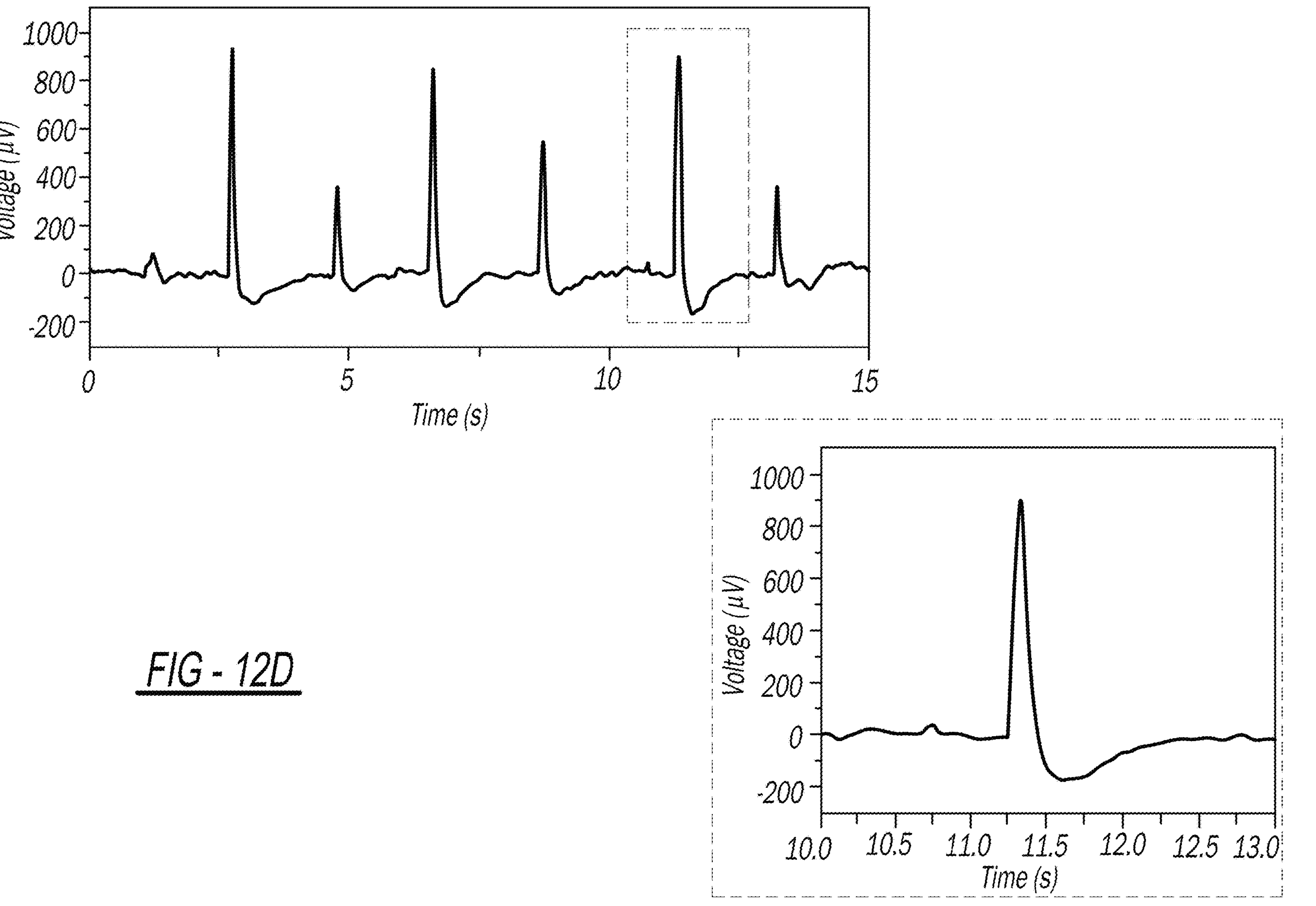

FIGS. 12A-12D provides data showing microchamber formation, ultrastructure, and electrophysiology of hHOs prepared in accordance with various aspects of the current technology. FIG. 12A shows optical coherence tomography (OCT) images showing cross-sections through an organoid that reveal microchambers (scale bar: 500 μm). FIG. 12B shows a light-sheet image of an hHO stained for TNNT2 with an AF488 secondary antibody that reveals chamber structures (scale bar: 500 μm). FIG. 12C shows transmission electron microscopy (TEM) images of hHOs showing endoplasmic reticulum (ER), gap junctions (Gj), glycogen granules (Gy), lipid droplets (Ld), mitochondria (Mi), nuclei (N), and sarcomeres (S) (left scale bar: 2 μm, right scale bar: 1 μm). FIG. 12D shows electrophysiology recordings of an organoid on a microelectrode array (MEA) over 15 seconds (left) and a representative action potential wave (right).

Figure 13A:
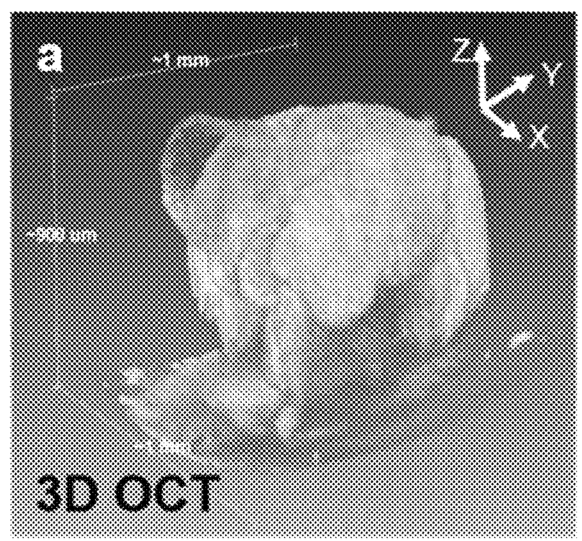
Figure 13B:
Figure 13D:
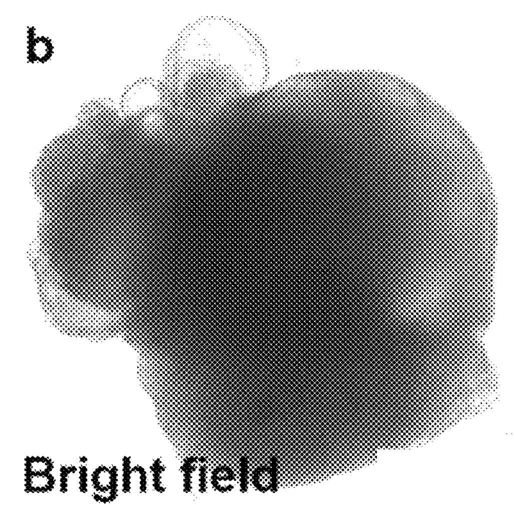
Figure 13D:
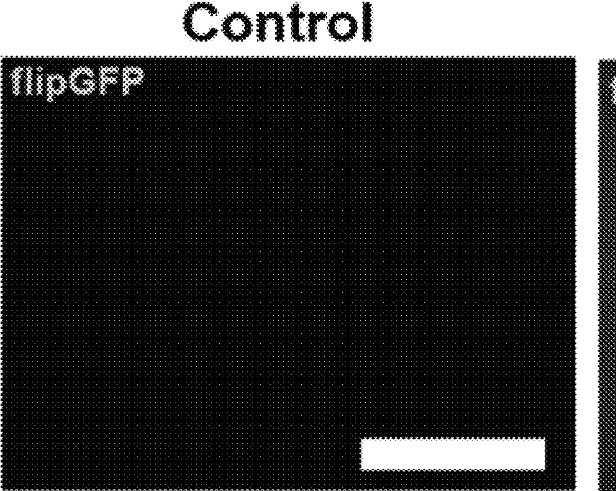
Figure 13D:
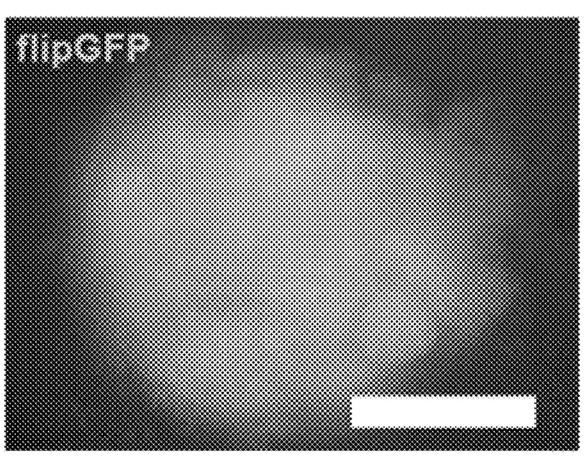
Figure 13C:
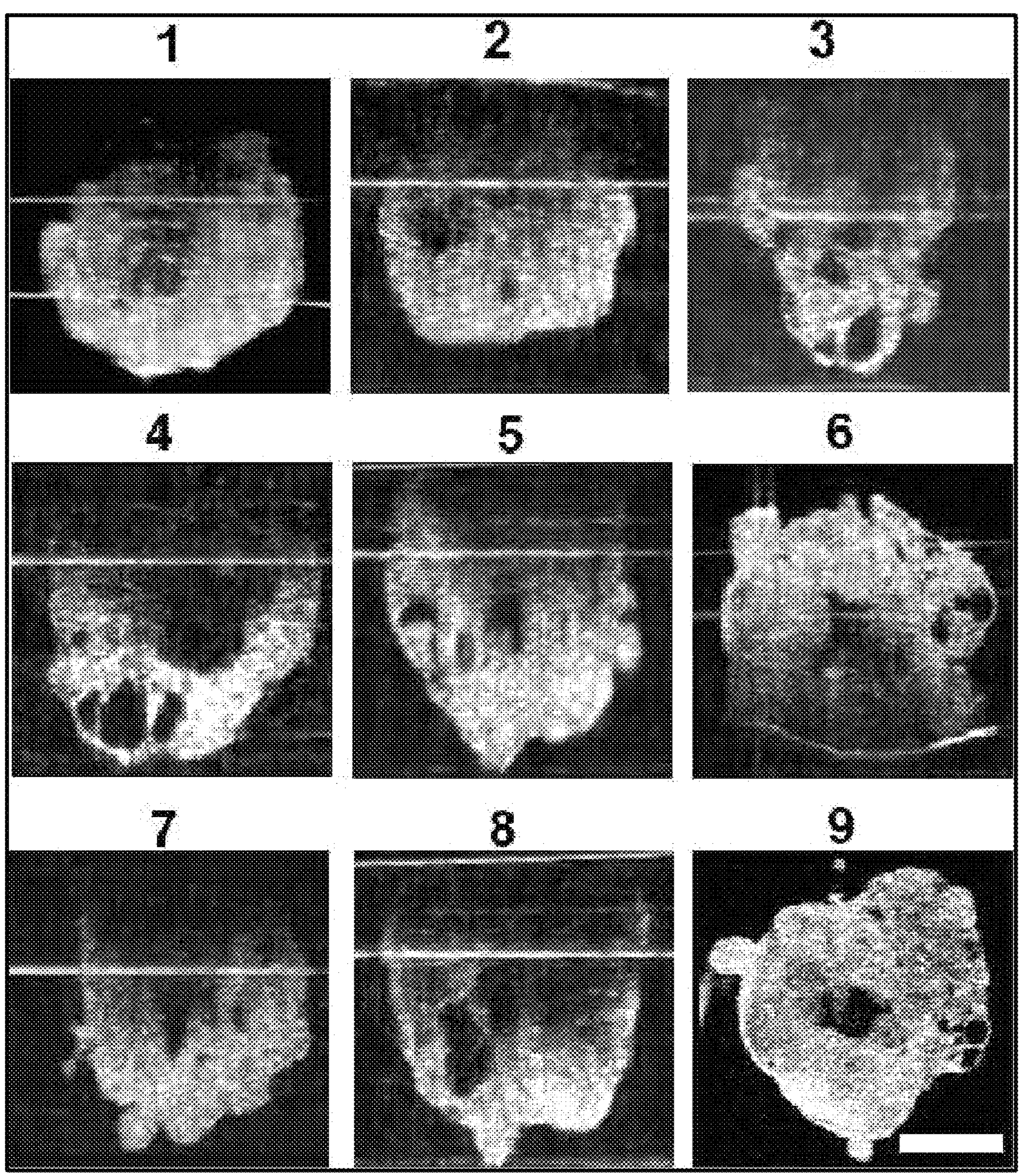

FIGS. 13A-13D provide data associated with hHOs prepared in accordance with various aspects of the current technology. FIG. 13A shows a three-dimensional reconstruction of OCT images, and FIG. 13B shows a brightfield image of an hHO. FIG. 13C provides OCT images showing cross-sections of the centers of nine different organoids that reveal central chambers (scale bar: 500 μm). FIG. 13D provides immunofluorescence images of organoids derived from a FlipGFP transgenic iPSC-L1 line showing no apoptosis in control hHOs (left) and high apoptosis in hHOs treated with 5 μM doxorubicin (DOX) (right) (scale bar: 500 μm).

Figure 14:
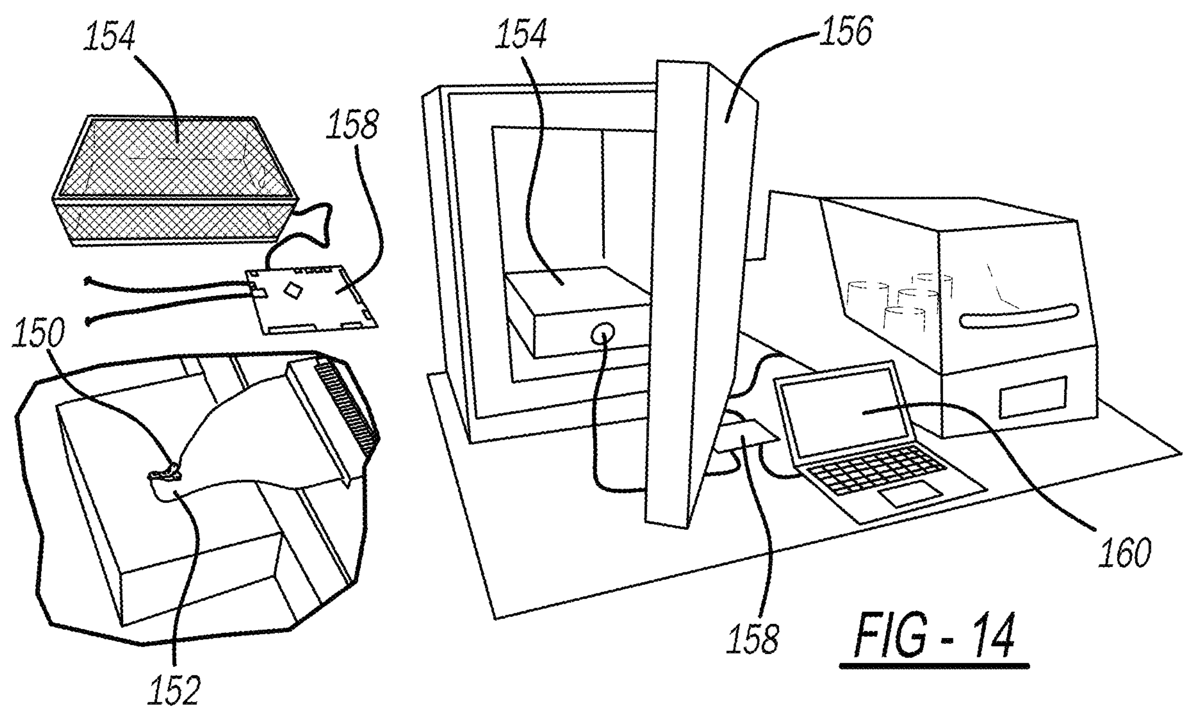

FIG. 14 is an illustration of a MEA recording system showing the gold electrode array in a polydimethylsiloxane (PDMS) chamber where a heart organoid of the current technology is placed within a Faraday cage inside an incubator.

Figure 15A:
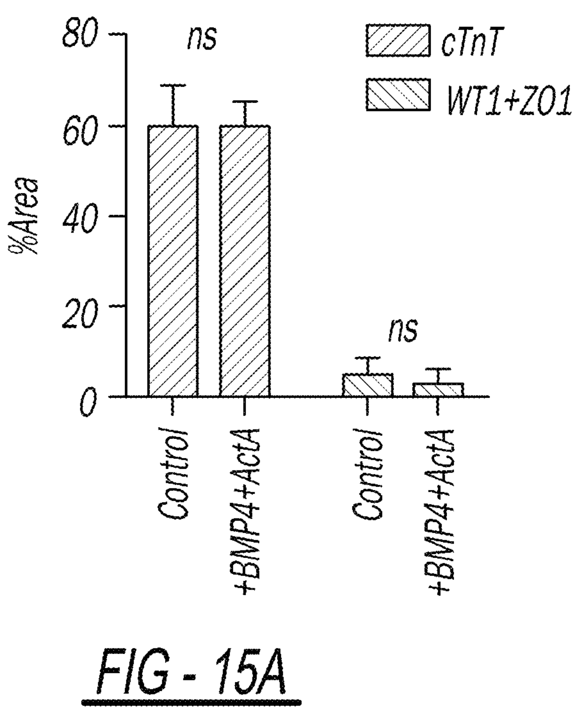
Figure 15B:
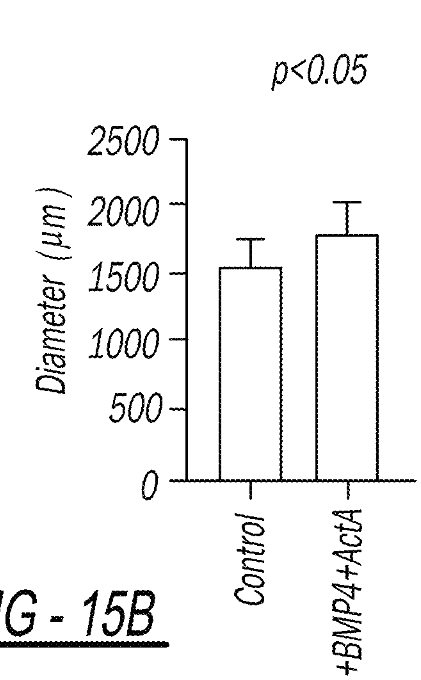
Figure 15C:
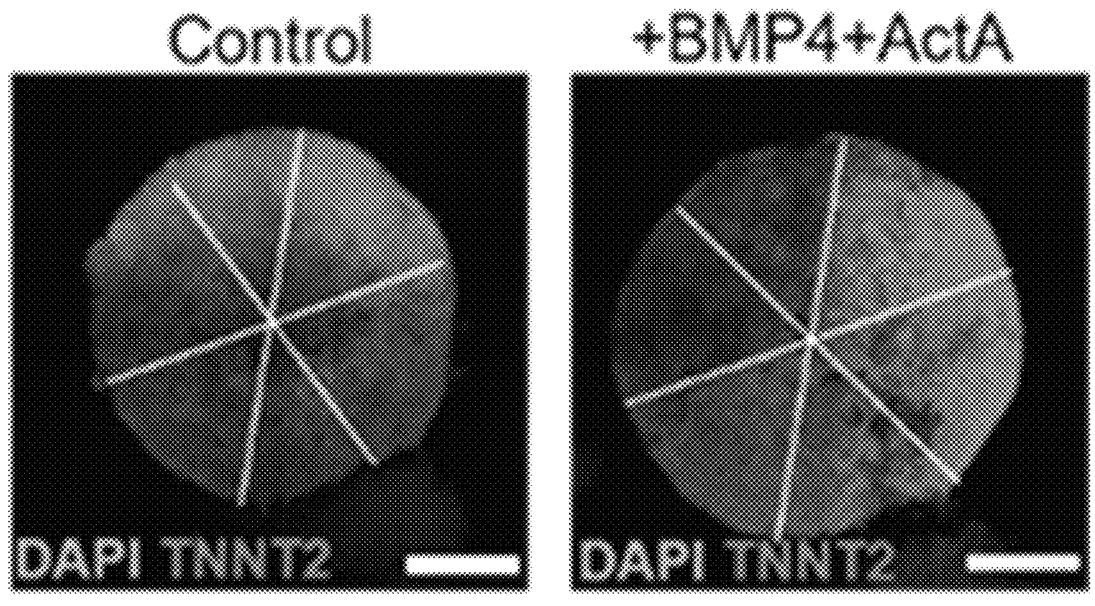
Figure 15G:
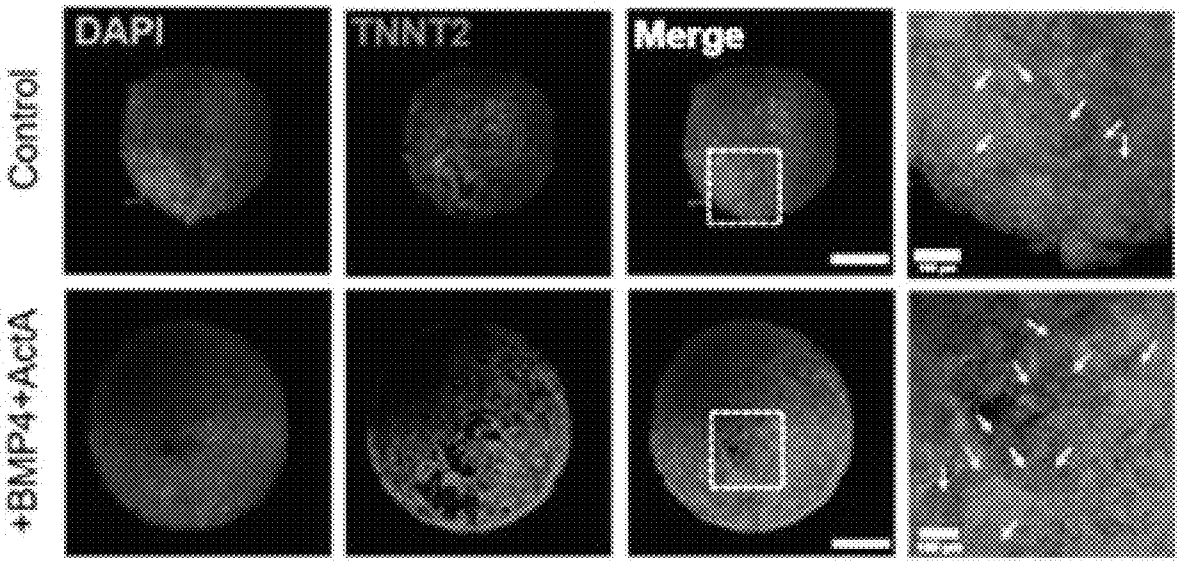
Figures 15D, 15E, 15F:
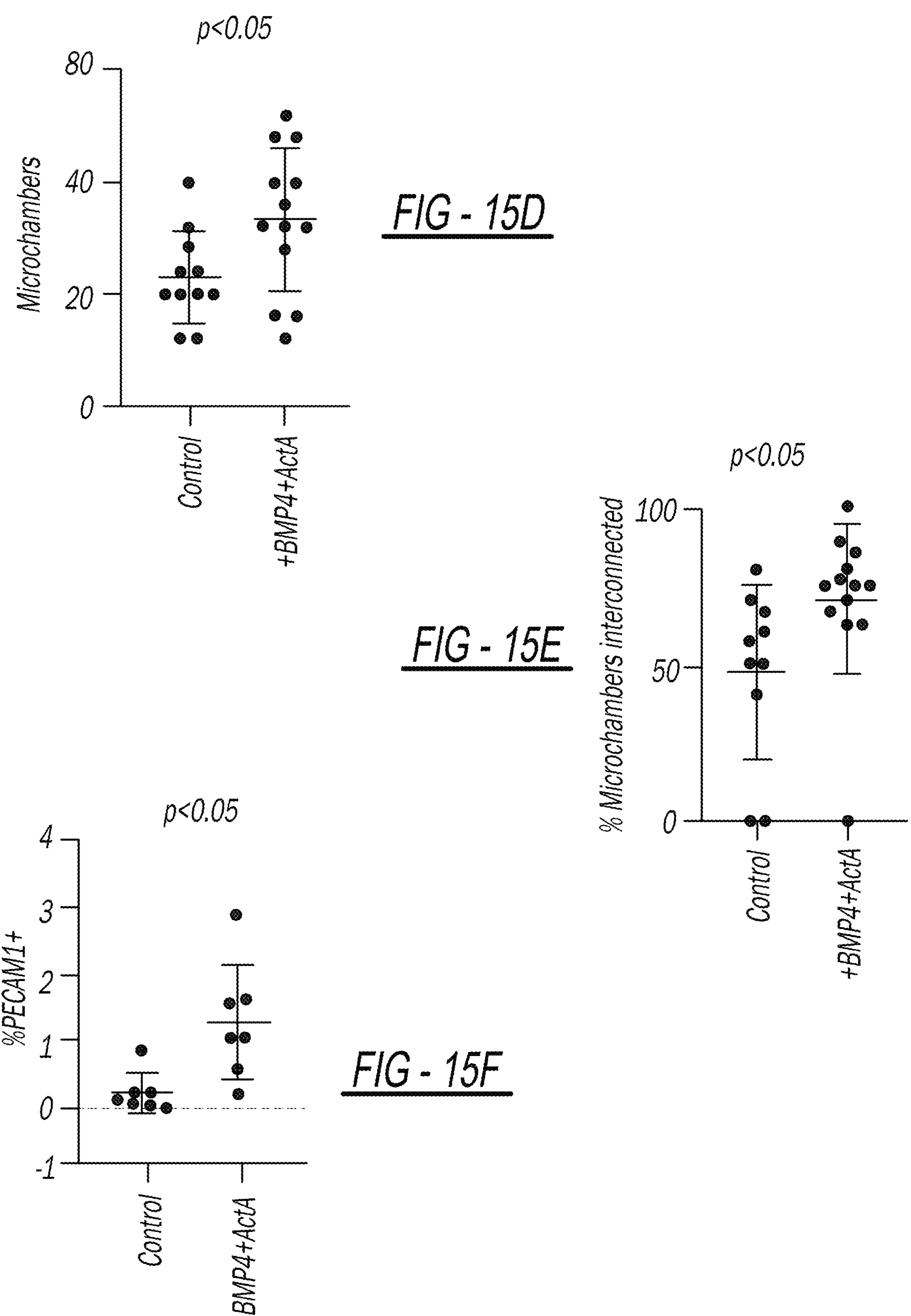
Figure 15H:
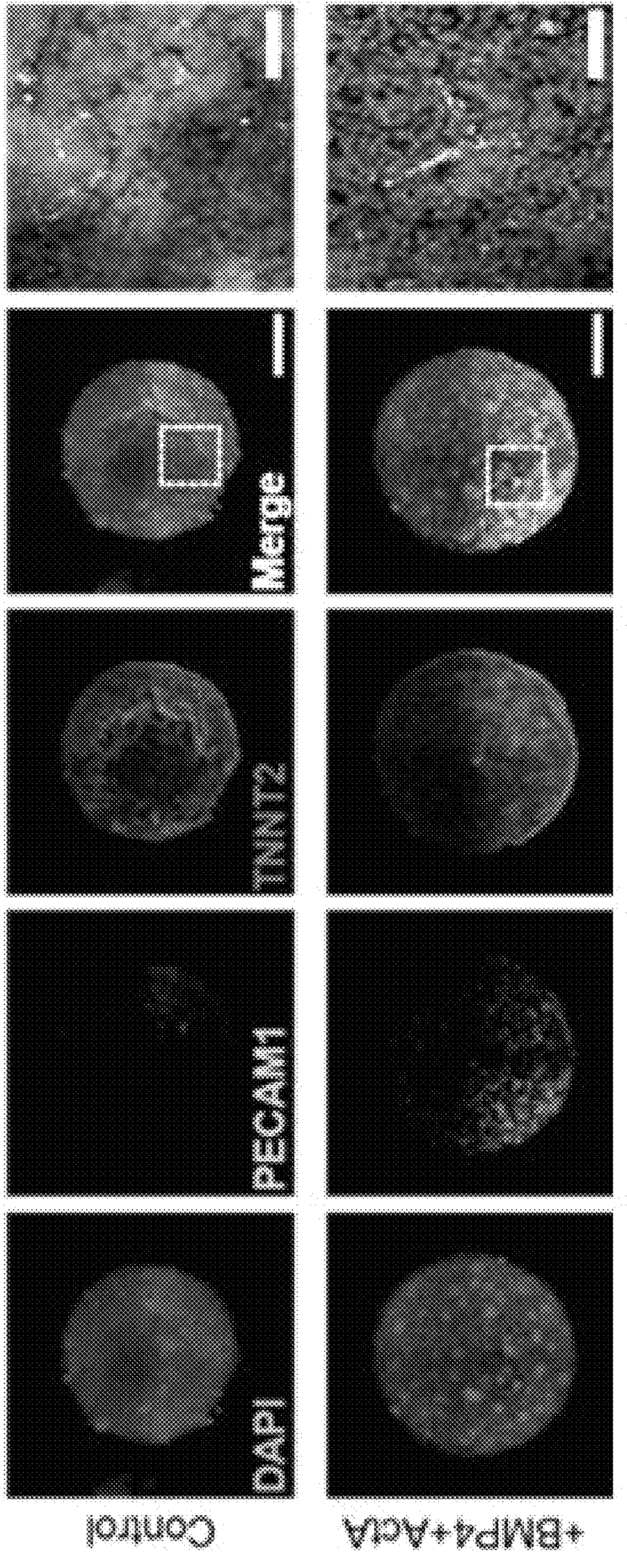

FIGS. 15A-15H provide data showing the effects of bone morphogenetic protein 4 (BMP4) and activin A (ActA) on cardiac differentiation and development in regard to hHOs prepared in accordance with various aspects of the current technology. All of FIGS. 15A-15H compare hHOs differentiated with CHIR alone (control) and with CHIR+BMP4+ActA (treated). FIG. 15A is a graph showing the area of cardiomyocyte and epicardial positive regions as a percentage of the total organoid area, and FIG. 15B is a graph showing organoid diameter (n=8 per condition). FIG. 15C provides dashed lines showing the diameter of a control (left) and treated (right) organoid averaged to determine the diameter. FIG. 15D shows the number of microchambers in TNNT2+ areas, and FIG. 15E shows the interconnectivity of microchambers measured by the separation of microchambers by thin TNNT2+ filaments or by thin channels showing clear connection. N=12 per condition in FIGS. 15D-15E. FIG. 15F shows the amount of PECAM1+ tissue as a percentage of the total organoid area (measured using Max-Entropy threshold on ImageJ and analyzing all particles of 25 $\mu m^2$ to avoid small speckles, n=7 per condition). FIG. 15G shows immunofluorescence images of hHOs showing interconnected microchambers (yellow arrows), TNNT2+ filaments (white arrows), and channels connecting micro-chambers (green arrows); DAPI (blue); and TNNT2 (red) (scale bar: 500 μm, inset: 100 μm). FIG. 15H shows immunofluorescence images of hHOs showing DAPI (blue), PECAM1+ tissue (green), and TNNT2+ tissue (red) (scale bar: 500 μm, inset: 50 μm). (Value=mean±s.d., two-tailed, unpaired t-test.)

Figure 16A:
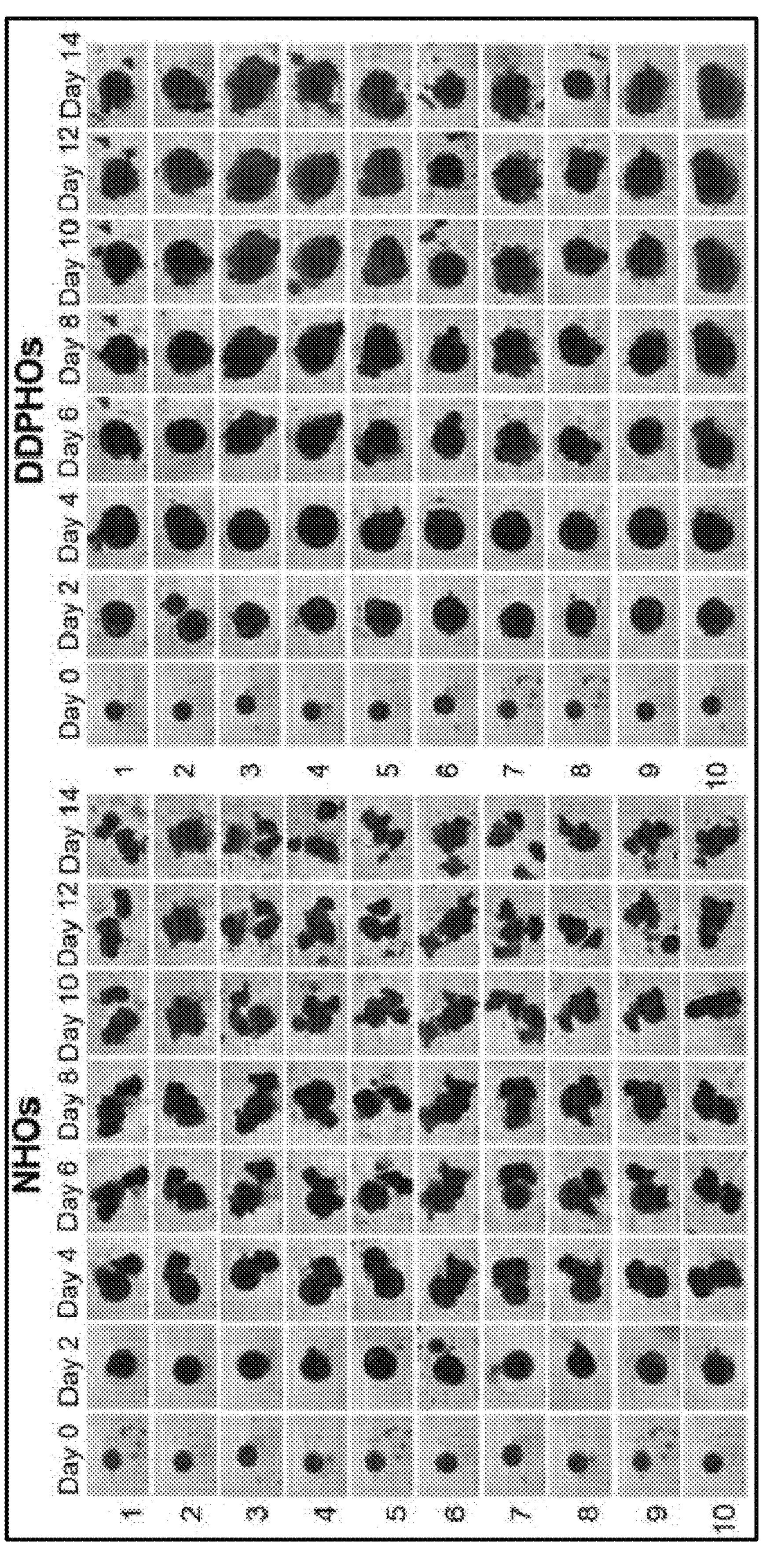
Figures 16B, 16C:
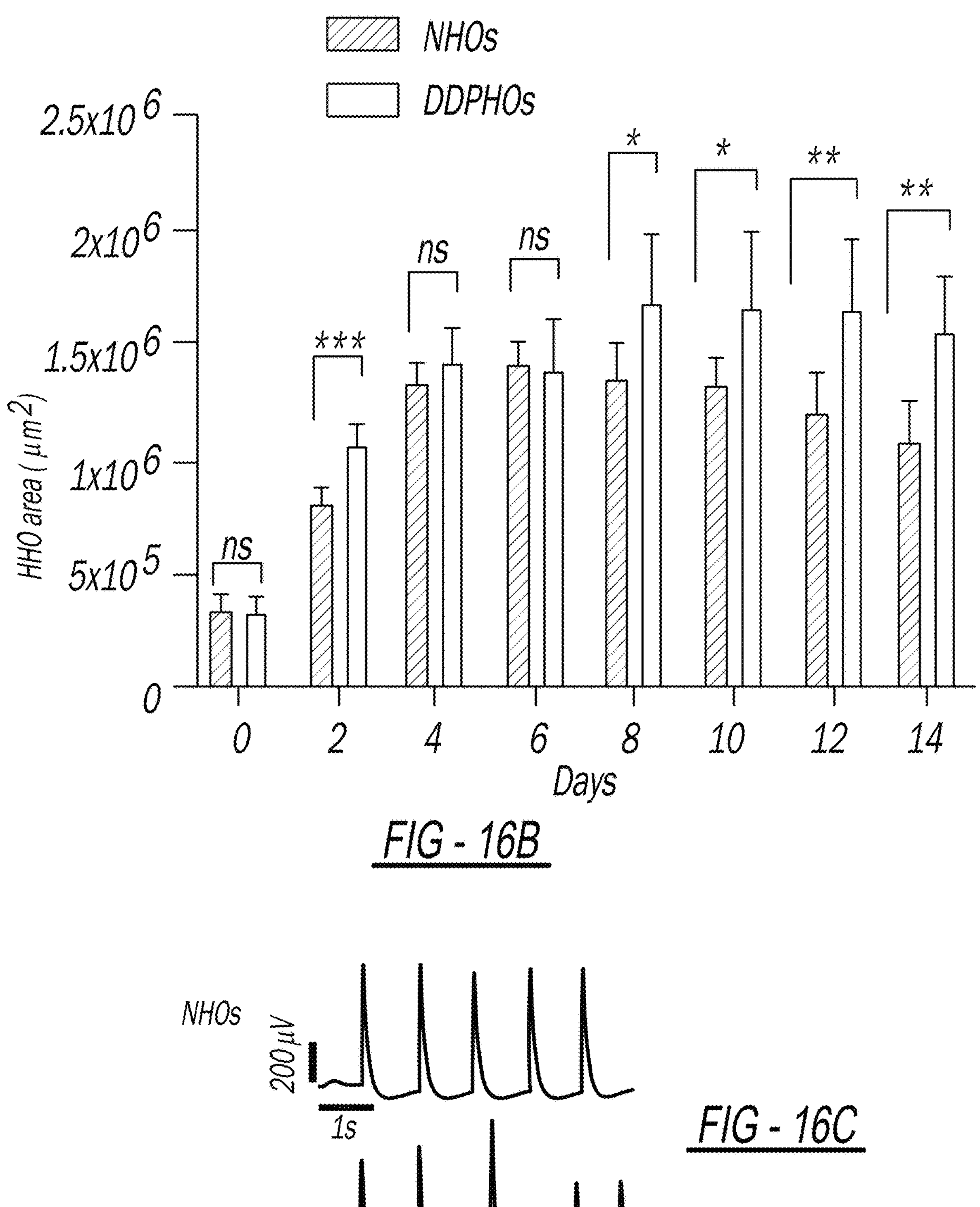
Figure 16D:
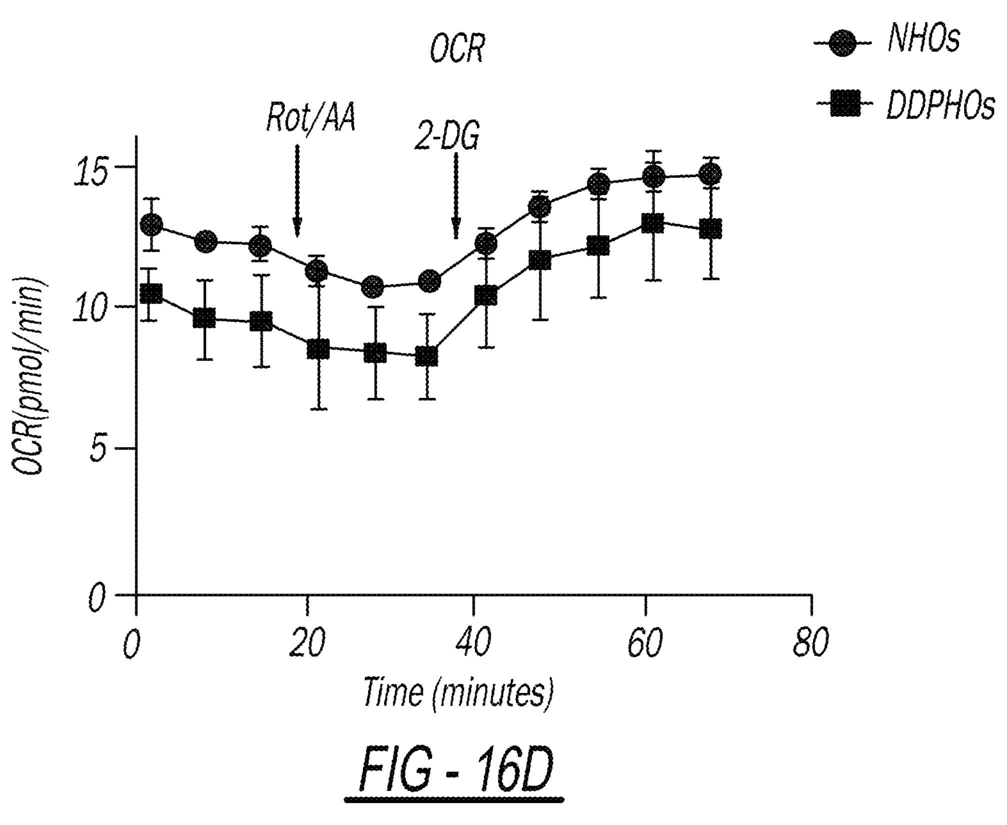
Figure 16E:
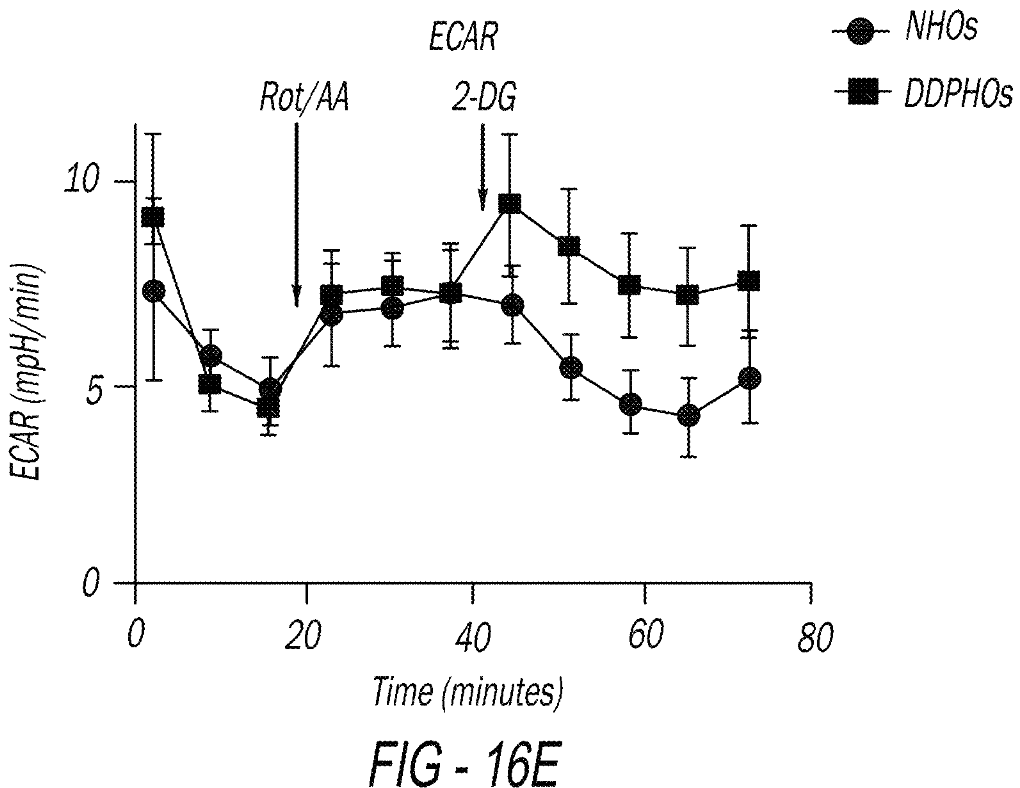
Figure 16F:
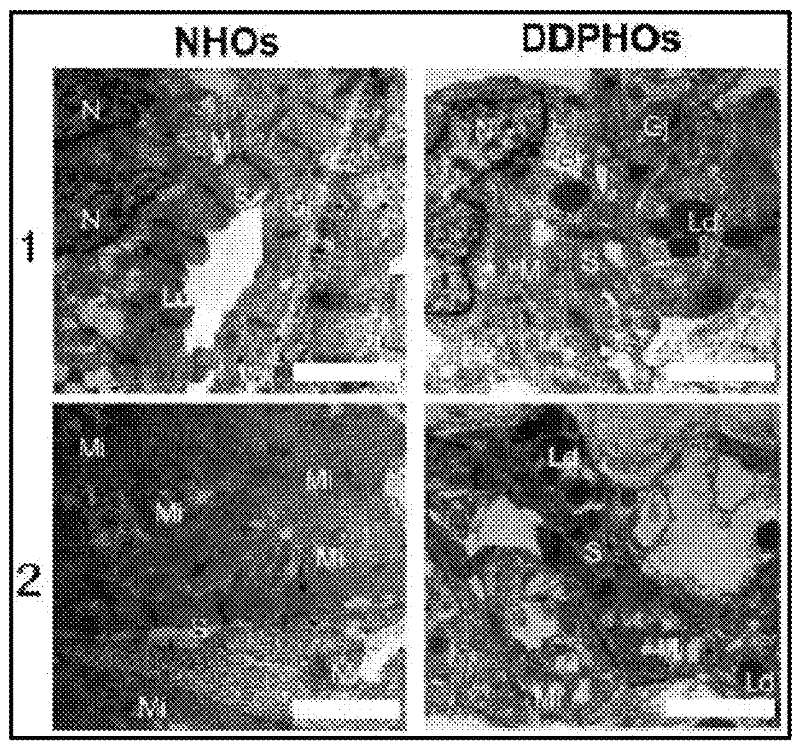
Figure 16G:
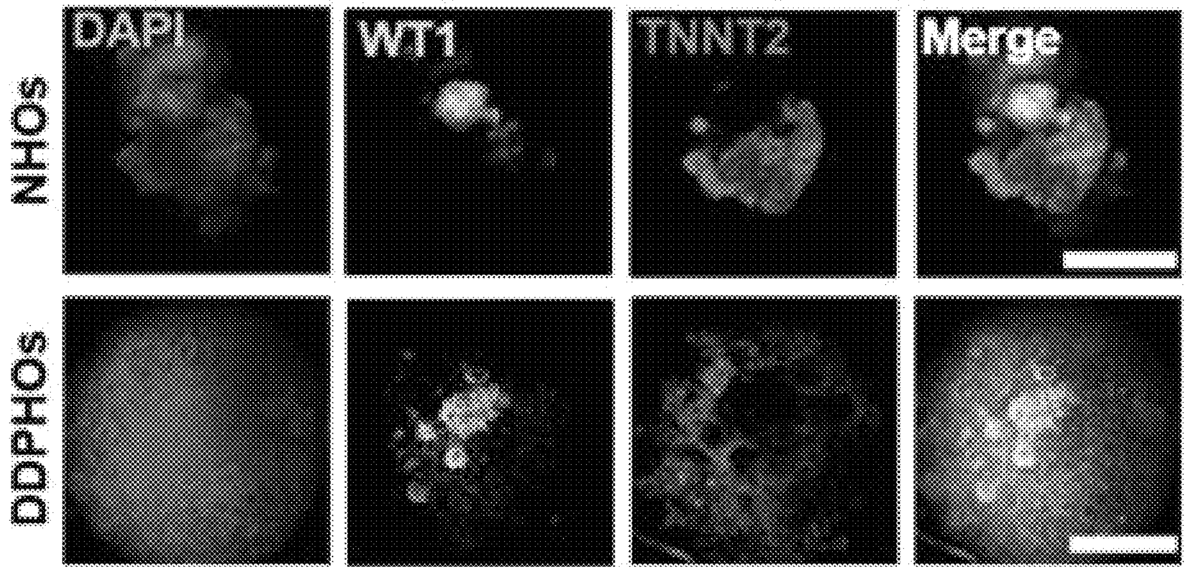
Figure 16H:
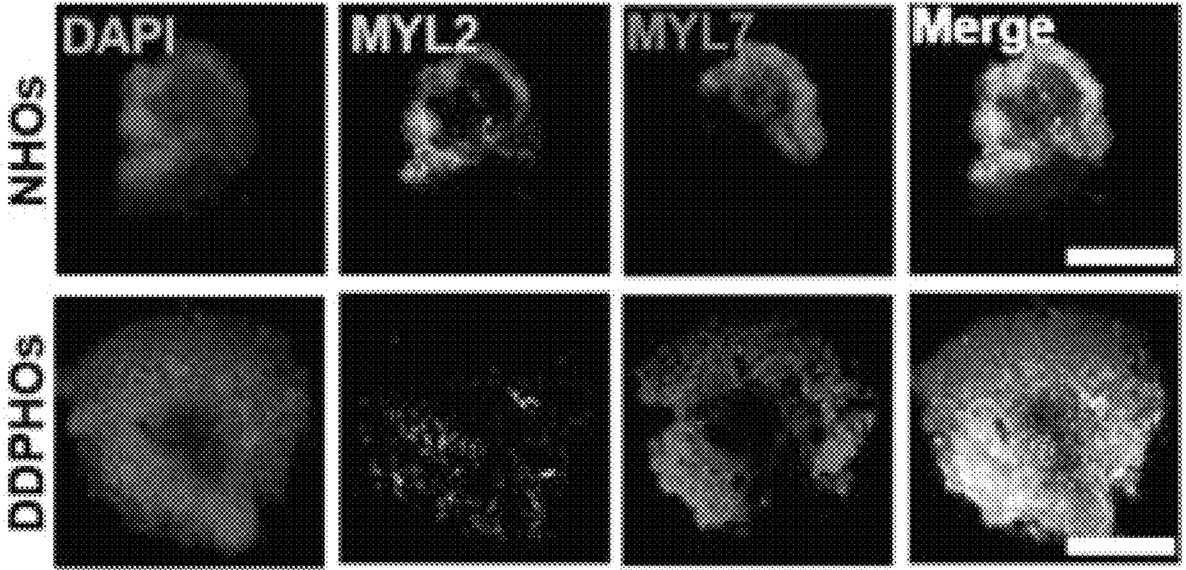

FIGS. 16A-16H provide data showing hHOs prepared in accordance with various aspects of the current technology faithfully recapitulate hallmarks of diabetes during pregnancy (DDP)-induced CHD. FIG. 16A shows brightfield images following the development of ten hHOs under normal glycemic conditions (NHOs, left) and under diabetic conditions (DDPHOs, right) over two weeks of differentiation. FIG. 16B shows the areas of hHOs in the first two weeks of differentiation (mean±s.d.; n=12; two-way ANOVA Sidak's multiple comparisons test). FIG. 16C shows an electrophysiology analysis performed on NHOs and DDPHOs at 15 days; arrows indicate arrhythmic events. FIG. 16D shows a seahorse analysis for oxygen consumption rate (OCR), and FIG. 16E shows extracellular acidification rate (ECAR) of normal and diabetic hHOs. FIG. 16F is an ultrastructural analysis by TEM of NHOs and DDPHOs showing endoplasmic reticulum (ER), gap junctions (Gj), glycogen granules (Gy), lipid droplets (Ld), mitochondria (Mi), nuclei (N), and sarcomeres (S); FIG. 16G shows confocal immunofluorescent images at differentiation day 15 for cardiac (TNNT2) and epicardial (WT1) formation; and FIG. 16H shows confocal imaging for ventricular (MYL2) and atrial (MYL7) chamber formation under normal and diabetic-like conditions (scale bar: 500 μm).

Figure 17A:
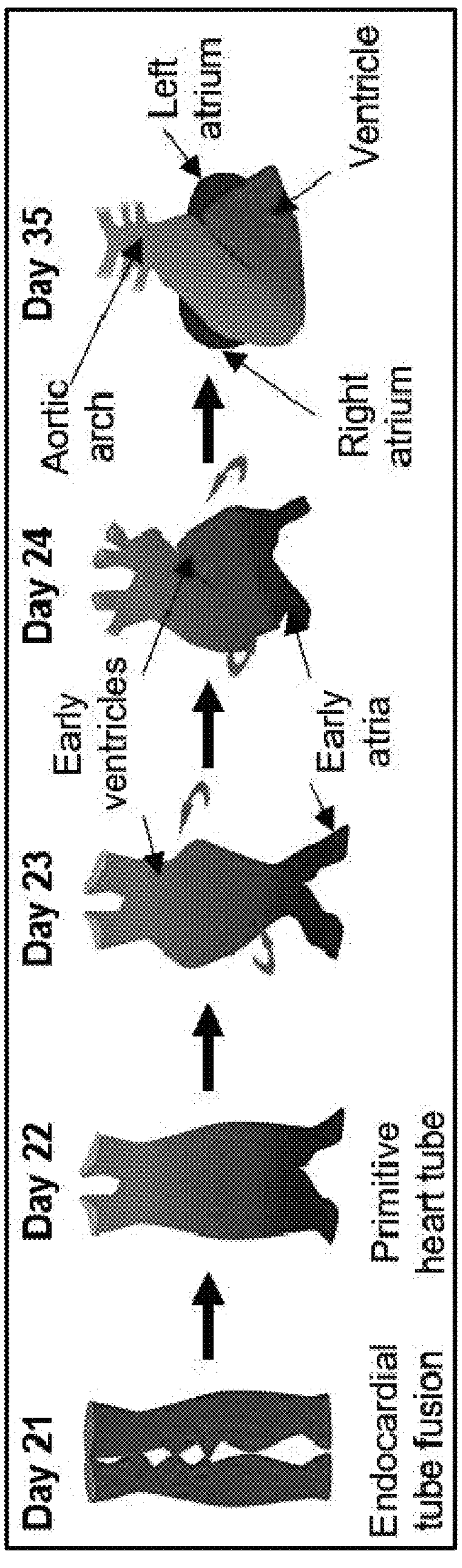
Figure 17B:
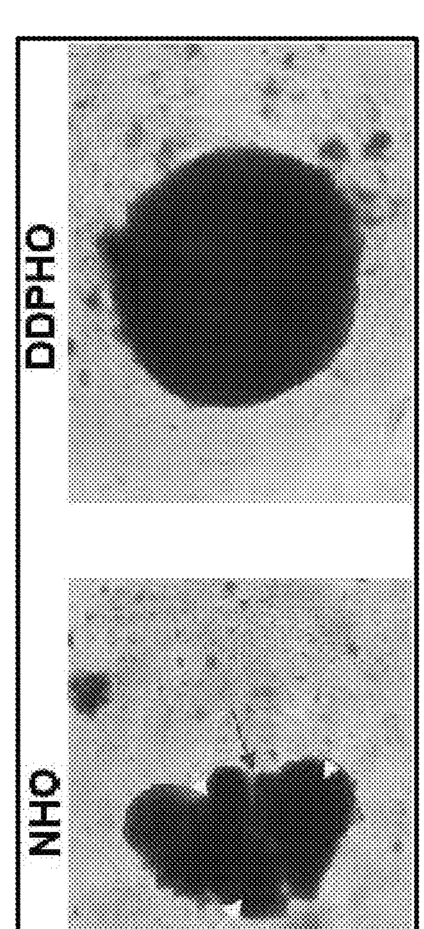
Figure 17C:
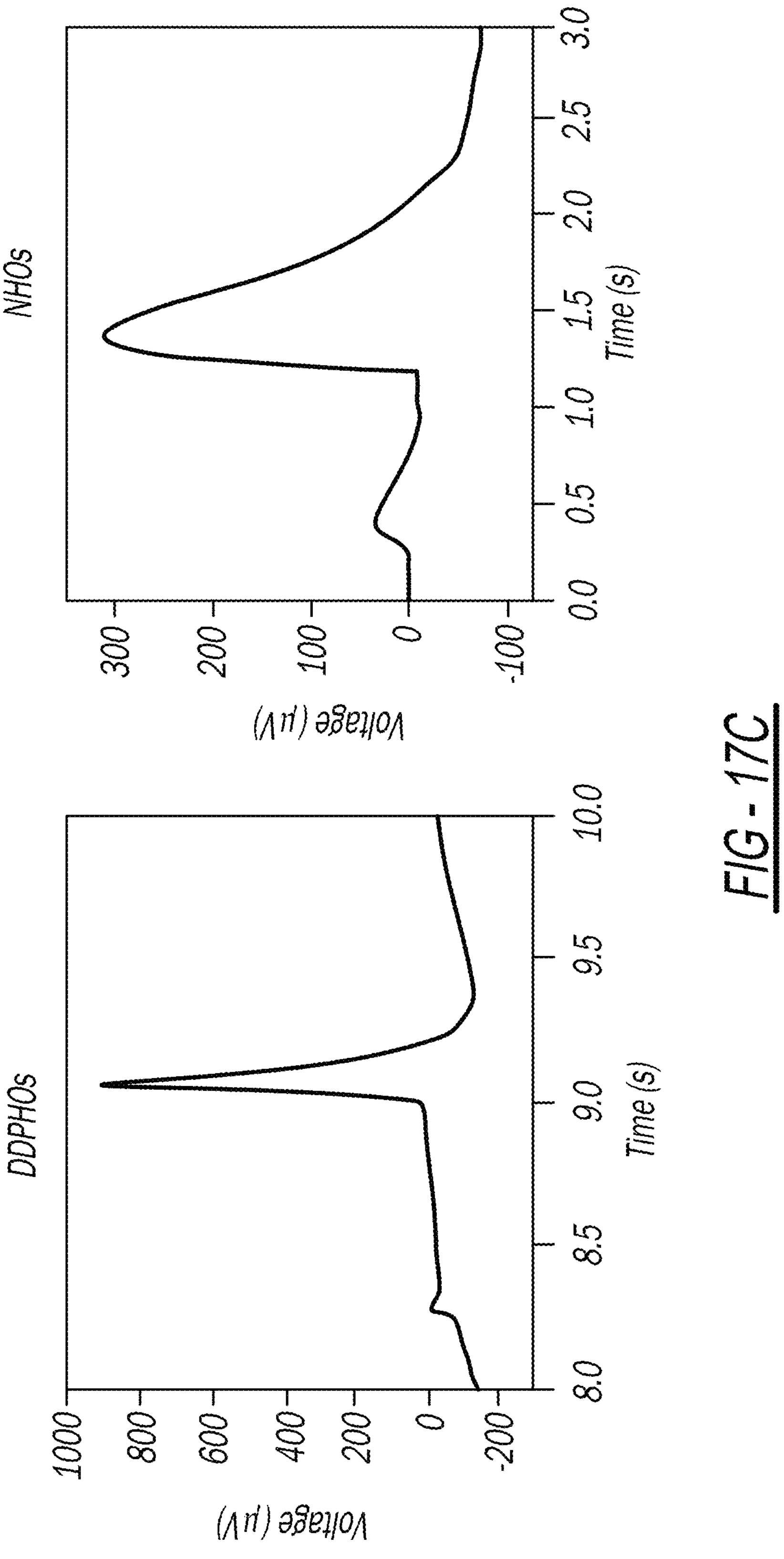
Figure 17D:
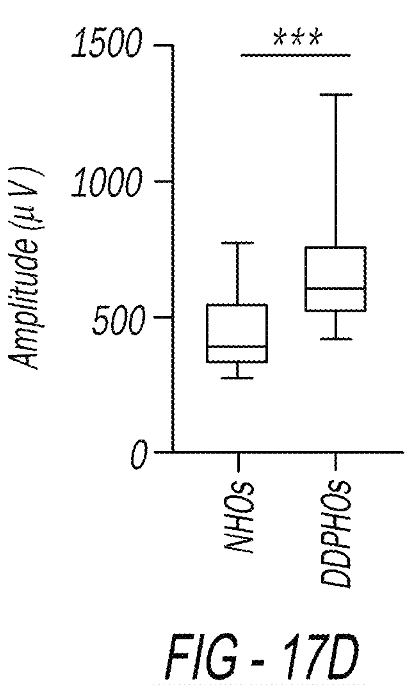
Figure 17E:
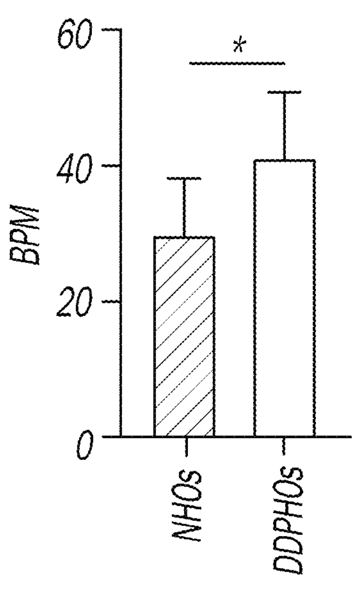
Figure 17F:
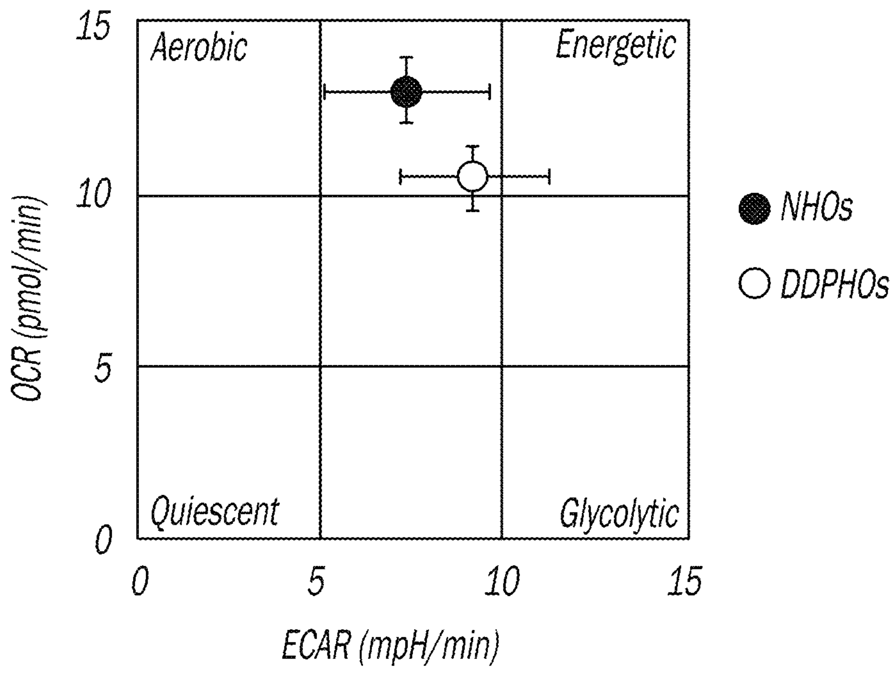

FIGS. 17A-17F provide data showing hHOs prepared in accordance with the current technology model functional features in healthy and diabetic conditions. FIG. 17A shows a schematic diagram of heart tube formation and looping into the four chambers of the heart. FIG. 17B shows bright-field images of NHO and DDPHO at day 15 showing segmentation (red arrow) and separate heart regions resembling early heart structures (yellow arrows). FIG. 17C shows representative MEA electrophysiology detail of normal versus diabetic organoids. FIG. 17D shows the amplitude magnitude in μV of action potentials in normal and diabetic hHOs (n>12 over three replicates per condition; unpaired t-test, *p<0.001). FIG. 17**E shows the beating frequency in beats per minute (BPM) in normal and diabetic organoids as recorded by MEA (mean±s.d., n>5 organoids; unpaired t-test, *p<0.05). FIG. 17F shows a seahorse energy map of normal and diabetic-like organoids (mean±s.d.).

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first,"

"second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges. As referred to herein, ranges are, unless specified otherwise, inclusive of endpoints and include disclosure of all distinct values and further divided ranges within the entire range. Thus, for example, a range of "from A to B" or "from about A to about B" is inclusive of A and B.

Example embodiments will now be described more fully with reference to the accompanying drawings.

The current technology provides a small molecule-based method for creating highly complex and physiologically relevant heart organoids, including hHOs, using hPSCs by manipulating cardiac developmental programs. The method relies mainly on three sequential Wnt modulation steps (activation/inhibition/activation) at specific time points on suspension embryoid bodies and produces significant heart-like structures in terms of structure, organization, functionality, cardiac cell-type complexity, ECM composition, and vascularization. Additionally, the method is less expensive compared to growth factor-based approaches and relatively simple in terms of procedure. The method is also automatable, scalable, and amenable to high-content/high-throughput pharmacological screenings. The current technology also provides hHOs generated from the method. The hHOs can be used to model various conditions and diseases, such as the effects of DDP on developing embryonic hearts, and to identify therapeutic targets.

Figure 1:
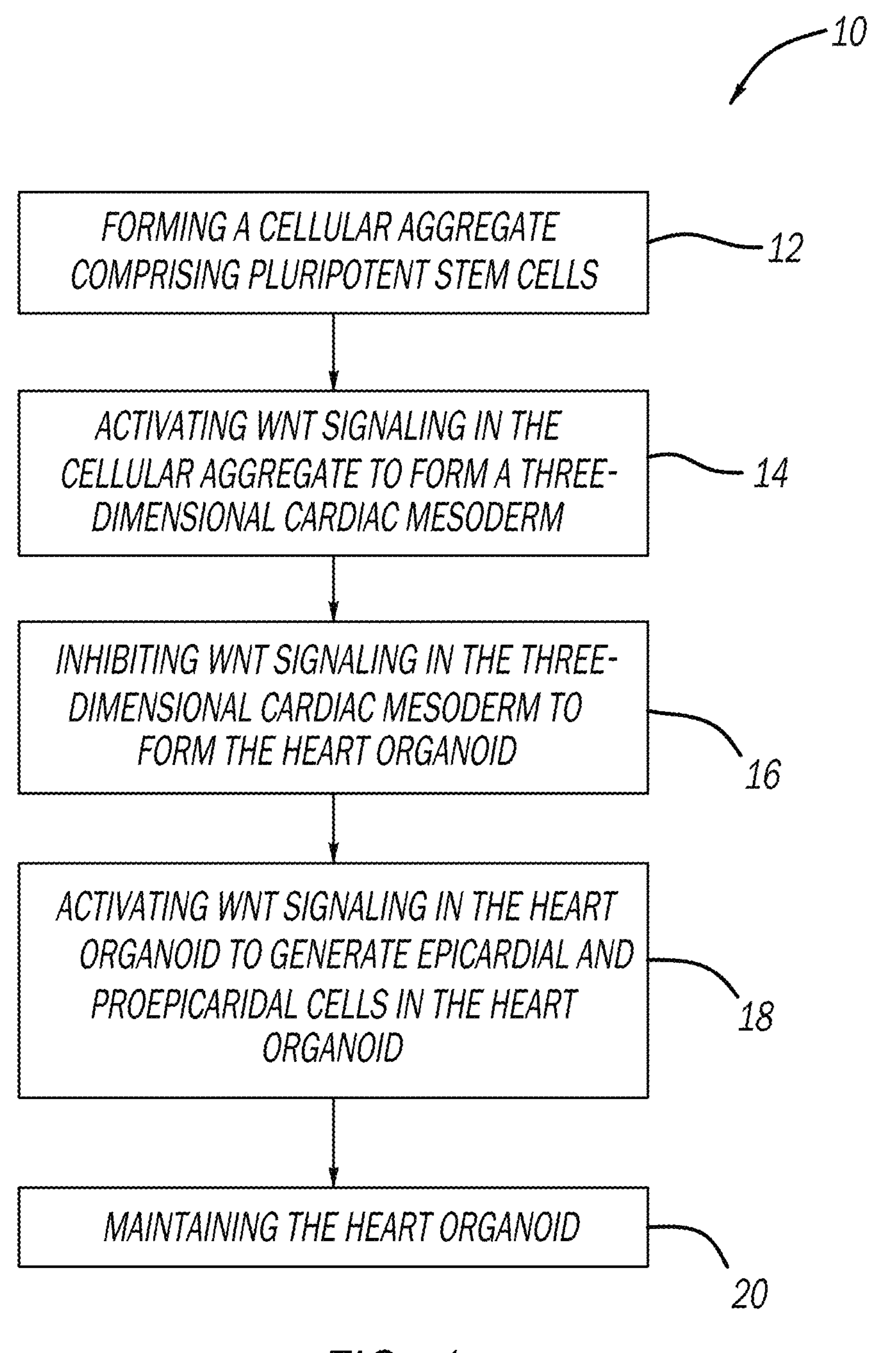
FIG. 1 is a flow chart illustrating a method of generating a heart organoid in accordance with various aspects of the current technology.

With reference to FIG. 1, the current technology provides a method 10 for generating a heart organoid. In block 12, the method comprises forming a cellular aggregate comprising pluripotent stem cells (PSCs). The cellular aggregate is formed by culturing the PSCs on a cell culture substrate, such as a cell culture flask or plate. The PSCs are non-limiting and can be, for example, any human-derived PSCs, including hPSCs, human-induced PSCs (hiPSCs), any other human stem cell-derived pluripotent cells, and combinations thereof. Specific non-limiting examples of hPSCs include the hiPSC lines iPSC-L1, AICS-0037-172, and iPSCORE_16_3, hESC line H9, and combinations thereof. Media for culturing the PSCs and methods and reagents for subculturing the PSCs are known in the art.

Before the PSCs reach confluency, they are dissociated with a detachment composition, such as Accutase® cell detachment solution (Innovative Cell Technologies), as a non-limiting example. The dissociated cells are centrifuged at greater than or equal to about 100 g to less than or equal to about 500 g, including at about 100 g, about 150 g, about 200 g, about 250 g, about 300 g, about 350 g, about 400 g, about 450 g, and about 500 g, for from greater than or equal to about 1 minute to less than or equal to about 10 minutes, including for about 1 minute, about 2 minutes, about 3 minutes, about 4 minutes, about 5 minutes, about 6 minutes, about 7 minutes, about 8 minutes, about 9 minutes, and about 10 minutes, to form a pellet. The pellet is resuspended in culture medium comprising a Rho-associated kinase (ROCK) inhibitor, such as Essential 8™ Flex medium comprising a ROCK inhibitor selected from the group consisting of Thiazovivin, Y-27632, Fasudil, and combinations thereof. The ROCK inhibitor is included at a concentration recommended by a corresponding vendor, such as at greater than or equal to about 750 nM to less than or equal to about 150 μM. The suspended PSCs are then counted and a predetermined number of the PSCs are transferred to a substrate. In certain aspects, the substrate can be an ultra-low attachment culture plate comprising a plurality of round-bottom wells, such as 6 wells, 24 wells, or 96 wells. As a non-limiting example, greater than or equal to about 2500 to less than or equal to about 15000, e.g., about 2500, about 3000, about 3500, about 4000, about 5000, about 5500, about 6000, about 6500, about 7000, about 7500, about 8000, about 8500, about 9000, about 9500, about 10000, about 10500, about 11000, about 11500, about 12000, about 12500, about 13000, about 13500, about 14000, about 14500, and about 15000, PSCs in culture medium can be transferred to at least one round-bottom well of a 96-well ultra-low attachment culture plate. The substrate is then centrifuged at greater than or equal to about 50 g to less than or equal to about 500 g, greater than or equal to about 50 g to less than or equal to about 150 g, including at about 50 g, about 75 g, about 100 g, and about 150 g, for from greater than or equal to about 1 minute to less than or equal to about 10 minutes, including for about 1 minute, about 2 minutes, about 3 minutes, about 4 minutes, about 5 minutes, about 6 minutes, about 7 minutes, about 8 minutes, about 9 minutes, and about 10 minutes, to form the cellular aggregate. The substrate carrying the cellular aggregate is maintained in an incubator at about 37° C. and about 5% $CO_2$. At least a portion of the culture medium can be changed, for example, after about 24 hours. The cellular aggregate comprises a plurality of the PSCs bonded or clustered together in a three-dimensional configuration, which may be spherical.

As shown in block 14, the method 10 also comprises activating Wnt signaling, also referred to as a "Wnt signal transduction pathway," in the cellular aggregate to cause the cellular aggregate to differentiate into a three-dimensional cardiac mesoderm. Known Wnt signaling pathways are characterized as canonical or noncanonical. In this regard, the canonical Wnt signaling pathway causes the cellular aggregate to differentiate into the cardiac mesoderm. As a brief description of the canonical pathway, Wnt binds to an extracellular domain of a Frizzled family transmembrane receptor. The Frizzled family transmembrane receptor activates a cytoplasmic phosphoprotein, Dishevelled. Activated Dishevelled inactivates the "destruction complex" comprising Axin, adenomatosis polyposis *coli* (APC), and GSK-3 by causing GSK-3 to dissociate from Axin, which leads to the inhibition of GSK-3. Because the destruction complex causes the degradation of β-catenin, the inactivation of the destruction complex allows β-catenin to translocate into the nucleus, where it acts as a transcriptional coactivator of TCF/LEF family transcription factors.

Therefore, the Wnt signaling pathway can be activated by modulating the ability of the destruction complex to degrade β-catenin, for example, by inhibiting GSK-3, or by targeting other proteins in the Wnt signaling pathway. Non-limiting examples of Wnt signaling pathway activators include CHIR99021 (a GSK-3 inhibitor), lithium chloride (a GSK-3 inhibitor), SB-216763 (a GSK-3 inhibitor), BIO (a GSK-3 inhibitor), Kenpaullone (a GSK-3 inhibitor), BML-284, WAY-262611, WAY-316606, LP-922056, ABC99, IQ-1, LY2090314, deoxycholic acid (DCA), KY-02061, KY-02327, QS11, and combinations thereof. The Wnt signaling pathway activators can be included in culture medium at concentrations known in the art, such as from greater than or equal to about 500 nM to less than or equal to about 100 mM, greater than or equal to about 750 nM to less than or equal to about 1 mM, greater than or equal to about 1 μM to less than or equal to about 50 μM, or greater than or equal to about 1 μM to less than or equal to about 15 μM. Accordingly, the activating the Wnt signaling comprises contacting the cellular aggregate with a first Wnt signaling pathway activator for greater than or equal to about 2 hours to less than or equal to about 48 hours, including for about 2 hours, about 6 hours, about 12 hours, about 24 hours, about 36 hours, and about 48 hours. Culture mediums suitable for differentiating PSCs are known in the art, and include RPMI 1640 with B27™ Supplement, minus insulin (Thermo Fisher Scientific), as a non-limiting example.

To promote the growth of the three-dimensional cardiac mesoderm, the method can also comprise contacting the cellular aggregate with at least one growth agent or growth factor that promotes cardiac growth (i.e., growth of the heart organoid), such as BMP4, ActA, fibroblast growth factor 2 (FGF2), vascular endothelial growth factor (VEGF), and transforming growth factor β (TGFβ), and combinations thereof, as non-limiting examples. Each growth agent can be included in the culture medium at individual concentrations of greater than or equal to about 1 fM to less than or equal to about 50 μM, greater than or equal to about 1 fM to less than or equal to about 1 μM, or greater than or equal to about 1 fM to less than or equal to about 1 μM. As a non-limiting example, in certain aspects, BMP4 and ActA are included in culture medium at concentrations of greater than or equal to about 0.1 pM to less than or equal to about 1 pM and greater than or equal to about 1 fM to less than or equal to about 200 fM, respectively. The contacting is performed for greater than or equal to about 30 minutes to less than or equal to about 15 days or longer, including for about 30 minutes, about 1 hour, about 2 hours, about 6 hours, about 12 hours, about 24 hours, about 36 hours, about 48 hours, about 3 days, about 4 days, about 5 days, about 6 days, about 7 days, about 8 days, about 9 days, about 10 days, about 11 days, about 12 days, about 13 days, about 14 days, about 15 days, or longer. In some aspects, the growth agent is contacted with the cellular aggregate simultaneously with the first Wnt signaling pathway activator. As such, the culture medium can include the Wnt signaling pathway activator and at least one growth agent.

As shown in block 16, the method 10 also comprises inhibiting Wnt signaling in the three-dimensional cardiac mesoderm to form the heart organoid. Wnt signaling pathway inhibitors are known in the art and include compounds that target, for example, Porcupine (PORCN; which palmitoylates Wnt, a modification required for Wnt activity), Frizzled, Tankyrase (TNKS; which targets Axin for proteolysis), TCF/LEF transcription reporter, the destruction complex, and Dishevelled (Dvl). Non-limiting examples of Wnt signaling pathway inhibitors include Wnt-059 (a PORCN inhibitor), IWP-L6, (a PORCN inhibitor), IWP-2 (a PORCN inhibitor), LGK974, ETC-159, quercetin, BC2059, niclosamide, XAV939, E7449, IWR-1, G007-LK, ICG-001, PNU-74654, windorphen, derricin, derricidin, carnosic acid, pyrvinium, NSC668036, 3289-8625, J01-017a, TMEM88, BMD4702, DK-520, sulindac, and combinations thereof. The Wnt signaling pathway inhibitors can be included in culture medium at concentrations known in the art, such as from greater than or equal to about 500 nM to less than or equal to about 50 mM, greater than or equal to about 750 nM to less than or equal to about 500 μM, greater than or equal to about 1 μM to less than or equal to about 50 μM, or greater than or equal to about 1 μM to less than or equal to about 15 μM. Accordingly, the inhibiting the Wnt signaling comprises contacting the three-dimensional cardiac mesoderm with the Wnt signaling pathway inhibitor for greater than or equal to about 2 hours to less than or equal to about 72 hours, including for about 2 hours, about 6 hours, about 12 hours, about 24 hours, about 36 hours, about 48 hours, about 60 hours, and about 72 hours.

The heart organoid, which can be an hHO, as discussed above, comprises a three-dimensional body having an interior portion and an outer surface and exhibits both first and seconds heart fields (FHF and SHF, respectively). The interior portion comprises myocardial tissue. The heart organoid also includes at least one chamber or microchamber defined by the myocardial tissue, the at least one chamber or microchamber being lined with endocardial cells. Epicardial tissue (comprising epicardial cells) is disposed on at least a portion of the surface. The heart organoid also includes cardiac fibroblasts and endothelial vasculature. Moreover, the heart organoid beats. A more detailed description of the heart organoid is provided below.

As shown in block 18, the method 10 also optionally comprises activating Wnt signaling in the heart organoid. This second Wnt signaling pathway activation (i.e., canonical Wnt signaling pathway activation) generates additional epicardial tissue and/or epicardial cells and proepicardial cells in the heart organoid and increases the complexity of the heart organoid. Suitable Wnt signaling pathway activators are discussed above. Therefore, the Wnt signaling in the heart organoid can be activated by a second Wnt signaling pathway activator, wherein the second Wnt signaling pathway activator is the same or different from the first Wnt signaling pathway activator. The second Wnt signaling pathway activator can be included in culture medium at concentrations known in the art, such as from greater than or equal to about 500 nM to less than or equal to about 100 mM, greater than or equal to about 750 nM to less than or equal to about 1 mM, greater than or equal to about 1 μM to less than or equal to about 50 μM, or greater than or equal to about 1 μM to less than or equal to about 15 μM. Accordingly, the activating the Wnt signaling in the heart organoid comprises contacting the heart organoid with the second Wnt signaling pathway activator for greater than or equal to about 15 minutes to less than or equal to about 48 hours, greater than or equal to about 15 minutes to less than or equal to about 24 hours, greater than or equal to about 15 minutes to less than or equal to about 6 hours, or greater than or equal to about 15 minutes to less than or equal to about 2 hours, including for about 15 minutes, about 30 minutes, about 45 minutes, about 1 hour, about 2 hours, about 4 hours, about 6 hours, about 12 hours, about 18 hours, about 24 hours, about 36 hours, and about 48 hours. Culture mediums suitable for the second Wnt signaling pathway activation include RPMI 1640 with B27™ Supplement, with insulin (Thermo Fisher Scientific), as a non-limiting example. After the contacting, the Wnt signaling pathway activator is removed by removing the medium comprising the Wnt signaling pathway activator and replacing the medium with fresh medium that does not include the Wnt signaling pathway activator, e.g., RPMI 1640 with B27™ Supplement, with insulin (Thermo Fisher Scientific).

As shown in block 20, the method 10 further comprises maintaining the heart organoid. The maintaining is performed by changing the medium about every 48 hours, during which time the heart organoid continues to grow, mature, and become more complex.

It is understood that the method 10 can be adjusted to generate heart organoids under predetermined conditions. In some exemplary aspects, the medium can include greater than or equal to about 2 mM to less than or equal to about 30 mM glucose and greater than or equal to about 20 pM to less than or equal to about 75 nM insulin, wherein the relative amounts of glucose and insulin are adjusted to form heart organoids under "normal" or "diabetic" conditions. For example, a normal heart organoid can be generated by performing the method 10 using a medium with physiological levels of glucose and insulin, e.g., glucose at a concentration of greater than or equal to about 2 mM to less than or equal to about 7 mM or greater than or equal to about 3 mM to less than or equal to about 6 mM and insulin at a concentration of greater than or equal to about 20 pM to less than or equal to about 250 pM or greater than or equal to about 100 pM to less than or equal to about 250 pM. Under these "normal" conditions, during the maintaining the heart organoid of block 20 of the method 10, the medium may be supplemented with a fatty acid composition to ensure the heart organoid has a sufficient source of energy. The fatty acid composition comprises at least one of oleate-bovine serum albumin (BSA), linoleate-BSA, or L-carnitine, with a total fatty acid concentration of greater than or equal to about 150 μM to less than or equal to about 250 μM. In one aspect, the fatty acid composition comprises oleate-BSA at a concentration of greater than or equal to about 30 μM to less than or equal to about 50 μM, linoleate-BSA at a concentration of greater than or equal to about 10 μM to less than or equal to about 30 μM, and L-carnitine at a concentration of greater than or equal to about 100 μM to less than or equal to about 150 μM, e.g., 40.5 μM oleate-BSA, 22.5 μM linoleate-BSA, and 120 μM L-carnitine. Alternatively, a heart organoid mimicking a developing heart in a mother with diabetes, e.g., gestational diabetes or DDP, referred to herein as a "DDP heart organoid (DDPHO)," can be generated by performing the method 10 using a medium with higher than physiological levels of glucose and insulin, e.g., glucose at a concentration of greater than or equal to about 8 mM to less than or equal to about 30 mM or greater than or equal to about 11 mM to less than or equal to about 25 mM and insulin at a concentration of greater than or equal to about 250 pM to less than or equal to about 75 nM. However, other components of the media used in the method 10 can be adjusted or additional components, e.g., growth factors, large molecules, small molecules, and the like, can be included in the media to generate heart organoids under adjustable conditions.

In some aspects, the method 10 can be performed with reference to a predetermined time scale. For example, the forming the cellular aggregate comprising PSCs of block 12 can be performed on day −2, the activating the Wnt signaling in the cellular aggregate to form the three-dimensional cardiac mesoderm of block 14 (i.e., the first Wnt signaling pathway activation) can be performed on day 0, the inhibiting the Wnt signaling in the three-dimensional cardiac mesoderm to form the heart organoid of block 16 can be performed on day 2, the optional activating Wnt signaling in the heart organoid to generate epicardial and proepicardial cells in the heart organoid of block 18 (i.e., the optional second Wnt signaling pathway activation) can be performed on day 7, and the maintaining the heart organoid of block 20 can be formed from day 7 through completion or until about day 15 or later.

A non-limiting example of the method 10 is provided as follows. In this non-limiting example, the media can be adjusted in a predetermined manner, such as to include "normal" levels of glucose and insulin or levels associated with DDP.

Day −2: the forming the cellular aggregate comprising PSCs of block 12 is performed by washing subconfluent PSCs cultured on growth factor-reduced Matrigel® extracellular matrix (Corning) with phosphate buffered saline (PBS), preparing a cell suspension of the PSCs by contacting them with Accutase®, centrifuging the cell suspension at about 300 g for about 5 minutes, resuspending the PSCs in Essential 8™ Flex medium with Thiazovivin, plating the PSCs in a well of a 96-well ultra-low attachment plate using Essential 8™ Flex medium comprising Thiazovivin, centrifuging the 96-well ultra-low attachment plate at about 100 g for about 3 minutes, and placing the 96-well ultra-low attachment plate in an incubator set at about 37° C. and about 5% $CO_2$.

Day −1: replacing the Essential 8™ Flex medium comprising Thiazovivin with fresh Essential 8™ Flex medium without Thiazovivin.

Day 0: the activating the Wnt signaling in the cellular aggregate to form the three-dimensional cardiac mesoderm of block 14 is performed by replacing the E8 Essential 8™ Flex medium without Thiazovivin with RPMI 1640 with B27™ Supplement, minus insulin (Thermo Fisher Scientific) comprising a first Wnt signaling pathway activator, BMP4, and ActA and incubating for about 24 hours.

Day 1: replacing the medium with fresh RPMI 1640 with B27™ Supplement, minus insulin (Thermo Fisher Scientific).

Day 2: inhibiting the Wnt signaling in the three-dimensional cardiac mesoderm to form the heart organoid of block 16 is performed by replacing the medium with RPMI 1640 with B27™ Supplement, minus insulin (Thermo Fisher Scientific) comprising a Wnt signaling pathway inhibitor and incubating for about 24 hours.

Day 4: replacing the medium with fresh RPMI 1640 with B27™ Supplement, minus insulin (Thermo Fisher Scientific).

Day 6: replacing the medium with fresh RPMI 1640 with B27™ Supplement, with insulin (Thermo Fisher Scientific).

Day 7: activating Wnt signaling in the heart organoid to generate epicardial and proepicardial cells in the heart organoid of block 18 is performed by replacing the medium with RPMI 1640 with B27™ Supplement, with insulin (Thermo Fisher Scientific) comprising a second Wnt signaling pathway activator; incubating for about 1 hour; replacing the medium with RPMI 1640 with B27™ Supplement, with insulin (Thermo Fisher Scientific) (including the fatty acid composition when mimicking "normal" levels of glucose and insulin); and incubating for about 48 hours.

Day 9-15 or beyond: replacing the medium with fresh RPMI 1640 with B27™ Supplement, with insulin (Thermo Fisher Scientific).

Figures 2A, 2B:
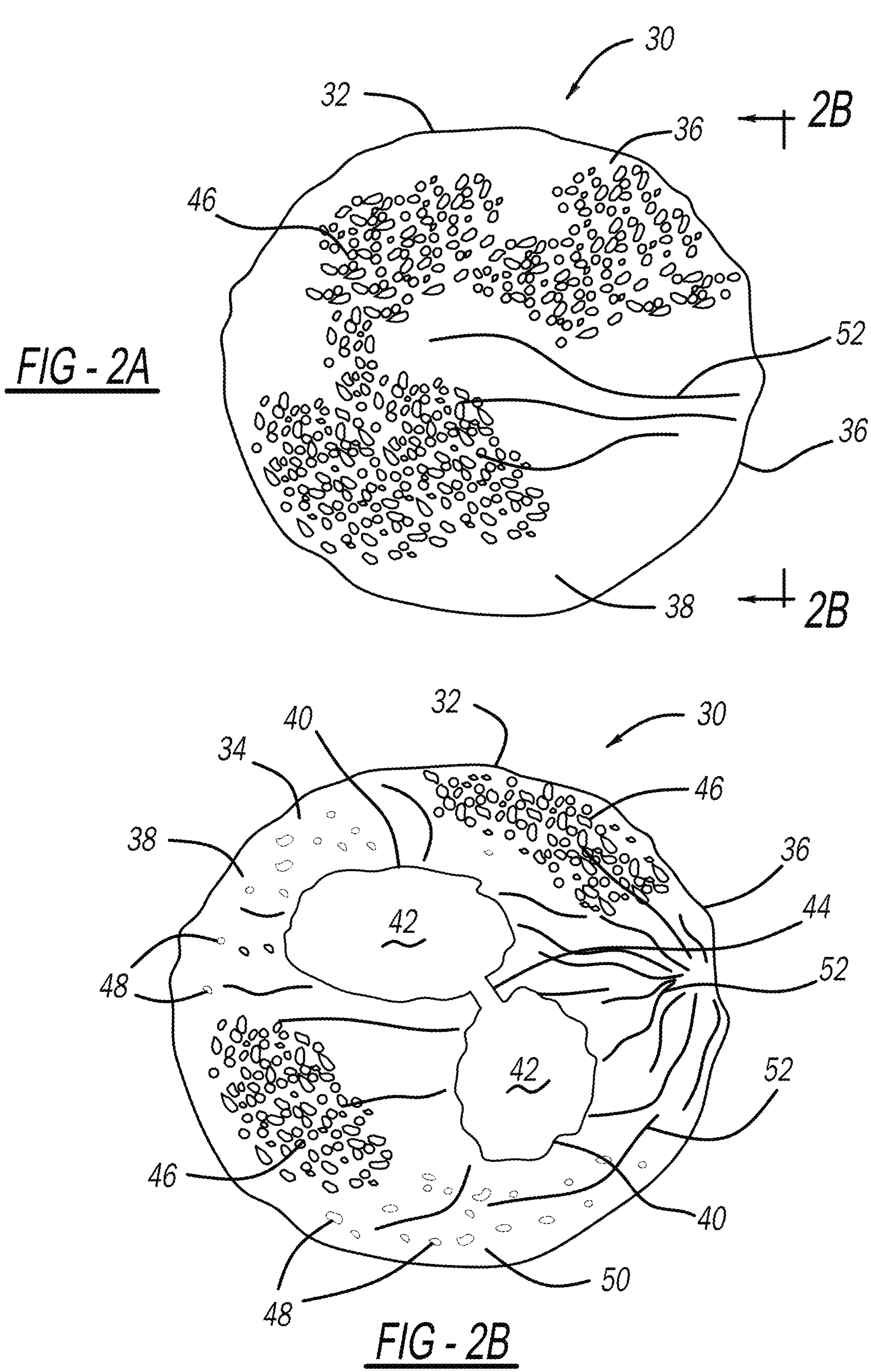
FIG. 2A is an illustration of a heart organoid in accordance with various aspects of the current technology.
FIG. 2B is a cross-section illustration of the heart organoid of FIG. 2A.

FIGS. 2A-2B show illustrations of a heart organoid 30 prepared by the method 10, as described above, and derived from cultured PSCs, where FIG. 2B is a cross-section view of the heart organoid 30 shown in FIG. 2A. The heart organoid 30 comprises a three-dimensional body 32 having an interior portion 34 and an outer surface 36. The three-dimensional body 32, and thus the heart organoid 30, have a longest diameter (a distance between two points that are furthest apart) of greater than or equal to about 0.1 mm. In some aspects, the longest diameter is greater than or equal to about 0.1 mm to less than or equal to about 5 mm. However, it is understood that the longest diameter is not limiting and may be smaller than 0.1 mm or larger than 5 mm.

The interior portion 34 and, in some aspects, a portion of the outer surface 36 comprise myocardial tissue 38 including cardiomyocytes, wherein at least a portion of the cardiomyocytes define sarcomeres. Additionally, the myocardial tissue 38 contains at least one endocardial layer 40 comprising endocardial cells or endocardial tissue that defines at least one chamber 42, for example, from one chamber 42 to about ten chambers 42 or more. In various aspects, the heart organoid has 1, 2, 3, 4, 5, 6, 7, 8, 9, or 10 chambers 42 or more, which may be microchambers. Each chamber has an individual and independent longest diameter of greater than or equal to about 50 μm to less than or equal to about 500 μm when the heart organoid is fully formed, e.g., after about 14 days of the first Wnt activation. Therefore, each chamber 42 is at least partially lined with the endocardial layer 40. When the heart organoid 30 has greater than one chamber 42, at least two of the chambers 42, e.g., all of the chambers, may be interconnected. By "interconnected," it is meant that the chambers 42 are in fluid communication with at least one other chamber 42 by way of, for example, a channel, duct, or passage 44 defined by at least one of the myocardial tissue 38 or the endocardial layer 40.

The heart organoid 30 further comprises epicardial tissue 46 comprising epicardial cells. The epicardial tissue 46 defines at least a portion of the outer surface 36. However, the epicardial tissue 46 may also be present in the interior portion 34, but generally near the outer surface 36. As such, the myocardial tissue 38 is generally disposed between the epicardial tissue 46 and the endocardial layer 40 defining the at least one chamber 42. In some aspects, the epicardial cells can undergo epithelial to mesenchymal transition (EMT) and give rise to other cell types, such as cardiac fibroblasts.

The heart organoid 30 further comprises cardiac fibroblasts 48 dispersed throughout the myocardial tissue 38 and an ECM 50 that is heart-specific and comprises ECM proteins. An endothelial vascular 52 (or vascular plexus) is disposed on the outer surface 36 and within the interior portion 34 of the heart organoid 30. The endothelial vascular 52 is defined by arteries (including, e.g., arties and/or arterioles) and veins (including, e.g., veins and/or venules) in fluid communication at capillaries. Furthermore, when mature enough, e.g., after about day 6 of the method 10, the heart organoid 30 beats.

The chambers 42 are not in fluid communication with veins or arteries that correspond to those of a naturally occurring heart and pass blood between the naturally occurring heart and lungs and between the naturally occurring heart and peripheral vasculature. The chambers 42 are contained within the heart organoid 30 and are in fluid communication with the endothelial vasculature 52 derived from the PSCs.

The current technology also provides a system or a kit that comprises at least two of the different types of media used in the method for generating the heart organoid. The system or kit comprises at least two media selected from the group consisting of Essential 8™ Flex medium; RPMI 1640 with B27™ Supplement, minus insulin cell culture supplement (Thermo Fisher Scientific) and a Wnt signaling pathway activator (e.g., about 4 μM and/or about 10 μM CHIR99021); RPMI 1640 with B27™ Supplement, minus insulin cell culture supplement (Thermo Fisher Scientific); RPMI 1640 with B27™ Supplement, minus insulin cell culture supplement (Thermo Fisher Scientific) and a Wnt signaling pathway inhibitor (e.g., about 2 μM Wnt-059); RPMI 1640 with B27™ Supplement cell culture supplement (Thermo Fisher Scientific); Essential 8™ Flex medium with a ROCK inhibitor (e.g., about 2 μM Thiazovivin); RPMI 1640 with B27™ Supplement, minus insulin cell culture supplement (Thermo Fisher Scientific) with a GSK inhibitor (e.g., about 4 μM CHIR99021), BMP4 (e.g., about 0.36 pM BMP4), and ActA (e.g., about 0.08 pM ActA); and combinations thereof. In some aspects, the media in the system or kit includes a base medium (e.g., Essential 8™ Flex medium, RPMI 1640) and aliquots of an additional component, such as B27™ Supplement cell culture supplement (Thermo Fisher Scientific), B27™ Supplement, minus insulin cell culture supplement (Thermo Fisher Scientific), a Wnt signaling pathway activator, a Wnt signaling pathway inhibitor, a ROCK inhibitor, BMP4, and/or ActA. The system or kit can be used to generate heart organoids as discussed herein.

Embodiments of the present technology are further illustrated through the following non-limiting example.

Example

Summary

CHDs constitute the most common birth defect in humans, affecting approximately 1% of all live births. The ability to understand how these disorders originate is hindered by a limited ability to model the complexity of the human heart in vitro. There is a pressing need to develop more faithful organ-like platforms recapitulating complex in vivo phenotypes to study human development and disease in vitro. An exemplary novel method to generate hHOs by self-assembly using pluripotent stem cells is reported in this example. The method is defined, highly efficient, scalable, shows high reproducibility, and is compatible with screening and high-throughput approaches. hHOs are generated using a two-step canonical Wnt signaling modulation strategy using a combination of chemical inhibitors and growth factors in completely defined culture conditions. hHOs faithfully recapitulate human cardiac development and are similar to age-matched fetal cardiac tissues at the transcriptomic, structural, and cellular level. hHOs develop sophisticated internal chambers with well-organized multi-lineage cell-type regional identities, reminiscent of the heart fields and the atrial and ventricular chambers, as well as the epicardium, endocardium, and coronary vasculature, and exhibit functional activity. It is also shown that hHOs can recreate complex metabolic disorders associated with CHD by establishing the first in vitro human model of DDP to study embryonic CHD. Morphological and metabolic effects of increased glucose and insulin show the capability of modeling the effects of DDP. The heart organoid model constitutes a powerful novel tool for translational studies in human cardiac development and disease.

Introduction

This example describes a novel small molecule-based method for creating highly complex and physiological relevant hHOs using hPSCs by manipulating cardiac developmental programs. The method relies mainly on three sequential Wnt modulation steps (activation/inhibition/activation) at specific time points on suspension embryoid bodies and produces significant heart-like structures in terms of structure, organization, functionality, cardiac cell-type complexity, ECM composition, and vascularization. Additionally, the method is less expensive compared to growth factor-based approaches and relatively simple in terms of procedure. It is also automatable, scalable, and amenable to high-content/high-throughput pharmacological screenings. To demonstrate how the method can be used to model human cardiac disease, this example employs the method (i.e., the organoid system) to model the effects of DDP on the developing embryonic heart and demonstrates the method's ability to identify therapeutic targets.

Materials and Methods.

Stem cell culture. Human iPSC lines used in this example were iPSC-L1, AICS-0037-172 (Coriell Institute for Medical Research; alias AICS), iPSCORE_16_3 (WiCell; alias iPSC-16) and hESC line H9. All PSC lines were validated for pluripotency and genomic integrity. hPSCs were cultured in Essential 8™ Flex medium containing 1% penicillin/streptomycin (Gibco) on 6-well plates coated with growth factor-reduced Matrigel® (Corning) in an incubator at 37° C. and 5% $CO_2$ until 60-80% confluency was reached, at which point, cells were split into new wells using ReLeSR™ passaging reagent (Stem Cell Technologies).

PSC monolayer cardiac differentiation. Differentiation was performed using the small molecule Wnt modulation strategy as described above, with small modifications. Briefly, differentiating cells were maintained in RPMI 1640 with B27™ Supplement, minus insulin from day 0-7 of differentiation and maintained in RPMI 1640 with B27™ Supplement (Thermo Fisher Scientific) from day 7-15 of differentiation. Cells were treated with 10 μM GSK inhibitor CHIR99021 (Selleck) for 24 hours on day 0 of differentiation and with 2 μM PORCN inhibitor, Wnt-059 (Selleck), for 48 hours from day 3-5 of differentiation. The alternative differentiation protocol was described in Bertero et al. ("Dynamics of genome reorganization during human cardiogenesis reveal an RBM20-dependent splicing factory." Nature Communications, Vol. 10, No. 1538, 2019), which is incorporated herein by reference in its entirety.

Self-assembling hHO differentiation. Accutase® (Innovative Cell Technologies) was used to dissociate PSCs for spheroid formation. After dissociation, cells were centrifuged at 300 g for 5 minutes and resuspended in Essential 8™ Flex medium containing 2 μM ROCK inhibitor Thiazovivin (Millipore Sigma). hPSCs were then counted using a Moxi Cell Counter (Orflo Technologies) and seeded at 10000 cells/well in round bottom ultra-low attachment 96-well plates (Costar) on day −2. The plate was then centrifuged at 100 g for 3 minutes and placed in an incubator at 37° C. and 5% $CO_2$. After 24 hours (day −1), 50 μl of media was carefully removed from each well and 200 μl of fresh Essential 8™ Flex medium was added for a final volume of 250 μl/well. The plate was returned to the incubator for a further 24 hours. On day 0, 166 μl (approximately ⅔ of total well volume) of media was removed from each well and 166 μl of RPMI 1640 with B27™ Supplement, minus insulin (Gibco) containing CHIR99021 (Selleck) was added at a final concentration of 4 μM/well along with BMP4 at 0.36 pM (1.25 ng/ml) and ActA at 0.08 pM (1 ng/ml) for 24 hours. On day 1, 166 μl of media was removed and replaced with fresh RPMI 1640 with B27™ Supplement, minus insulin. On day 2, RPMI 1640 with B27™ Supplement, minus insulin containing Wnt-059 (Selleck) was added for a final concentration of 2 μM Wnt-059, and the samples were incubated for 48 hours. The media was changed on day 4 and day 6. On day 6, media was changed to RPMI 1640 with B27™ Supplement (Gibco). On day 7, a second 4 μM CHIR99021 exposure was conducted for 1 hour in RPMI 1640 with B27™ Supplement. Subsequently, media was changed every 48 hours until organoids were ready for analysis. Diabetic conditions were simulated by using basal RPMI media with 11.1 mM glucose and 58 nM insulin and compared with control media containing 3.5 mM glucose and 170 pM insulin.

Lentiviral transduction. FlipGFP plasmid (Vector Builder) was transduced into a L1 iPSC line using a ZymoPURE™ II Plasmid Midiprep Kit (Fisher Scientific) according to manufacturer instructions. HEK293t were cultured in D10 media (DMEM+10% FBS+1% P/S) and later switched with reduced serum OptiMem™ (Gibco, Fisher Scientific) for 1 hour. Lipofectamine mixture (100 μl Lipofectamine 2000 (Thermo Fisher Scientific)+4 ml OptiMem™ sitting at room temperature for 5 minutes) was mixed with PLUS™ reagent mixture (200 μl PLUS™ reagent (Invitrogen, Fisher Scientific)+4 ml OptiMem™+20 μg lentiCRISPR plasmid+10 μg pMD2.gpVSVg (or pVSVgpMD2.g)+15 μg psPAX2) and was then added to the HEK293t cells and allowed to incubate at 37° C. for 6 hours. Following this, the media was changed to 30 ml D10+1% BSA per flask, without antibiotics. After 48-60 hours, the media was collected and centrifuged at 3000 rpm at 4° C. for 10 minutes. The supernatant was transferred to an Amicon® Filter Unit (Millipore-Sigma) and spun in a tabletop centrifuge at 3200 g for 30 minutes at 4° C. The flow through was dumped, and the process was repeated. The concentrated virus was aliquoted and stored at −80° C. Virus aliquot and polybrene (Fisher Scientific) were thawed at 37° C. Virus and polybrene were delivered to iPSC-L1s at low- to mid-confluences and incubated overnight. The next morning, the media was changed, and cells rested for 24 hours. Puromycin was added to the wells, and selection was maintained for approximately 3-5 days. Surviving clones were collected, replated, and expanded.

Immunofluorescence. hHOs were transferred to microcentrifuge tubes (Eppendorf) using a cut 1000-μL pipette tip to avoid disruption to the organoids and fixed in 4% paraformaldehyde solution (dissolved in PBS) for 30 minutes at room temperature. Fixation was followed by three washes in PBS-Glycine (20 mM) and incubation in blocking/permeabilization solution (10% Donkey Normal Serum, 0.5% Triton™ X-100, 0.5% BSA in PBS) on a thermal mixer (Thermo Scientific) at 300 RPM at 4° C. overnight. hHOs were then washed three times in PBS and incubated with primary antibodies (see Table 1) in Antibody Solution (1%

Donkey Normal Serum, 0.5% Triton™ X-100, 0.5% BSA in PBS) on a thermal mixer at 300 RPM at 4° C. for 24 hours. Primary antibody exposure was followed by three washes in PBS and incubation with secondary antibodies (see Table 1) in Antibody Solution on a thermal mixer at 300 RPM at 4° C. for 24 hours in the dark. The stained hHOs were washed three times in PBS before being mounted on glass microscope slides (Fisher Scientific) using VECTASHIELD® Vibrance™ Antifade Mounting Medium (Vector Laboratories). 90 μm Polybead® Microspheres (Polyscience, Inc.) were placed between the slide and the coverslip (No. 1.5) to preserve some of the three-dimensional structure of the organoids while accommodating the penetration capacity of the confocal microscope.

TABLE 1

Primary antibodies used in Example.

| | Antibody name | Host species | Dilution | Vendor |
|---|---|---|---|---|
| Primary | cTnT | Mouse | 1:200 | Abcam |
| | WT1 | Rabbit | 1:200 | Abcam |
| | ZO1 (TJP1) | Goat | 1:250 | Thermo Fisher Scientific |
| | ALDH1A2 | Rabbit | 1:200 | Abcam |
| | Vimentin | Goat | 1:200 | Abcam |
| | CD90 (THY1) | Rabbit | 1:200 | Abcam |
| | NFAT2 (NFATC1) | Rabbit | 1:100 | Abcam |
| | CD31 (PECAM1) | Rabbit | 1:50 | Abcam |
| | HAND1 | Rabbit | 1:200 | Abcam |
| | HAND2 | Rabbit | 1:200 | Abcam |
| | MYL2 | Rabbit | 1:200 | Abcam |
| | MYL7 | Mouse | 1:200 | Synaptic Systems |
| Secondary | Alexa Fluor 488 | Donkey anti-mouse | 1:200 | Thermo Fisher Scientific |
| | Alexa Fluor 488 | Donkey anti-rabbit | 1:200 | Thermo Fisher Scientific |
| | Alexa Fluor 594 | Donkey anti-mouse | 1:200 | Thermo Fisher Scientific |
| | Alexa Fluor 594 | Donkey anti-rabbit | 1:200 | Thermo Fisher Scientific |
| | Alexa Fluor 647 | Donkey anti-goat | 1:200 | Thermo Fisher Scientific |

Confocal microscopy and image analysis. Samples were imaged using two confocal laser scanning microscopes (Nikon Instruments A1 Confocal Laser Microscope; Zeiss LSM 880 NLO Confocal Microscope System) and images were analyzed using Fiji (hypertext transfer protocol secure//imagej.net/Fiji). For tissue region quantification in the organoids, DAPI positive cells were used for normalization against the target cell marker of interest across three z-planes throughout each organoid. A MaxEntropy threshold was used to measure the PECAM1+ tissue, discarding any stained region that took up less than 25 $\mu m^2$ to remove noise.

RNA-seq and transcriptomic analysis. RNA was extracted at eleven different time points throughout the hHO fabrication and differentiation protocol shown in FIG. 6A. The time points are as follows: days 0, 1, 3, 5, 7, 9, 11, 13, 15, 17, and 19. At each time point, eight organoids were removed and stored in RNAlater® (Qiagen) at −20° C. until all samples were collected. RNA was extracted using the RNEasy Mini Kit® according to manufacturer instructions (Qiagen, 74104), and the amount of RNA was measured using a Qubit™ Fluorometer (Thermo). RNA samples were sent to the MSU Genomics Core, where the quality of the samples was tested using an Agilent 2100 Bioanalyzer followed by RNA-seq using an Illumina® HiSeq® 4000 system. For RNA-seq sample processing, a pipeline was created in Galaxy. Briefly, sample run quality was assessed with FASTQC, and alignment to hg38 was carried out using HISAT2. Counts were obtained using featureCounts and differential expression analysis was performed with EdgeR. Further downstream bioinformatic analysis was performed in Phantasus 1.5.1 (artyomovlab.wustl.edu/phantasus) and ToppGene.

Figure 3:
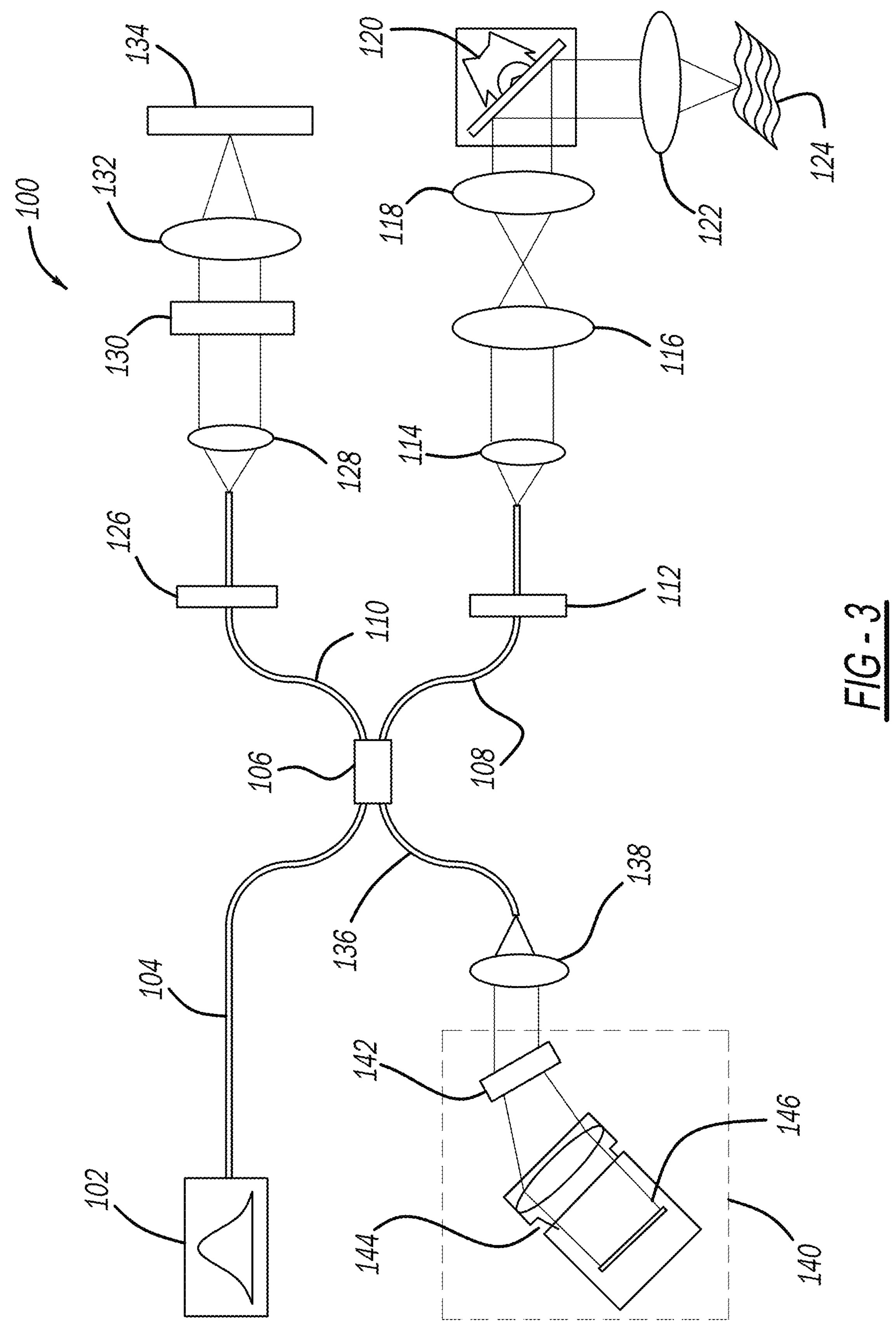
FIG. 3 is an illustration of a spectral-domain optical coherence tomography (SD-OCT) imaging system prepared in accordance with various aspects of the current technology.

OCT analysis. A customized SD-OCT system 100, as shown in FIG. 3, was developed to acquire three-dimensional images of the cardiac organoids. The SD-OCT system 100 comprises a superluminescent diode (SLD) 102, (e.g., SLD1325, Thorlabs) as a light source to provide broadband illumination with a central wavelength of about 1320 nm and a spectral range of about 110 nm. The output of the SLD 102 is sent through a first arm 104 to a fiber coupler 106, where the output is split 50/50 and transmitted to a sample arm 108 and a reference arm 110. In the sample arm 108, light is transmitted through a first polarization controller 112, through a first collimator 114, and through a first lens 116 and a second lens 118 to a galvanometer 120 (e.g., GVSM002-EC/M, Thorlabs), which scans the optical beam through an objective 122 in transverse directions on a sample 124. In the reference arm 110, light is transmitted through a second polarization controller 126, through a second collimator, through a glass 130, through a third lens 132, and to a mirror 134. The SD-OCT system 100 also comprises a detection arm 136, which passes a signal through a third collimator 138 to a custom-designed spectrometer 140, where the signal is passed through a grating 142 and a fourth lens 144 to a camera 146. The camera 146 can be a 1024-pixel line scan camera (SU1024-LDH2, Sensors Unlimited), the grating 142 can be a 1145-line pairs per mm diffraction grating (HD 1145-line pairs per mm at 1310 nm, Wasatch Photonics), and the fourth lens 144 can be an f=100 mm F-theta lens (FTH100-1064, Thorlabs). The sensitivity of the SD-OCT system 100 is measured as approximately 104 dB when operating at 20 kHz A-scan rate. The axial resolution of the SD-OCT system 100 is measured to be approximately 7 mm in tissue. Regarding the objective 122, a 5× objective lens (5× Plan Apo NIR, Mitutoyo) was used to achieve a transverse image resolution of approximately 7 mm, and the scanning range used for the cardiac organoids imaging was approximately 2 mm×2 mm. hHOs were placed into a 96-well plate with PBS and imaged at a 20-kHz A-scan rate. Obtained OCT datasets of the cardiac organoids were first processed to generate OCT images with corrected scales. Then, OCT images were further de-noised using a speckle-modulation generative adversarial network to reduce the speckle noise. Three-dimensional renderings of OCT images were performed using Amira software (Thermo Fisher Scientific).

Light-sheet imaging and analysis. A customized high-speed, axially swept light-sheet fluorescence microscope developed in-house was used. The microscope has three built-in laser channels (405 nm, 488 nm, and 561 nm) and FOV of 832×832 μm, with two custom-made multi-immersion high NA objective lenses (16× magnification, ASI) and a sCMOS camera (Andor Zyla 4.2). Fixed organoid imaging was achieved by placing the sample in a plate dish and securing it with double-sided tape (3M). The organoid was then submerged into the water. An ASI control stage brings the organoid sample into the light-sheet focus plane and submerges the two-objective lens under the water to match the refraction index for imaging. Scanning was performed with the ASI control box with a scanning step size set to 1 μm. Three identical scans with different laser channels were applied to a single organoid. After capture, fluorescence images were processed using ImageJ.

TEM sample preparation and imaging. Organoids were fixed in 4% PFA for 30 minutes followed by three washes in water, 10 minutes each. Post-fixation was performed in 1% osmium tetroxide in cacodylate buffer (pH 7.3) for 60 minutes at room temperature. Organoids were embedded in 2% agarose in water and solidified using ice for manipulation. Then, serial dilution of acetone was used for dehydration (25%, 50%, 75%, 90%, and three times in 100%) for 10 minutes each. Organoids were infiltrated with Spurr resin (Electron Microscopy Sciences) by immersion in 1:3, 2:2, and 3:1 solutions of resin in acetone, 3 hours each under agitation, following embedding in 100% resin for 24 hours and polymerization at 60° C. overnight. Ultra-thin sections (50-70 nm) were cut using RMC PTXL Leica Ultramicrotome and collected in carbon-coated copper grids, 200 mesh. Before observation, all samples were positively stained in 2% uranyl acetate and 1% lead citrate for 6 and 3 minutes, respectively. The grids were examined at 100 keV using a JEOL 1400 Flash transmission electron microscope.

Electrophysiology. The in-house MEA system described previously was used to record electrical activity of individual organoids. Live organoids were placed on the MEA inside a PDMS well in culture media supplemented with 15 mM HEPES. The MEA was placed within a Faraday cage inside an incubator at 37° C. at low humidity to avoid damage to the MEA system. Each organoid was recorded for a period of 30 minutes, and the PDMS well was washed with PBS between organoids.

Seahorse metabolic analysis. A Seahorse XFp analyzer (Agilent) was used to conduct a glycolysis rate assay as per manufacturer instructions. Three organoids per condition were dissociated separately using a STEMdiff™ Cardiomyocyte Dissociation Kit (Stem Cell Technologies) in each assay.

Data Availability. All organoid data sets shown in this example are available at the National Center for Biotechnology Information Gene Expression Omnibus repository under accession number GSE153185. RNA-seq data from monolayer differentiation method 2 and fetal heart were obtained from GSE106690. All other data generated and/or analyzed during this example is included herein.

Statistical analyses. All analyses were performed using Excel or GraphPad software. All data presented a normal distribution. Statistical significance was evaluated with a standard unpaired Student t-test (two-tailed; $P<0.05$) when appropriate. For multiple-comparison analysis, one-way ANOVA with the Tukey's or Dunnett's post-test correction was applied when appropriate ($P<0.05$). All data are presented as mean±s.d. and represent a minimum of three independent experiments with at least three technical replicates, unless otherwise stated.

Results.

Self-assembling hHOs generated by Wnt signaling modulation. The method was designed to meet at least four initial milestones: (1) high organoid quality and reproducibility; (2) high-throughput/high-content format; (3) relative simplicity (no need for special equipment outside of traditional cell culture instrumentation); and (4) defined chemical conditions for maximum control and versatility for downstream applications. The method starts by assembling hPSCs into embryoid bodies by centrifugation in ultra-low attachment 96-well plates followed by a 48-hour incubation at 37° C. and 5% $CO_2$ prior to induction. This incubation allows for spheroid stabilization and is important to increase efficiency, as other incubation times (12 hours, 24 hours) provide inferior results once differentiation starts. After induction, two-thirds of spent medium was removed and replaced with fresh medium for each medium change, resulting in gradual transitions in exposure to the different signals employed. Induction of mesoderm and cardiogenic mesoderm was achieved by sequential exposure to CHIR99021, a canonical Wnt signaling pathway activator (via specific GSK-3 inhibition), and Wnt-059, a Wnt signaling pathway inhibitor (via PORCN inhibition) (FIG. 4A). Brightfield and immunofluorescence imaging of hHOs show a significant increase in size throughout the differentiation protocol (FIG. 4B). Confocal microscopy of hHOs stained with cardiomyocyte-specific TNNT2 antibody shows that organoids started to develop sarcomeres as early as day 7 (FIG. 4B), with clear sarcomere formation and fiber assembly readily apparent by day 15 (FIG. 4C). Beating hHOs appeared as early as day 6 of the differentiation protocol, with robust and regular beating appearing by day 10 in all samples (first and second videos were made showing the beating hHOs). To determine optimal conditions for initial Wnt activation, embryoid bodies were exposed to different concentrations of CHIR99021 (4 μM, 6.6 μM, and 8 μM) on day 0 for 24 hours. On day 15, hHOs were evaluated for cardiac lineage formation by confocal microscopy (FIG. 5A). Optimal cardiogenic mesoderm induction for all hESC and hiPSC lines tested occurred at lower CHIR99021 concentrations than previously reported for cardiomyocyte monolayer differentiation protocols, which typically range from 10-12 μM CHIR. A 4 μM CHIR99021 exposure resulted in the highest cardiomyocyte content with 64±5% $TNNT2^+$ cells at day 15, versus 9.6±5% and 2.4±2% for 6.6 μM and 8 μM CHIR99021, respectively (FIGS. 4D and 5A). This difference is probably due to endogenous morphogen production and paracrine signaling within the developing hHOs, bestowed by the three-dimensional environment and inherent self-assembling properties of the organoids. hHOs treated with 4 μM CHIR99021 also displayed the best functional properties of the three concentrations (FIGS. 5B-5C). The initial hHO differentiation protocol was reproducible across multiple hPSC lines (iPSC-L1, AICS-37-TNNI1-mEGFP, iPSCORE_16_3, H9). hHOs derived from different hPSC lines exhibited similar differentiation efficiencies, beat metrics, and sizes (FIGS. 4E-4F).

Controlled induction of epicardial lineage in hHOs. To increase organoid complexity and produce more developmentally relevant structures, methods used successfully in monolayer hPSC differentiation for specific induction of epicardial cells were adapted and modified. The method includes a second activation of canonical Wnt signaling on differentiation days 7-9 to induce secondary cardiac lineages. To determine if this second activation would prime the hHOs to increase complexity and better recapitulate heart development, the effects of a second CHIR99021 exposure on day 7 (FIG. 6A) was tested. CHIR99021 was added to developing hHOs at varying concentrations (2, 4, 6, and 8 μM) and exposure lengths (1, 2, 12, 24, and 48 hours). Efficiency of epicardial cell and cardiomyocyte formation was evaluated using confocal imaging and quantification for well-established epicardial (WT1, ALDH1A2, TJP1) and cardiomyocyte (TNNT2) markers at day 15 (FIGS. 6B-6C and 7A-7B). It was found that the treatment robustly promoted the formation of proepicardium and epicardial cells (FIGS. 6B-6D and 7A). It was further found that high concentrations or long exposure times led to marked inhibition in the formation of other cardiac cell types other than epicardial cells, particularly affecting cardiomyocytes formation. A single 2 μM CHIR99021 treatment for 1 hour on differentiation day 7 produced the most physiologically relevant epicardial to myocardial ratio (60% cardiomyocytes, 10-20% epicardial cells) (FIGS. 6B-6C and 7B-7C). Structurally, a significant part of the epicardial tissue was found on external layers of the organoid and adjacent to well-defined myocardial tissue (TNNT2$^{+}$) (FIG. 6D), thus recapitulating the structural organization found in the heart. The robust expression of TJP1 on epicardial cell membranes also confirmed the epithelial phenotype of these cells (FIGS. 6C-6D).

Transcriptomic analysis reveals hHOs closely model human fetal cardiac development and produce all main cardiac cell lineages. A transcriptomic analysis was performed at different stages of organoid formation to better characterize developmental steps and the molecular identity of cells in the organoids. hHOs were collected at different time points (day 0-19) of differentiation (FIGS. 8A-8E). Unsupervised K-means clustering analysis revealed organoids progressed through three main developmental stages: day 0-1, associated with pluripotency and early mesoderm commitment; day 3-7, associated with early cardiac development; and day 9-19, associated with fetal heart maturation (FIGS. 8A and 9A-E). Gene ontology biological process analysis identified important genetic circuitry driving cardiovascular development and heart formation (FIG. 8A; raw data deposited in Gene Expression Omnibus (GEO) under GSE153185). To compare cardiac development in hHOs to that of previously existing methods, RNA-seq on monolayer iPSC-derived cardiac differentiating cells was performed using well-established protocols. The RNA-seq results were compared to publicly available datasets from previously reported monolayer cardiac differentiation protocols and human fetal heart tissue (gestational age days 57-67) (GSE106690). In all instances, hHO cardiac development transcription factor expression regulating FHF and SHF specification was similar to that observed in monolayer PSC-derived cardiac differentiation and corresponded well to that observed in fetal heart tissue (FIGS. 8B and 9A). Interestingly, gene expression profiles showed that hHOs had higher cardiac cell lineage complexity than cells that underwent monolayer differentiation, especially in the epicardial, endothelial, endocardial, and cardiac fibroblast populations (FIGS. 8C and 9B-9C). These data suggest a significant enrichment in the structural and cellular complexity of the hHOs, thus bringing them in line with fetal hearts. This was confirmed by extending the gene expression analysis to look at several widespread critical gene clusters involved in classic cardiac function, including conductance, contractile function, calcium handling, and cardiac metabolism, among others (FIG. 8D). Of special interest, hHOs produced significant amounts of heart-specific extracellular matrix, a feature present in the fetal hearts, but completely absent in monolayer differentiation protocols (FIGS. 8D and 9D). Principle component analysis showed a clear progression in development in the hHOs from day 0-19 (FIG. 9E). Overall, hHOs had individual expression profiles best matching those of fetal hearts, and the global hHO transcriptome was closer to that observed in fetal hearts than in any of the monolayer protocols, as determined by hierarchical clustering (FIG. 8E).

hHOs recapitulate heart field specification and atrial and ventricular chamber formation. The FHF and SHF are two cell populations found in the developing heart. Cells from the FHF contribute to the linear heart tube formation, followed by migrating cells belonging to the SHF that contribute to further expansion and chamber formation. Evidence of cells representing both heart fields was found in the organoids. HAND1 (FHF) and HAND2 (SHF) are members of the Twist family of basic helix-loop-helix (bHLH) transcription factors that play key roles in the regulation of numerous cell types in the developing heart. Immunofluorescence of day-8 hHOs showed well-differentiated, segregated regions of HAND1 (FIG. 10A) and HAND2 (FIG. 10D) cells, suggesting that both FHF and SHF progenitors are present and separate into their respective heart fields. In human hearts, the left ventricle ultimately forms from FHF progenitors and the atria form from SHF progenitors. Therefore, a determination was made as to whether the hHOs contain cardiomyocytes committed to either the atrial or ventricular lineages. Immunofluorescence for MYL2 (which encodes myosin light chain-2, ventricular subtype) and MYL7 (encodes myosin light-chain 2, atrial subtype) in day-15 hHOs showed cardiomyocytes positive for both subtypes. The two different populations localized to different regions of the organoid and were in close proximity, which mirrors the expression pattern seen in human hearts (FIG. 10C). The expression of HAND1, HAND2, and MYL7 transcripts in the hHOs increased throughout the differentiation protocol and were similar to that observed in human fetal hearts, while MYL2 increased to a lesser degree (FIGS. 9A and 9C). Adding India ink to the media for contrast, the beating organoids were recorded under a light microscope and central chamber-like structures surrounded by beating tissue were observed (a third video was made to show the beating tissue). Taken together, these data suggest that the differentiation of the hHOs involves heart field formation, chamber specification, and cardiomyocyte specification into atrial and ventricular subpopulations, both of which further emphasize their recapitulation of human cardiac development.

Heart organoids produce multiple cell cardiac lineages and acquire cardiac-specific morphological functionality. Results from the transcriptomic analysis (FIGS. 8A-8E) suggest that the second CHIR99021 exposure led to the formation of other mesenchymal lineages and higher complexity in hHOs. To evaluate this finding, an immunofluorescence analysis was performed for secondary cardiac cell lineages. Confocal imaging confirmed the presence of cardiac fibroblasts positive for THY1 and VIM (FIG. 11A), which made up 12±2% of the tissues in the hHOs (FIG. 11E), similar to the composition of the fetal heart described in the literature. Further confocal imaging revealed a robust interconnected network of endothelial cells (PECAM1$^{+}$), and vessel-like formation throughout the organoid (FIG. 11B). Higher magnification images uncovered a complex web of endothelial cells adjacent to or embedded into myocardial tissue (FIG. 11C; a fourth video was made showing the web and myocardial tissue). Three-dimensional reconstruction of confocal imaging stacks showed a well-connected endothelial network intertwined in the hHO tissue (the fourth video shows the network, and a fifth video was made, which also shows the network). These results strongly indicate that during hHO development, self-organizing endothelial vascular networks emerge in response to the three-dimensional cardiovascular environment, adding a coronary-like vascular network to the organoids (a phenomenon not observed before). Chamber-like areas within the TNNT2$^{+}$ were observed and were suspected of possessing chamber-like qualities and mimicking early heart chamber formation. Immunofluorescence analysis for the endocardial marker NFATC1 revealed the formation of an endocardial layer of NFATC1$^{+}$ cells lining these spaces, similar to the endocardial lining of the heart (FIG. 11D). FIG. 11E shows a quantification of the contribution of these different cell populations to the organoids. Next, OCT was employed to characterize chamber properties using minimally invasive means, thus preserving chamber physical and morphological properties. OCT showed clear chamber spaces within the hHOs, typically with one or two large chambers near the center of the organoids (FIGS. 12A and 13A-13C). Three-dimensional reconstruction of the internal hHO topology revealed a high degree of interconnectivity between these chambers (sixth, seventh, and eighth videos were made showing the interconnected chambers). The presence of chambers was further confirmed using light-sheet imaging of whole organoids (FIG. 12B). Given the relatively large size of the heart organoids (up to 1 mm), whether the formation of these chambers could be associated to internal cell death was verified. To do this, a transgenic hiPSC line expressing FlipGFP, a non-fluorescent engineered GFP variant which turns fluorescent upon effector caspase activation and is thus a reporter for apoptosis, was created. FlipGFP organoids in control conditions exhibited no fluorescence indicating that there is no significant programmed cell death (FIG. 13D). This observation is further supported by the lack of internal cellular debris observed during confocal imaging (data not shown). Doxorubicin-treated hHOs were used as a positive control for apoptosis (FIG. 13D), with evident signs of cell death.

Ultrastructural analysis of hHOs showed features similar to those typically found in age-matched human fetal hearts, with well-defined sarcomeres surrounded by mitochondria and the presence of gap junctions and T-tubules (FIG. 12C). Electrophysiological activity was measured to determine functionality. An in-house multi-electrode array (MEA) sensor 150 technology (FIG. 14) was developed and utilized to show that hHOs 152 exhibit normal electrophysiological activity, with well-defined QRS complexes and T and P waves, and regular action potentials (FIG. 12D). As shown in FIG. 14, the MEA sensor 150 applied to the hHO 152 is disposed within a Faraday cage 154 positioned in an incubator 156. A recording board 158 relays signals from the MEA sensor 150 to a software interface 160.

BMP4 and ActA improve heart organoid chamber formation and vascularization. The growth factors BMP4 and ActA have frequently been used as alternatives to small molecule Wnt signaling manipulation, since they are the endogenous morphogens that pattern the early embryonic cardiogenic mesoderm and determine heart field specification in vivo. It was suspected that BMP4 and ActA, in combination with the small molecule Wnt activation/inhibition protocol, could synergistically improve the ability of hHOs to recapitulate cardiac development in vitro. The effect of BMP4 and ActA was tested in the context of the optimized protocol by adding the two morphogens at 1.25 ng/ml and 1 ng/ml, respectively (recommended concentrations found in the literature), at differentiation day 0 in conjunction with 4 μM CHIR99021. No significant differences were found in formation of myocardial (TNNT2+) or epicardial (WT1+/TJP1+) tissue between control and treated hHOs (FIG. 15A). However, significant differences in organoid size were observed, as hHOs treated with growth factors were about 15% larger in diameter (FIGS. 15B-15C). This difference may correspond with the increase in microchamber number and connectivity, as BMP4/ActA-treated hHOs had more microchambers that were approximately 50% more interconnected with other chambers compared to control hHOs (FIGS. 15D-15E and 15G). Immunofluorescence and confocal analysis of organoids treated with BMP4 and ActA showed a 400% increase in the area of PECAM1+ tissue, indicating a significant effect on organoid vascularization (FIGS. 15F and 15H), which might also account for the increase in hHO size.

Modeling DDP-induced CHD using hHOs. As proof-of-concept on the utility of the system, it was decided to use the hHO model to study the effects of DDP on cardiac development. Diabetes affects a large number of the female population in reproductive age, and there is significant epidemiological evidence linking diabetes during the first trimester of pregnancy to increased risk of CHD (up to 12% in some cases, a 12-fold increase), but little understanding of the underlying mechanisms. To do this, hHO culture conditions were modified to reflect reported normal physiological levels of glucose and insulin (3.5 mM glucose, 170 pM insulin, NHOs) and reported diabetic conditions (11.1 mM glucose and 58 nM insulin, DDPHOs). Interestingly, normal conditions also differed from the original protocol's glycemic and insulin conditions (due to most media being originally developed for cancer cell culture and containing abnormally high levels of glucose). NHOs developed at a slower pace than their higher glucose counterparts but presented better physical organization, with formation of heart tube-like structures and later segmentation into different well-defined areas reminiscent of heart looping and chamber formation (FIG. 17A) without evidence of cell death or abnormal physiology (FIGS. 16A-16H and 17A-17F). However, their structure was also significantly more delicate and could easily be damaged (FIG. 16A). NHOs and DDPHOs showed significant morphological differences as early as day 4 of differentiation. NHOs were slower to grow and exhibited patterning and elongation between days 4 and 8, while DDPHOs remained spherical throughout the two-week period (FIG. 16A). DDPHOs were also significantly larger in size after 1 week of differentiation (FIG. 16B), suggesting hypertrophy, a common outcome of diabetes in newborns, which typically suffer from macrosomia in all organs. Electrophysiology analysis showed increased amplitude and frequency in action potentials in DDPHOs (FIGS. 16C and 17B-17D) suggesting higher activity in the diabetic organoids. Metabolic assays for glycolysis and oxygen consumption revealed decreased oxygen consumption rate in DDPHOs and increased glycolysis when compared to NHOs (FIGS. 16B, 16E, and 17E). TEM imaging revealed DDPHOs had a reduced number of mitochondria surrounding sarcomeres (FIG. 16F) and a significantly larger number of lipid droplets, suggesting dysfunctional lipid metabolism. None of these phenotypes were found in NHOs. Confocal microscopy of myocardial and epicardial markers revealed a drastic difference in morphological organization, as DDPHOs contained epicardial tissue surrounded by myocardial tissue, whereas NHOs contained epicardial tissue on top of or beside myocardial tissue, as expected (FIG. 16G). Furthermore, compared with normal glycemia conditions, diabetic hHOs showed decreased MYL2$^{+}$ ventricular cardiomyocytes and enlarged chambers, again suggesting a dilated cardiomyopathy-like phenotype (FIG. 16H). These differences in impaired structural/developmental organization and lipid metabolism in DDPHOs are consistent with expected phenotypes found in diabetic patients and newborns exposed to high glucose/insulin. Taken together, the data suggest significant molecular and metabolic perturbations between NHOs and DDPHOs consistent with previous studies on DDP suggesting increased oxidative stress, cardiomyopathy, and altered lipid profiles and constitute a significant step forward to model metabolic disorders in human organoids.

DISCUSSION

In recent years, hPSC-derived cardiomyocytes have become critically useful tools to model aspects of heart development, human genetic cardiac disease, therapeutic screening, and cardiotoxicity testing. Nonetheless, the complex structural morphology and multitude of tissue types present in the human heart impose severe limitations to current in vitro models. Previous attempts at generating three-dimensional cardiac tissues typically included cardiomyocytes and only one or two other cardiac cell lineages. Here, it was desired to create a highly-reproducible, scalable, and novel differentiation protocol that yields physiologically relevant hHOs with high structural and multicell-type complexity using hPSCs. Multistep manipulation conditions for canonical Wnt signaling using GSK-3 and PORCN inhibitors was created and optimized. These conditions lead to the formation of most cardiac lineages in a self-assembling heart organoid with similar properties to the fetal heart. This method consistently yields cardiac organoids comprised of approximately 59% cardiomyocytes, 15% epicardial cells, 13% endocardial cells, 12% cardiac fibroblasts, and 1% endothelial cells (by area) and shows robust beating throughout the entire structure within a week from differentiation initiation. The organization and specification of these cell types are likely controlled at least in part through HAND transcription factor expression, as HAND1 and HAND2 lineage-derived cells contribute to the developing myocardium, epicardium, endocardium, and vasculature. The fact that both FHF and SHF HAND markers are present suggests that they play a role in the development of the structural and cell-type complexity seen in the hHOs. Notably, hHOs were successfully derived from three independent iPSC lines and one ESC line, demonstrating reproducibility. The fetal-like morphology of the cardiomyocytes and the self-assembling nature of the hHOs allude to a complex three-dimensional structure containing a multitude of cardiac cell lineages allowing for higher-order interactions between different heart tissues. When compared with existing cardiomyocyte monolayer differentiation methods, hHOs showed higher expression of genes associated with conduction, contractile function, calcium handling, and various cardiac cell populations, which better resembles gene expression data retrieved from human fetal hearts. The depiction of a complex transcriptome highly recapitulative of human fetal heart tissue further strengthens the complexity and validity of the hHO as a model of human heart development.

The epicardium, an epithelial layer that encapsulates the human heart, is involved in many important heart processes, including heart development, metabolism, lipid homeostasis, and myocardial injury responses. Epicardial signaling cascades are essential for cardiac lineage specification. During embryonic development, cells from the proepicardial organ (PEO), an extra-cardiac cluster of embryonic cells, migrate to the surface of the heart to form the epicardium. Some of these cells can undergo EMT to generate other cardiac lineages including cardiac fibroblasts. Due to its capacity to communicate with the myocardium and its ability to mobilize stem cell populations, the epicardium has become a key focus of research in cardiac regeneration and repair. The epicardium also plays a fundamental but under-explored role in multiple types of cardiovascular and metabolic disease, including diabetic cardiomyopathy, coronary artery disease, and metabolic syndrome. In this last condition, epicardial-derived fat experiences a significant expansion and correlates strongly with morbidity, highlighting the potential relevance of the epicardium to human disease. Inspired by a previous epicardial differentiation method, conditions for producing heart organoids with well-defined regions of epicardial tissue adjacent to myocardial tissue were created and optimized. These epicardial-myocardial interactions are important in mammalian heart development and function as epicardial cells increase cardiomyocyte growth in three-dimensional engineered heart tissues (EHTs) and co-transplantation of both cell types into rat hearts increases endothelial cell production. The hHO protocol described herein will facilitate the study and modeling of physiologically relevant epicardial-myocardial interactions in vitro.

The important role that cardiac fibroblasts play on cardiac development and cardiac matrix production/organization is often overlooked in in vitro models. Most cardiac fibroblasts in embryonic development arise from the PEO, highlighting the necessity of epicardial induction in developmental heart models. These fibroblasts facilitate cardiomyocyte functionality in h PSC-derived three-dimensional cardiac microtissues, and as such, their inclusion in any in vitro human heart model is paramount. Immunofluorescence analysis of the hHOs revealed the presence of cardiac fibroblast markers including the membrane glycoprotein Thy1, which is involved in cell-cell and cell-matrix adhesion, and the intermediate filament protein Vimentin, typically seen in cells of mesenchymal lineage. Other cardiac fibroblast markers were found in the hHOs via RNA-seq analysis, including DDR2, which plays an important role in EMT, and the FHF marker PDGFR$\alpha$, which is also crucial for vascularization during development. These data provide a strong indication of the increased complexity of the hHO system and its close resemblance to fetal heart tissue.

An acute limitation of many organoid systems is a lack of a functional vascular network to facilitate the exchange of nutrients and removal of waste material, as they instead rely solely on diffusion. Several vascularized organoids have been described in the literature modeling the brain, kidney, and blood vessel; however, none have been described in cardiac organoids. In these studies, various techniques are used to induce vascularization including implantations in mice, culturing the organoids under flow, and embedding endothelial cells in a Matrigel®/collagen matrix and inducing their migration to create a vascular network. Remarkably, the formation of a robust interconnected vascular plexus was observed in the final protocol for hHOs without any additional steps.

In addition to vasculature, spontaneous hHO reorganization into interconnected chambers was also observed, a powerful three-dimensional feature indicative of recapitulation of fetal-like organogenesis. Previous studies of microchamber formation in vitro utilized micropatterning of hPSCs into a confined area to generate three-dimensional cardiac microchambers with cell-free regions, a myofibroblast perimeter, and nascent trabeculae. Other reports have produced three-dimensional bio-printed hPSC-laden scaffolds and differentiated them to beating cardiac microtissues with two chambers. While the structures generated in these studies showed some fetal-like formation of cardiac microchambers, they lacked endocardial tissue, a crucial player in heart maturation and morphogenesis. The hHOs reported here form multiple microchambers lined with NFATC1+ endocardial cells which are interconnected as seen in the OCT cross-sectional imaging (which are visible in the sixth, seventh, and eighth videos). Expression of specific ECM genes in the hHOs resembling the fetal heart matrix, such as COL1A1, COL4A1, COL5A2, FBN1, EMILIN1, HSPG2, and LAMA2 (FIG. 9D) might be an important factor in chamber organization, as ECM components have been shown to mediate the formation of chambered mouse cardiac organoids. Therefore, the expression of these genes in the hHOs deserves further examination in the future. The microchambers may also specify further into atrial-like and ventricular-like regions, as cardiomyocytes from both lineages are seen in separate regions in the hHOs.

Together with the use of small-molecule inhibitors that manipulate canonical Wnt signaling pathways, successful cardiomyocyte differentiation has been achieved in the past using morphogens, such as BMP4 and ActA. These growth factors lead to the induction of cardiac mesoderm in the embryo, and established differentiation protocols using them show effective differentiation to various cardiac mesoderm progenitors. Recently, gradient exposures to specific concentrations of BMP4 and ActA have been studied in the specification of FHF and SHF formation. The addition of these growth factors to the initial CHIR exposure in the hHO differentiation protocol led to improved morphological features, such as increased microchamber interconnectivity and vascularization.

In the past few years, three-dimensional human cardiac tissues have been used to model genetic and non-genetic conditions (myocardial infarction, drug cardiotoxicity). This example shows that the hHOs can be valuable models to study CHD in DDP, a significantly understudied medical problem. Maternal diabetes is one of the most common causes of newborn CHD (up to 12% of newborns from diabetic mothers have some form of CHD). Using healthy and diabetic levels of glucose and insulin in the differentiation media, the effects of diabetic conditions on the developmental process of hHOs was demonstrated. Organoids developing in healthy conditions displayed active structural changes including patterning, while hHOs in diabetic conditions developed larger and spherical. This finding may hint towards an effect on the ability of the early heart to properly form the heart tube, leading to malformations of the heart as it loops into four chambers. Furthermore, the larger size of the diabetic hHOs suggests an early sign of cardiac hypertrophy, a hallmark of maternal DDP. The apparent reduction in mitochondria, dysfunctional lipid metabolism, and impaired structural organization of key tissue types hint towards unraveling the pathogenesis of CHD in DDP. Future studies will utilize this organoid differentiation protocol to explore these dysfunctions and malformations and conduct high-throughput screening for potential targets for remedies. In summary, this example describes a highly reproducible and high-throughput hHOs derivation method, with multi-cell-type and morphological complexity closely recapitulating that of the developing human fetal heart. This model constitutes a valuable tool to investigate the development of the human heart and the etiology of congenital heart defects. Furthermore, refinement and improved maturation protocols might allow for the modeling of adult cardiac settings, such as cardiotoxicity screening and cardiovascular-related disorders.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for generating a heart organoid, the method comprising:

forming a cellular aggregate comprising pluripotent stem cells;

a first activating step comprising contacting the cellular aggregate with a first Wnt signaling pathway activator to cause the cellular aggregate to differentiate into a three-dimensional cardiac mesoderm, wherein the first Wnt signaling pathway activator is a glycogen synthase kinase 3 (GSK 3) inhibitor; and contacting the three-dimensional cardiac mesoderm with a Wnt signaling pathway inhibitor to form the heart organoid, wherein the Wnt signaling pathway inhibitor is a Porcupine (PORCN) inhibitor;

wherein the heart organoid comprises myocardial tissue, endocardial tissue defining at least one cardiac chamber, and epicardial tissue disposed on at least an outer surface of the myocardial tissue; and wherein the heart organoid beats; and wherein the heart organoid is generated without embedding cells in a hydrogel matrix.

2. The method according to claim 1, wherein the first activating step further comprises contacting the cellular aggregate with at least one growth agent.

3. The method according to claim 1, further comprising:

a second activating step comprising activating Wnt signaling in the heart organoid by contacting the heart organoid with a second Wnt signaling pathway activator to increase the amount of proepicardial tissue in the heart organoid.

4. The method according to claim 1, wherein the heart organoid is generated in media comprising glucose at a concentration of greater than or equal to about 2 mM to less than or equal to about 7 mM and insulin at a concentration of greater than or equal to about 20 pM to less than or equal to about 250 pM.

5. The method according to claim 1, wherein the heart organoid is generated in media comprising glucose at a concentration of greater than or equal to about 8 mM to less than or equal to about 30 mM and insulin at a concentration of greater than or equal to about 250 pM to less than or equal to about 75 nM.

6. A heart organoid prepared according to the method of claim 1.

7. The method according to claim 3, wherein the contacting the cellular aggregate with the first Wnt signaling pathway activator is for greater than or equal to about 2 hours to less than or equal to about 48 hours;

the contacting the three-dimensional cardiac mesoderm with the Wnt signaling pathway inhibitor is for greater than or equal to about 24 hours to less than or equal to about 72 hours; and the contacting the heart organoid with the second Wnt signaling pathway activator is for greater than or equal to about 15 minutes to less than or equal to about 24 hours.

8. The method according to claim 7, wherein the contacting the cellular aggregate with the first Wnt signaling pathway activator comprises contacting the cellular aggregate with a Wnt-activating composition comprising greater than or equal to about 1 μM to less than or equal to about 1 μM of the first Wnt signaling pathway activator.

9. The method according to claim 7, wherein the contacting the three-dimensional cardiac mesoderm with the Wnt signaling pathway inhibitor comprises contacting the three-dimensional cardiac mesoderm with a Wnt-inhibiting composition comprising greater than or equal to about 1 μM to less than or equal to about 15 μM of the Wnt signaling pathway inhibitor.

10. The method according to claim 7, wherein the contacting the heart organoid with the second Wnt signaling pathway activator comprises contacting the cellular aggregate with a Wnt-activating composition comprising greater than or equal to about 1 μM to less than or equal to about 15 μM of the second Wnt signaling pathway activator.

11. The method according to claim 7, wherein the forming the cellular aggregate comprises:

transferring the pluripotent stem cells to a substrate; and centrifuging the substrate at greater than or equal to about 50 g to less than or equal to about 500 g for greater than or equal to about 1 minute to less than or equal to about 10 minutes.

12. The method according to claim 7, wherein:

the forming the cellular aggregate is performed on day −2;

the contacting the cellular aggregate with the first Wnt signaling pathway activator is performed on day 0;

the contacting the three-dimensional cardiac mesoderm with the Wnt signaling pathway inhibitor is performed on day 2; and the contacting the heart organoid with the second Wnt signaling pathway activator is performed on day 7.

13. A heart organoid prepared according to the method of claim 7.

14. An in vitro generated heart organoid comprising:

a three-dimensional body having an interior portion and an outer surface, the interior portion comprising myocardial tissue;

endocardial cells defining at least one cardiac chamber within the myocardial tissue, wherein the at least one cardiac chamber is not in fluid communication with veins or arteries that correspond to those of a naturally occurring heart; and epicardial tissue disposed on at least a portion of the outer surface;

wherein the heart organoid beats; and wherein the heart organoid is derived from cultured pluripotent stem cells.

15. The heart organoid according to claim 14, further comprising:

endothelial vasculature at least partially embedded within the heart organoid; and cardiac fibroblasts disposed within the myocardial tissue.

16. The heart organoid according to claim 14, further comprising:

a heart-specific extracellular matrix.

17. The method of claim 1, wherein the forming the cellular aggregate comprising pluripotent stem cells comprises washing subconfluent pluripotent stem cells cultured on extracellular matrix with phosphate buffered saline and preparing a cell suspension comprising the pluripotent stem cells and medium.

18. The method of claim 1, wherein the heart organoid consists essentially of cardiomyocytes, epicardial cells, endocardial cells, cardiac fibroblasts and endothelial cells.

* * * * *